(12) United States Patent (10) Patent No.: US 12,667,634 B2
Lane et al. (45) Date of Patent: *Jun. 30, 2026

(54) GAS TREATMENT DELIVERY SYSTEMS AND METHODS

(71) Applicant: ImmunoRes-Therapeutics, LLC, Natchez, MS (US)

(72) Inventors: Ronald Howard Lane, Natchez, MS (US); Barry Davignon, Terre Haute, IN (US); Peter Heath, Sussex, WI (US)

(73) Assignee: ImmunoRes-Therapeutics, LLC, Natchez, MS (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/959,147

(22) Filed: Oct. 3, 2022

(65) Prior Publication Data

US 2023/0201437 A1 Jun. 29, 2023

Related U.S. Application Data

(63) Continuation of application No. 16/279,476, filed on Feb. 19, 2019, now Pat. No. 11,471,579, which is a
(Continued)

(51) Int. Cl.
*A61L 2/20* (2026.01)
*A61K 35/14* (2015.01)
(Continued)

(52) U.S. Cl.
CPC ............... *A61L 2/20* (2013.01); *A61K 35/14* (2013.01); *A61M 1/025* (2013.01);
(Continued)

(58) Field of Classification Search
CPC .. A61M 1/025; A61M 1/0259; A61M 1/0272; A61M 1/0281; A61M 1/3486;
(Continued)

(56) References Cited

U.S. PATENT DOCUMENTS 4,632,980 A * 12/1986 Zee ....................... A61L 2/0094
530/382
11,471,579 B2 * 10/2022 Lane ................... A61M 1/3482
(Continued)

FOREIGN PATENT DOCUMENTS

CN 201603164 U 10/2010
CN 102802643 A 11/2012
(Continued)

OTHER PUBLICATIONS

Almgren et al., Nonlinear Dynamics of Thin Films and Fluid Interfaces. BANFF Institute Workshop. 11 pages, (2003). (The month of publication is not available; however, the year of publication is sufficiently earlier than the effective U.S. filing date and any foreign priority date so that the particular month of publication is not in issue.).
(Continued)

*Primary Examiner* — John Kim
(74) *Attorney, Agent, or Firm* — McCarter & English, LLP; Jonathan M. Sparks

(57) ABSTRACT

The present disclosure provides apparatuses and systems for delivering a measureable absorbed-dose of a gaseous activating agent to a fluid including a biological liquid and/or cells. The apparatuses or systems include a gas-fluid contact device configured to controllably rotate or oscillate a control member having an interior surface in contact with the fluid and a control system configured to control rotation or oscillation of the contact member by the gas-fluid contact device. In some embodiments, the control system is further configured to control absorption of the gaseous activating agent by the fluid. The present disclosure also provides methods of treating a fluid including a biological liquid or cells with a gaseous activating agent to controllably activate the fluid.

18 Claims, 26 Drawing Sheets

Related U.S. Application Data continuation of application No. PCT/US2017/047690, filed on Aug. 18, 2017.

(60) Provisional application No. 62/399,008, filed on Sep. 23, 2016, provisional application No. 62/377,122, filed on Aug. 19, 2016.

(51) Int. Cl.

| | |
|---|---|
| *A61L 2/202* | (2026.01) |
| *A61L 2/24* | (2006.01) |
| *A61M 1/02* | (2006.01) |
| *A61M 1/34* | (2006.01) |
| *A61M 1/36* | (2006.01) |
| *A61L 2/26* | (2006.01) |
| *A61L 103/05* | (2026.01) |
| *A61L 103/09* | (2026.01) |

(52) U.S. Cl.

CPC ........ *A61M 1/0259* (2013.01); *A61M 1/0272* (2013.01); *A61M 1/0281* (2013.01); *A61M 1/3482* (2014.02); *A61M 1/3486* (2014.02); *A61M 1/3687* (2013.01); *A61L 2/202* (2013.01); *A61L 2/24* (2013.01); *A61L 2/26* (2013.01); *A61L 2103/05* (2026.01); *A61L 2103/09* (2026.01); *A61M 2202/0216* (2013.01)

(58) Field of Classification Search

CPC .............. A61M 1/3482; A61M 1/3687; A61M 2202/0216; A61K 35/14; A61L 2/0005; A61L 2/0094; A61L 2/20; A61L 2/202; A61L 2/24; A61L 2/26; A61L 2202/22; A61L 2103/05; A61L 2103/09

See application file for complete search history.

(56) References Cited

U.S. PATENT DOCUMENTS

| | | |
|---|---|---|
| 2011/0031190 A1 | 2/2011 | Latino et al. |
| 2023/0201437 A1 | 6/2023 | Lane et al. |

FOREIGN PATENT DOCUMENTS

| | | |
|---|---|---|
| JP | 62-21 A | 1/1987 |
| JP | 2005-508829 A | 4/2005 |
| WO | WO-2010/147677 A2 | 12/2010 |
| WO | WO-2011/0031190 A2 | 3/2011 |
| WO | WO-2018/035504 A1 | 2/2018 |

OTHER PUBLICATIONS

Bocci et al., The ozone paradox: ozone is a strong oxidant as well as a medical drug. Med Res Rev. Jul. 2009;29(4):646-82.

Bryan et al., Mechanoresponsive networks controlling vascular inflammation. Arterioscler Thromb Vasc Biol. Jun. 2014;34(10):2199-205.

Bufi et al., Human Primary Immune Cells Exhibit Distinct Mechanical Properties that Are Modified by Inflammation. Biophys J. May 5, 2015;108(9):2181-90.

Cai et al., Plasma membrane translocation of trimerized MLKL protein is required for TNF-induced necroptosis. Nat Cell Biol. Jan. 2014;16(1):55-65 (published online Dec. 8, 2013).

Cho et al., Phosphorylation-driven assembly of the RIP1-RIP3 complex regulates programmed necrosis and virus-induced inflammation. Cell. Jun. 12, 2009;137(6):1112-23.

Cvetanovic et al., Innate immune discrimination of apoptotic cells: repression of proinflammatory macrophage transcription is coupled directly to specific recognition. J Immunol. Jan. 15, 2004;172(2):880-9.

Decathelineau et al., The final step in programmed cell death: phagocytes carry apoptotic cells to the grave. Essays Biochem. 2003;39:105-17. (The month of publication is not available; however, the year of publication is sufficiently earlier than the effective U.S. filing date and any foreign priority date so that the particular month of publication is not in issue.).

Dorfman et al., Reactivity of the Hydroxyl Radical in Aqueous Solutions. National Bureau of Standards. Report No. NSRDS—NBS 46, 76 pages, (Jun. 1973).

Fadeel et al., Big wheel keeps on turning: apoptosome regulation and its role in chemoresistance. Cell Death Differ. Mar. 2008;15(3):443-52.

Gracer et al., Can the combination of localized "proliferative therapy" with "minor ozonated autohemotherapy" restore the natural healing process? Med Hypotheses. 2005;65(4):752-9.

Gu et al., Global investigation of p53-induced apoptosis through quantitative proteomic profiling using comparative amino acid-coded tagging. Mol Cell Proteomics. Oct. 2004;3(10):998-1008 (published online Jul. 28, 2004).

Hochreiter-Hufford et al., Clearing the dead: apoptotic cell sensing, recognition, engulfment, and digestion. Cold Spring Harb Perspect Biol. Jan. 1, 2013;5(1):a008748, 20 pages.

Isermann et al., Nuclear mechanics and mechanotransduction in health and disease. Curr Biol. Dec. 16, 2013;23(24):R1113-21.

Jiang et al., Hemodynamic disturbed flow induces differential DNA methylation of endothelial Kruppel-Like Factor 4 promoter in vitro and in vivo. Circ Res. Jun. 20, 2014;115(1):32-43.

Jufri et al., Mechanical stretch: physiological and pathological implications for human vascular endothelial cells. Vascular Cell. Sep. 18, 2015; 7(8):1-12.

Linton et al., Macrophage Apoptosis and Efferocytosis in the Pathogenesis of Atherosclerosis. Circ J. Oct. 25, 2016;80(11):2259-2268.

Merrill, Rheology of Blood. Physiological Reviews. Oct. 1969;49(4):863-88.

Saas et al., Concise Review: Apoptotic Cell-Based Therapies-Rationale, Preclinical Results and Future Clinical Developments. Cells. Mar. 28, 2016;34:1464-73.

Seneviratne et al., Low shear stress induces M1 macrophage polarization in murine thin-cap atherosclerotic plaques. J Mol Cell Cardiol. Dec. 2015;89(Pt B):168-72 (available online Oct. 30, 2015).

Stroud et al., Linker of nucleoskeleton and cytoskeleton complex proteins in cardiac structure, function, and disease. Circ Res. Jan. 31, 2014;114(3):538-48.

Sun et al., Mixed lineage kinase domain-like protein mediates necrosis signaling downstream of RIP3 kinase. Cell. Jan. 20, 2012;148(1-2):213-27.

Tamiello et al., Heading in the Right Direction: Understanding Cellular Orientation Responses to Complex Biophysical Environments. Cellular and Molecular Bioengineering. Mar. 2016;9(1):12-37.

Tesoriere et al., Oxysterol mixture in hypercholesterolemia-relevant proportion causes oxidative stress-dependent eryptosis. Cell Physiol Biochem. Sep. 8, 2014;34(4):1075-89.

Vanden Berghe et al., Molecular crosstalk between apoptosis, necroptosis, and survival signaling. Mol Cell Oncol. Apr. 8, 2015;2(4):e975093, 13 pages.

Victorin et al., Review of the genotoxicity of ozone. Mutat Res. Sep. 1992;277(3):221-38.

Vota et al., Differential erythropoietin action upon cells induced to eryptosis by different agents. Cell Biochem Biophys. Mar. 2013;65(2):145-57 (available online Aug. 18, 2012).

Wang et al., Mixed lineage kinase domain-like protein MLKL causes necrotic membrane disruption upon phosphorylation by RIP3. Mol Cell. Apr. 10, 2014;54(1):133-146.

Wang et al., Unc5D regulates p53-dependent apoptosis in neuroblastoma cells. Mol Med Rep. Jun. 2014;9(6):2411-6.

Weddell et al., Hemodynamic analysis in an idealized artery tree: differences in wall shear stress between Newtonian and non-Newtonian blood models. PLoS One. Apr. 21, 2015;10(4):e0124575, 23 pages.

(56)     References Cited

OTHER PUBLICATIONS

Zhang et al., RIP3, an energy metabolism regulator that switches TNF-induced cell death from apoptosis to necrosis. Science. Jul. 17, 2009;325(5938):332-6.
Australian Office Action for Application No. 2017312194, dated Aug. 2, 2023, 5 pages.
Canadian Office Action for Application No. 3,073,413, dated Jul. 27, 2023, 5 pages.
European Office Action for Application No. 17842248.1, dated Mar. 16, 2020, 10 pages.
European Office Action for Application No. 17842248.1, dated Mar. 1, 2023, 10 pages.
Indian Office Action for Application No. 201947010428, dated Feb. 3, 2023, 7 pages.
International Search Report and Written Opinion for Application No. PCT/US2017/047690, dated Oct. 24, 2017, 12 pages.
Chinese Office Action for Application No. 201780064691.3, dated Mar. 27, 2024 with English Translation, 19 pages.

* cited by examiner

GAS TREATMENT DELIVERY SYSTEMS AND METHODS

RELATED APPLICATIONS

This application is a continuation of U.S. patent application Ser. No. 16/279,476, filed Feb. 19, 2019, now U.S. Pat. No. 11,471,579, which is a continuation of International Patent Application No. PCT/US2017/047690, filed Aug. 18, 2017, which claims benefit of and priority to U.S. Provisional Application No. 62/377,122, filed Aug. 19, 2016, and U.S. Provisional Application No. 62/399,008, filed Sep. 23, 2016, each of which is incorporated by reference herein in its entirety.

TECHNICAL FIELD

The embodiments herein generally relate to gas treatment delivery apparatuses and systems (e.g., ozone treatment delivery systems) for treating a fluid (e.g., a biological liquid such as blood) and methods thereof and, more particularly, to gas treatment delivery apparatuses and systems having a rotating or oscillating contact member.

BACKGROUND

Historically ozone has been used as a disinfectant or sterilizing agent in a variety of applications. These include fluid-based technologies, such as purification of potable water, sterilization of fluids in the semi-conductor industry, disinfection of wastewater and sewage, and inactivation of pathogens in biological fluids. Ozone has also been used in the past as a topical medicinal treatment, as a systemic therapeutic, and as a treatment of various fluids that were subsequently used to treat a variety of diseases.

Some previous technologies were incapable of measuring and differentiating between the amount of ozone that was delivered and the amount of ozone actually absorbed and utilized, which meant that previous medicinal technologies for use in patients were incapable of measuring, reporting or differentiating the amount of ozone delivered from the amount that was actually absorbed and utilized. For example, some previous fluid treatment technologies employing ozone to treat a fluid including a biological liquid (e.g., blood), were incapable of measuring, reporting or differentiating the amount of ozone delivered from the amount that was actually absorbed by the fluid. This problem made regulatory approval of such technologies as a therapeutic unlikely.

Additionally, some gas-fluid contacting devices used in prior ozone delivery systems employed materials on ozone-contacting surfaces that were not ozone inert and, therefore, reacted with and absorbed ozone. This resulted in absorption of ozone by the materials making it impossible to determine the amount of ozone delivered to and absorbed by the fluid. Furthermore, ozone absorption by such materials likely caused oxidation and the subsequent release of contaminants or deleterious byproducts of oxidation into the fluid.

Many previous ozone treatment technologies delivered ozone to a fluid in a relatively inefficient manner or had a relatively poor mass transfer efficiency of gas to fluids, requiring long gas-phase exposure times to deliver a desired absorbed dose to a fluid. A further shortcoming in some ozone delivery systems for treating a biological fluid is significant variability in the fluid product that is output from the ozone delivery system, including, for example, variations in fluid ozone concentration or variations in total absorbed dose of ozone from one fluid sample to the next fluid sample. Further many prior ozone delivery systems for treating biological liquids have limited operating and parameter flexibilities, limiting the ability to increase efficiency operation of the system. Another shortcoming in prior ozone delivery systems is that the control of the precision of absorption of ozone by the biological fluid is less than desirable, and the systems are not able to precisely control the target absorption during all three phases of ozone absorption, which include including the initial filling and/or charging of the space containing fluid with ozone, the treatment period, and the emptying or purging of ozone.

Therefore, there exists a need for ozone delivery systems and methods that more efficiently deliver ozone to fluid, deliver a desired dose faster than current approaches, result in less variability in product output, employ greater operating and parameter flexibility, and/or improve control of the precision of absorption of ozone and output.

SUMMARY

In one aspect, provided herein is an apparatus for delivering an absorbed-dose of a gaseous activating agent to a fluid comprising a biological liquid and/or cells, the apparatus comprising a) a gas-fluid contact device configured to controllably rotate or oscillate a contact member, the contact member configured to receive the fluid and to have an interior surface in contact with the received fluid; b) an inlet line configured to receive a gas comprising the activating agent or consisting of the activating agent from a gas source for delivery to the contact member; c) an outlet line for outputting gas from the contact member; and d) a control system configured to control one or more of rotation or oscillation of the contact member by the gas-fluid contact device, a flow rate of gas into the contact member, and a composition of gas flowing into the contact member.

In some embodiments, the apparatus further comprises one or more first sensors for analyzing a composition of the gas from the gas source to be delivered to the gas-fluid contact device; and one or more second sensors for analyzing a composition of the gas output from the gas-fluid contact device.

In some embodiments, the apparatus further comprises an input gas analyzer including the one or more first sensors; and an output gas analyzer including the one or more second sensors.

In some embodiments, the control system is further configured to determine a rate of gaseous activating agent absorption by the fluid based on a composition of the gas delivered to the gas-fluid contact device, a composition of the gas output from gas-fluid contact device, and a rate of flow of gas through the gas-fluid contact device.

In some embodiments, the control system is further configured to alter a composition of the gas delivered to the gas-fluid contact device or a flow rate of the gas delivered to the gas-fluid contact device based, at least in part, on the determined rate of gaseous activating agent absorption by the fluid. In some embodiments, the control system is further configured to alter a rotation rate or an oscillation rate of the contact member based, at least in part, on the determined rate of gaseous activating agent absorption by the fluid.

In some embodiments, the control system is further configured to determine a total amount of gaseous activating agent absorbed by the fluid during rotation or oscillation of the contact member. In some embodiments, the total amount of gaseous activating agent absorbed by the fluid is determined based, at least in part, on a composition of the gas delivered to the gas-fluid contact device over time, a composition of the gas output from of the gas-fluid contact device over time, and a rate of flow of gas through the gas-fluid contact device. In some embodiments, the control system is further configured to continuously or periodically determine a total amount of gaseous activating agent absorbed by the fluid during rotation or oscillation of the contact member. In some embodiments, the control system is further configured to cease delivering the gas comprising or consisting of the gaseous activating agent to the contact member based, at least in part, on the determination of the total amount of gaseous activating agent absorbed by the fluid. In some embodiments, the control system is further configured to deliver a non-reactive purge gas to the contact member based, at least in part, on the determination of the total amount of gaseous activating agent absorbed by the fluid In some embodiments, the control system is further configured to determine an estimate of a total gaseous activating agent contact time required to achieve absorption of a total pre-specified amount of the gaseous activating agent based, at least in part, on the determined rate of absorption of the gaseous activating agent by the fluid. In some embodiments, the control system is further configured adjust one or more of the rotation or oscillation rate, a rate of gas flow into the contact member, and a composition of the gas flowing into the contact member based on the estimate of the total gaseous activating agent contact time required to achieve absorption of the total pre-specified amount of the gaseous activating agent. In some embodiments, the one or more adjustments are selected to change the estimate of the total gaseous activating agent contact time to fall within a desired range.

In some embodiments, the control system is further configured to control a total amount of the gaseous activating agent absorbed by the fluid.

In some embodiments, the control system is further configured to control the apparatus to obtain a pre-specified amount of gaseous activating agent absorbed by the fluid. In some embodiments, the control system is further configured to control the apparatus to obtain the pre-specified amount of the gaseous activating agent absorbed by the fluid within a pre-specified total gaseous activating agent exposure time.

In some embodiments, the apparatus is configured such that rotation or oscillation of the contact member results in a thin film of the fluid on at least a portion of the interior surface of the contact member.

In some embodiments, the gas-fluid contact device further comprises one or more rollers configured to contact an outer surface of the contact member to drive rotation or oscillation of the contact member, at least one of the one or more rollers driven by a motor. In some embodiments, the outer surface of the contact member has a substantially circular cross-section.

In some embodiments, the apparatus is configured to enable at least a portion of the gas-fluid contact device that engages the contact member to be rotatably or pivotably tilted to facilitate removal of the fluid from the contact member via gravity.

In some embodiments, the apparatus includes a pivotable joint enabling the portion of the gas-fluid contact device that engages the contact member to be tilted relative to another portion of the apparatus to facilitate removal of the fluid from the contact member via gravity.

In some embodiments, the gas-fluid contact device comprises the contact member. In some embodiments, the gas-fluid contact device further comprises a fluid inlet for delivering the fluid into to the contact member. In some embodiments, the fluid inlet is also configured to function as a fluid outlet for removal of the fluid from the contact member. In some embodiments, the gas-fluid contact device further comprises a fluid outlet for removal of the fluid from the contact member.

In some embodiments, the apparatus further comprises a gas source. In some embodiments, the gas source comprises a gas generator that manufactures the gas or a container prefilled with a manufactured or formulated gas. In some embodiments, the gas generator includes an ozone generator. In some embodiments, the gaseous activating agent comprises ozone and the gas from the gas source for delivery to the contact member comprises ozone or an ozone/oxygen admixture. In some embodiments, the apparatus further comprises an ozone destroyer that receives gas output from the gas-fluid contact device.

In some embodiments, the contact member is a container. In some embodiments, the container is a single-use or disposable container. In some embodiments, the gas-fluid contact device is configured to releasably engage the container. In some embodiments, the gas-fluid contact device is configured to releasably engage the container through a rotating joint. In some embodiments, the rotating joint is a single-use or disposable rotating joint.

In some embodiments, the fluid comprises blood. In some embodiments, the fluid comprises a blood component. In some embodiments, the fluid comprises biological cells.

In some embodiments, the fluid is viscoelastic.

In another aspect, provided herein is a system for delivering an absorbed-dose of gaseous activating agent to a fluid comprising a biological liquid or cells, the system comprising an apparatus described herein, and the contact member.

In some embodiments, the contact member is a single-use or disposable contact member.

In some embodiments, the system further comprises a rotating joint configured to sealably couple the contact member to the gas-fluid contact device. In some embodiments, the rotating joint is a single use or disposable rotating joint.

In some embodiments, the system further comprises a fluid inlet for delivering the fluid into the contact member. In some embodiments, the fluid inlet is also configured to function as a fluid outlet for removal of the fluid from the contact member. In some embodiments, the gas-fluid contact device further comprises a fluid outlet for removal of the fluid from the contact member.

In some embodiments, the contact member is a container.

In yet another aspect, provided herein is a method of treating a fluid comprising a biological liquid and/or cells with a gaseous activating agent, the method comprising delivering a measured quantity of the fluid to a contact member such that the fluid is in contact with an interior surface of the contact member; rotating or oscillating the contact member to form a thin layer of the fluid on at least a portion of the interior surface of the contact member; during the rotation or oscillation, delivering a gas comprising the gaseous activating agent or consisting of the gaseous activating agent to the contact member enabling the gaseous activating agent to interact with the thin layer of fluid; and continuing the rotation or oscillation until a desired total amount of the gaseous activating agent is absorbed by the fluid.

In some embodiments, the method further comprises determining a rate of absorption of the gaseous activating agent by the fluid during the rotation and oscillation.

In some embodiments, the method further comprises continuously or periodically determining a rate of absorption of the gaseous activating agent by the fluid during the rotation and oscillation.

In some embodiments, the method further comprises determining a total amount of the gaseous activating agent absorbed by the fluid during the rotation or oscillation. In some embodiments, the method further comprises continuously or periodically determining the total amount of the gaseous activating agent absorbed by the fluid during rotation or oscillation.

In some embodiments, the method further comprises adjusting a rate of delivery of the gas to the contact member during the rotating or oscillating. In some embodiments, the adjustment of the rate of delivery of the gas to the contact member is based, at least in part, on a determined rate of absorption of the gaseous activating agent by the fluid, on a determined total amount of the gaseous activating agent absorbed by the fluid, or on both. In some embodiments, the adjustment of the rate of delivery of the gas to the contact member modifies a total exposure time of the fluid to the gaseous phase activating agent required to reach the desired total amount of the gaseous activating agent absorbed by the fluid.

In some embodiments, the method further comprises adjusting the rate of rotation or oscillation. In some embodiments, the rate of rotation or oscillation is adjusted during the rotation or oscillation, and wherein the adjustment of the rate of rotation or oscillation is based, at least in part, on a determined rate of absorption of the gaseous activating agent by the fluid, on a determined total amount of the gaseous activating agent absorbed by the fluid, or on both. In some embodiments, the adjustment of the rate of the rate of rotation or oscillation modifies a total gaseous activating agent exposure time required to reach the desired total amount of gaseous activating agent absorbed by the fluid. In some embodiments, the adjustment of the rate of rotation or oscillation modifies a velocity of motion of the fluid. In some embodiments, the adjustment of the rate of rotation or oscillation modifies the viscosity of the fluid. In some embodiments, the adjustment of the rate of rotation or oscillation changes the thickness of the thin layer.

In some embodiments, the method further comprises determining an estimated total exposure time required to obtain the desired total absorption amount of the gas by the fluid, and based on the estimated total exposure time required, altering the estimated total exposure time required by adjusting one or more of: a rate of oscillation or rotation of the contact member, a rate of flow of gas into the contact member, and a concentration of gas flowing into the contact member.

In some embodiments, the rotation or oscillation causes adhesive pulling of the fluid by interaction with the moving interior surface of the contact member.

In some embodiments, the contact member is continuously rotated to form the thin layer of the fluid on at least the portion of the interior surface of the contact member.

In some embodiments, the method further comprises controlling absorption of the gas by the fluid to limit the total absorption to a pre-specified desired total amount.

In some embodiments, the method further comprises controlling the absorption rate of the gaseous activating agent by the fluid to limit the total gaseous activating agent exposure time required to obtain the desired total amount of gaseous activating agent absorbed by the fluid.

In some embodiments, the method further comprises modifying a viscosity of the fluid prior to delivering the measured quantity of the fluid to the contact member.

In some embodiments, the method further comprises modifying a viscosity of the fluid prior to rotating or oscillating the contact member to form the thin layer of the fluid on at least the portion of the interior surface of the contact member. In some embodiments, modifying the viscosity of the fluid comprises adding a non-reactive thinning solution to the fluid. In some embodiments, adding the non-reactive thinning solution to the fluid modifies the thixotropic sheer thinning behavior of the fluid.

In some embodiments, the rate of absorption of the gaseous activating agent by the fluid evolves over time during the rotation and oscillation of the contact member. In some embodiments, the rate of absorption of the gaseous activating agent by the fluid depends, at least in part, on the concentration of the gaseous activating agent in the gas delivered to the contact member, the mass ratios of the fluid and gas, and the rate of rotation or oscillation of the contact member. In some embodiments, the absorption rate of the gaseous activating agent is modified by modulating the thickness of the fluid film in relation to the gas flow rate.

In some embodiments, the activating agent is selected from the group consisting of an oxidizing agent, a nitrodizing/nitrating agent, an oxynitriding agent, an enzymatic inducing agent, and a pharmaceutical agent. In some embodiments, the activating agent comprises an oxidizing agent. In some embodiments, the oxidizing agent is selected from the group consisting of oxygen ($O_2$), ozone ($O_3$), reactive oxygen species (ROS) producing agents, carbon monoxide, nitric oxide, nitrousoxide, potassium nitrate, superoxide, singlet oxygen, hydrogen peroxide and other inorganic peroxides including Fenton's reagent, hydrogen disulfide, carbon dioxide, fluorine, chlorine, chlorate, perchlorate, and other analogous halogen compounds, hypochlorite and other hypohalite compounds including household bleach (NaClO), hexavalent chromium compounds including chromic and dichromic acids and chromium trioxide, pyridinium chlorochromate (PCC), and chromate/dichromate compounds, permanganate compounds including potassium permanganate, sodium perborate, sodium bismuthate, sulfuric acid, peroxydisulfuric acid, peroxymonosulfuric acid and xenon. In some embodiments, the oxidizing agent comprises ozone.

In some embodiments, treating the fluid with the gas activates the fluid.

In some embodiments, rotating or oscillating the contact member to form the thin layer of the fluid on at least the portion of the interior surface of the contact member and delivering the gas to the contact member enabling the gaseous activating agent to interact with the thin layer of fluid produces apoptotic cells (AC) or AC-like responding bodies. In some embodiments, the AC are selected from the group consisting of megakaryocytes, platelets, pyrenocytes, red blood cells, leukocyte white blood cells, endothelial cells, a responding blood fraction, and a derivative thereof. In some embodiments, the AC-like responding bodies are selected from the group consisting of or characterized by activated receptors; kinases; cell surface determinants; membrane proteins, membrane expressions, secretions, antigens, fragments, complements, CD molecules, cell surface signaling receptor, ligand, anti-microbial peptides, complement opsonins, integrins, extracellular matrix, microparticles and other extrudations, and adhesion molecules. In some embodiments, a production rate of AC is modulated by controlling an absorption rate of the activating agent by the fluid.

In some embodiments, the rotating or oscillating the contact member to form the thin layer of the fluid on at least the portion of the interior surface of the contact member and delivering the gas to the contact member enabling the gaseous activating agent to interact with the thin layer of fluid also produces necroptic cells. In some embodiments, a production ratio of AC to necroptoic cells is modulated by controlling the fluid thin-film thickness and the total time of exposure of the fluid to the gaseous activating agent. In some embodiments, a ratio of generated necroptic cells to generated AC cells is less than 0.5.

In some embodiments, the rotation or oscillation results in mechanotransduction of targets within the fluid generating mechanobiological responses in targets in the fluid. In some embodiments, the mechanotransduction is controlled by adjustments of the velocity of motion of the fluid and/or the viscosity of the fluid.

In some embodiments, the fluid comprises blood or a component of blood. In some embodiments, the blood was obtained from a patient. In some embodiments, the fluid is treated extracorporeally to produce dynamic control generated apoptotic cells (dcAC) autologously. In some embodiments, the treated fluid or a component of the treated fluid is reinfused by intravenous injection into the patient. In some embodiments, the blood is donor (allogenous) blood. In some embodiments, the fluid is treated extracorporeally to produce dynamic control generated apoptotic cells (dcAC).

In some embodiments, the method further comprises administering the treated fluid or a component of the treated fluid to a patient in need thereof. In some embodiments, the administration is intravenous, intra-arterial subcutaneous, intraperitoneal, intragluteal, intraabdominal, intracranial, intracerebroventricular, or spinal.

In some embodiments, the measured quantity of fluid is delivered to a container, and the container comprises the contact member. In some embodiments, the measured quantity of fluid delivered to the container occupies at least 8% of a volume of the container. In some embodiments, the measured quantity of fluid delivered to the container is between 8% percent and 35% percent of the volume of the container.

In some embodiments, the gas comprises ozone or an oxygen/ozone admixture.

In some embodiments, the method is implemented using an apparatus as described herein.

In some embodiments, the method is implemented using a system described herein.

In another aspect, provided herein is a method of treating or preventing a disease, disorder, pathology, or condition comprising administering an effective amount of an AC produced by an apparatus, a system, or a method as described herein to a subject. In some embodiments, the disease or disorder is selected from the group consisting of autoimmune diseases, autoimmune-like diseases, cardiovascular diseases, inheritable or genetic neurodegenerative diseases, metabolic diseases, immunometabolism and metabolic-like diseases, neural degenerative diseases, neurodevelopmental disorders, neuropsychiatric disorders, pathological pain, sepsis, septic shock and endotoxin-like diseases, and transplant immune rejection.

BRIEF DESCRIPTION OF DRAWINGS

The embodiments described herein and other features, advantages and disclosures contained herein, and the manner of attaining them, will become apparent and the present disclosure will be better understood by reference to the following description of various exemplary embodiments of the present disclosure taken in conjunction with the accompanying drawing, in which like elements, similar elements, or corresponding elements, are indicated using the same reference number.

DESCRIPTION

Figure 1:
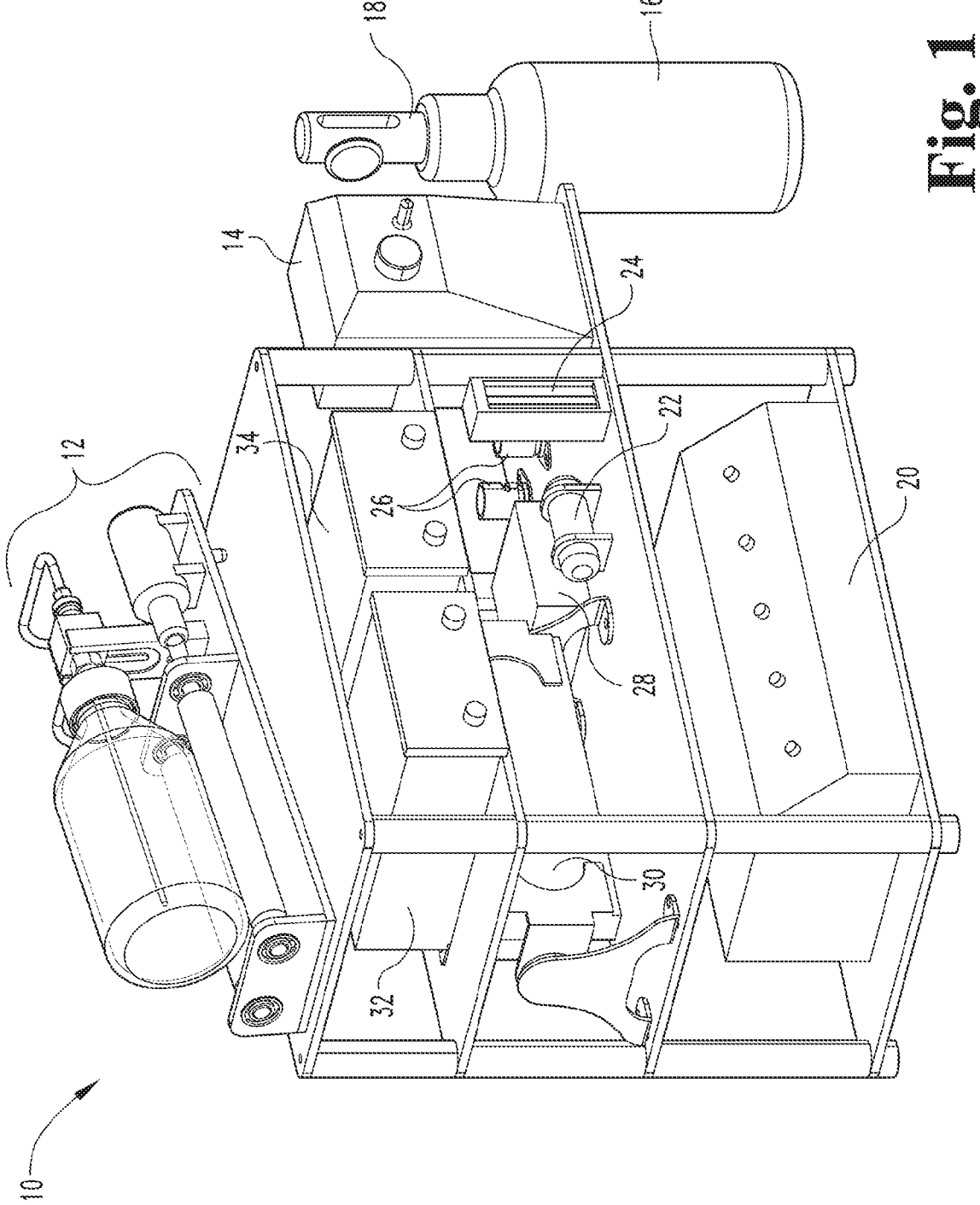
FIG. 1 depicts a perspective view of a gaseous activating agent delivery apparatus and system (e.g., an ozone delivery apparatus and system) according to an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The present application provides apparatuses and systems for delivering an absorbed-dose of a gaseous activating agent (e.g., ozone) to a fluid including a biological liquid and/or cells. As used herein, absorption of the gaseous activating agent by the fluid refers to any reaction between the gaseous activating agent and the fluid and/or cells or components of such. The apparatuses and systems include a gas-fluid contact device configured to controllably rotate or oscillate a contact member. The contact member is configured to receive the fluid and has an interior surface in contact with the received fluid. The apparatuses and systems also include an inlet line configured to receive a gas that is a gaseous activating agent or that includes a gaseous activating agent for delivery to the contact member. The apparatuses and systems also include an outlet line for outputting gas from the contact member. The apparatuses and systems also include a control system where the control system is configured to control one or more of the following: rotation or oscillation of the contact member by the gas-fluid contact device, a flow rate of gas into the contact member, and a composition of gas flowing into the contact member.

As the contact member is rolled or oscillated, a thin layer of the fluid is formed on at least a portion of the interior surface of the contact member. The relatively large surface area of the thin layer of fluid, as compared to the surface area of a thicker deposit of fluid that is not subject to rotation or oscillation, increases the mass transfer coefficient between the gas and the fluid. Further, the rotation and oscillation of the contact member continuously mixes and refreshes the fluid in the thin layer of fluid to enhance mass transfer and promote more uniform exposure of different portions of the fluid to the gas.

In some embodiments the apparatus or system includes one or more sensors, which may be included in an input gas analyzer, for analyzing a composition of the gas from the gas source to be delivered to the gas-fluid contact device, and one or more sensors, which may be included in an output gas analyzer, for analyzing a composition of gas output from the gas-fluid contact device. In some embodiments, the control system is further configured to use information from the sensors and/or input gas analyzer and output gas analyzer to accurately determine a rate of absorption of the active agent by the fluid and/or an amount of absorption of the active agent by the fluid. In some embodiments, the control system is further configured to determine a total amount (e.g., a total mass) of active agent absorbed by the fluid. In some embodiments, the control system is further configured to continuously or periodically determine a total amount of gaseous active agent absorbed by the fluid. In some embodiments, the control system is configured to determine when to cease flow of the active agent into the contact member based, at least in part, on a determined total amount of gaseous active agent absorbed by the fluid. In some embodiments, the control system is configured to determine when to introduce a non-reactive purge gas into the contact member based, at least in part, on a determined total amount of gaseous active agent absorbed by the fluid.

In some embodiments, the contact member is a container. In other embodiments, the contact member may have another configuration, such as a rotatable conduit (e.g., having a cylindrical tube shape). In some embodiments, the contact member couples with the gas-fluid contact device through a rotating joint. In some embodiments, the contact member and the rotating joint are single use or disposable.

In some embodiments, surfaces of components of the system and apparatus that are exposed to the gas downstream of the input analyzer and upstream of the output analyzer are inert or non-reactive to the gaseous activating agent (e.g., nonreactive to ozone).

In some embodiments, the gas-fluid contact device uses a motor driven roller to rotate or oscillate the contact member (e.g., the container) that rests on rollers. In other embodiments, a rotation or oscillation of the contact member may be directly driven by a motor or motor-driven component instead of relying on frictional contact with roller (e.g., by having a motor driven component engage the contact member).

Some embodiments provide a rotatable joint configured to engage a contact member, configured to deliver an input gas, and an input fluid to the contact member, and configured for draining a treated fluid from the contact member.

Some embodiments of the present disclosure provide several advantages compared to other approaches in the art that have been utilized. Some embodiments of a gaseous activating agent delivery system may deliver an activating agent (e.g., ozone) to fluid more efficiently than current approaches for delivery of ozone to fluid. For example, in some embodiments, the rotation or oscillation of the contact member improves mass transfer between the gas and the fluid and promotes a more uniform distribution of the absorbed activating agent in the fluid, as described above. Some embodiments may deliver of the gaseous activating agent (e.g., ozone) to fluid faster than current approaches. Another advantage of some embodiments is that the resulting treated fluid has limited variability, and in many instances no significant variability. Specifically, in some embodiments, there are only limited variations in concentration of the activating agent in the output treated fluids. An advantage of some embodiments of a gaseous activating agent delivery system is that the system and process of utilizing the system has improved operating and parameter flexibility compared to current approaches based on the ability to provide control through rotation or oscillation rates, which modifies multiple different parameters of a viscoelastic fluid and can be used to modify properties of the thin layer of fluid formed on the interior surface of the contact member. In some embodiments, the gaseous activating agent delivery system (e.g., ozone delivery system) is able to control the target absorption better than current approaches for ozone delivery to a fluid. In some embodiments, The gaseous activating agent delivery system can efficiently control all three phases of gaseous activating agent absorption, including the initial charging of fluid with activating agent, the treatment period, and the emptying or purging of the activating agent.

Figure 2:
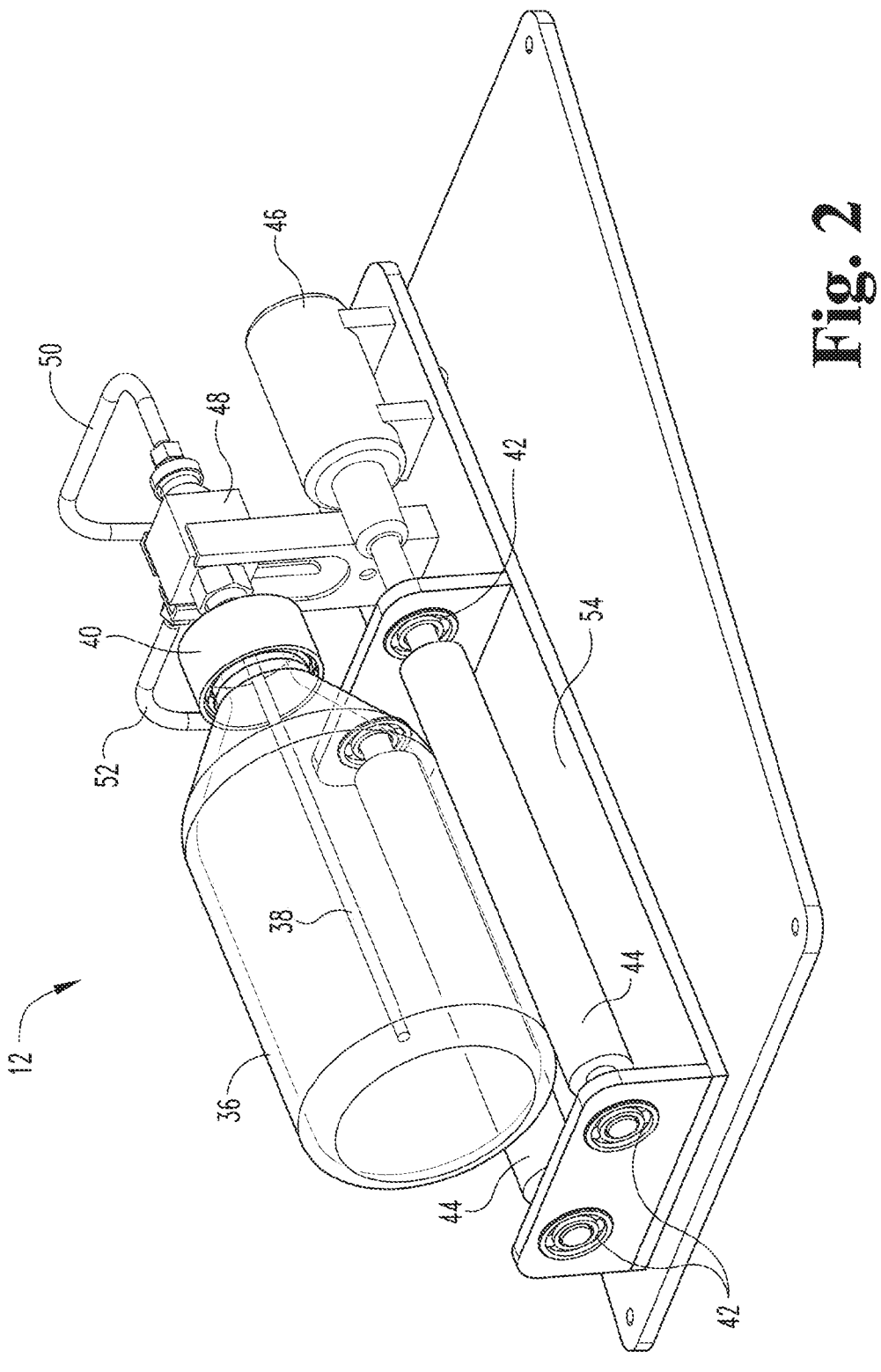
FIG. 2 depicts a perspective view of a contact device of the gaseous activating agent delivery apparatus and a contact member (e.g., a container) connected with the contact device via a permanent rotating joint according to an embodiment of the present disclosure.
Figure 3:
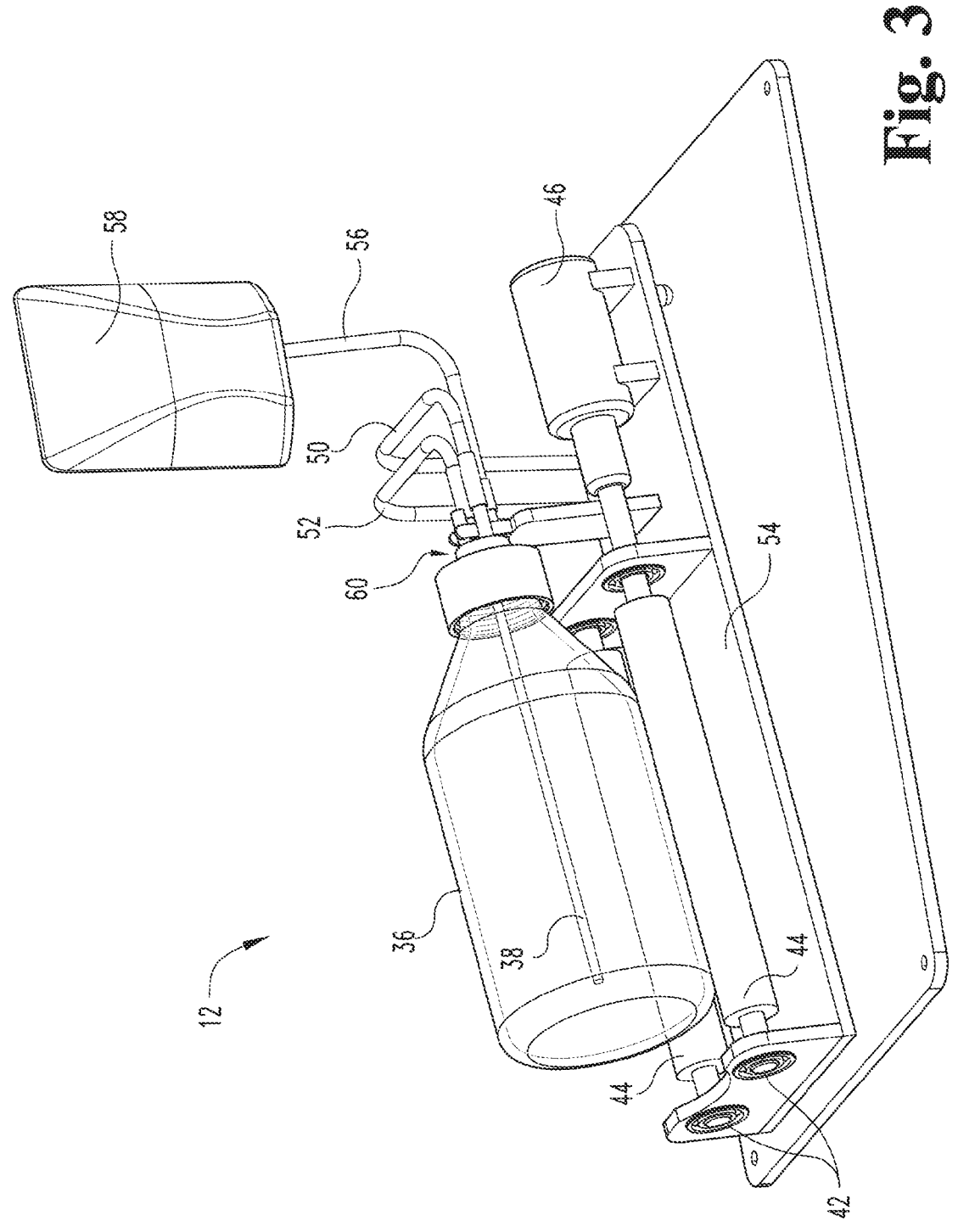
FIG. 3 depicts a perspective view of a contact device of a gaseous activating agent delivery system, a contact member connected with the contact device via a rotating joint (e.g., a disposable rotating joint), a reservoir holding fluid to be delivered to the contact member, and a fluid inlet port according to an embodiment of the present disclosure.

FIG. 1 illustrates a gaseous activating agent delivery apparatus and system 10 formed in accordance with an embodiment of the present disclosure. The apparatus and system 10 are configured for delivery an absorbed-dose of a gaseous activating agent to a fluid including a biological liquid and/or cells. In some embodiments, the gaseous activating agent delivery apparatus and system 10 is an ozone delivery apparatus and system. The gaseous activating agent delivery apparatus and system 10 includes a gas-fluid contact device 12, which is also referred to herein as a "contact device." FIGS. 2 and 3 illustrate an embodiment of the contact device 12. The contact device 12 is configured to controllably rotate or oscillate a contact member (e.g., container 36 of FIGS. 2, 3, 5, 6-8, and 12). The contact member (e.g., container 36) has an interior surface and is configured to receive the fluid where the received fluid contacts the interior surface of the contact member. The system 10 also includes an inlet line (e.g., gas inlet line 50) configured to receive a gas that is or that includes the gaseous activating agent for delivery to the contact member (e.g., container 36 or container 92) and an outlet line (e.g., gas outlet line 52) for outputting gas from the contact member (e.g., container 36 or container 92). The gaseous activating agent delivery apparatus also includes a control system configured to control rotation or oscillation of the contact member by the contact device 12, a flow rate of gas into the contact member, and/or a composition of gas flowing into the contact member.

In some embodiments, the apparatus or system 10 also includes a gas source. For example, turning again to FIG. 1, in some embodiments in which the gaseous activating agent is ozone, the apparatus has a gas source that includes an ozone generator 20 that receives oxygen from an oxygen tank 16 through an oxygen regulator 18. In some embodiments, the apparatus and system 10 include a flow meter 24 for measuring a flow of gas into the ozone generator 20.

Figure 13:
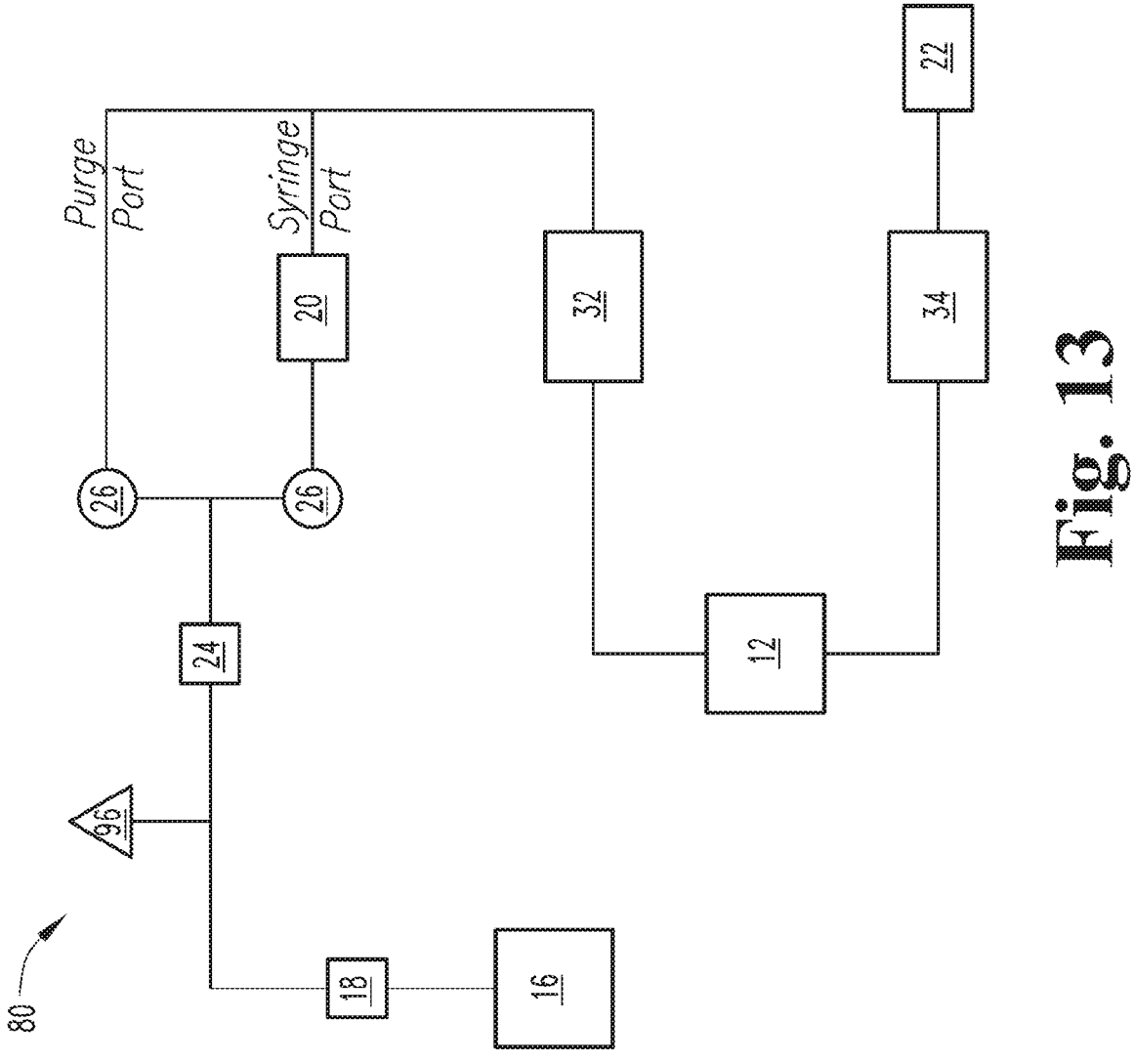
FIG. 13 schematically depicts a gaseous activating agent flow system according to an embodiment of the present disclosure.

In FIG. 1, tubing (not shown to enhance the clarity of the figures) is used to transport gas (e.g., oxygen ($O_2$) and ozone ($O_3$) and, in some embodiments, an admixture of oxygen/ozone) throughout the gaseous activating agent delivery system 10. In one embodiment, tubing extends from oxygen regulator 18 and connects to flow meter 24. In another embodiment, tubing extends from oxygen regulator 18 connects to a pressure relief valve 96 (as shown in FIG. 13) before extending from the pressure relief valve 96 and connecting to flow meter 24. In one embodiment, tubing extends from flow meter 24 and connects to ozone generator 20. In another embodiment, tubing extends from flow meter 24 and first connects to oxygen line pinch valves 26 and then extends from oxygen line pinch valves 26 and connects to ozone generator 20. In some embodiments employing ozone, the apparatus and system 10 may also include an ozone destroyer 22 for destroying ozone in a gas output from the contact member (e.g., container 36).

Although components of a gas source for providing ozone or an ozone/oxygen admixture are described above, one of skill in the art will appreciate that gas sources for providing other gaseous activating agents may employ similar components or other known components, as needed. In some embodiments, a gas source is not included in the system or apparatus and the system or apparatus merely receives a gas including an activating agent. In some embodiments, the gas source includes a container prefilled with a manufactured or formulated gas. In some embodiments, a gas in the prefilled container includes the gaseous activating agent. In some embodiments, a gas in the prefilled container includes a precursor to the gaseous activating agent.

In some embodiments, the apparatus and system include one or more sensors to sense a composition of gas delivered to the contact member (e.g., one or more first sensors included input analyzer 32) and one or more sensors to sense a composition of gas flowing out of the contact member (e.g., one or more second sensors included in output analyzer 34).

In some embodiments, tubing delivers gas from the gas source to the input analyzer 32 (e.g., the tubing extends from ozone generator 20 and connects to input analyzer 32). In some embodiments, tubing is also used to deliver gas from the input analyzer 32 to the contact device 12 (e.g., via gas inlet line 50 depicted in FIG. 2). In some embodiments, tubing extends from contact device 12 (e.g., the gas outlet line 52 depicted in FIG. 2) and connects to the output analyzer 34. In some embodiments employing ozone and an ozone destroyer 22, tubing extends from the output analyzer 34 and connects to the ozone destroyer 22.

In some embodiments, the apparatus and system 10 include a power supply 28, a motor controller 14, and one or more data acquisition modules 30. In some embodiments, power supply 28 is connected to and powers motor controller 14. In some embodiments, power supply 28 is also connected to oxygen line pinch valves 26, and ozone generator 20. In some embodiments, data acquisition modules 30 are connected to and/or in communication with input analyzer 32, output analyzer 34, a gas source (e.g., ozone generator 20), and contact device 12. Power supply 28 and data acquisition modules 30 may be coupled to other structures depending on the embodiment as one of ordinary skill in the art would understand in view of the present disclosure.

In some embodiments, the data acquisition modules 30 and the motor controller 14 are part of the control system. In some embodiments, the input analyzer 32 and output analyzer 34 are also part of the control system. In some embodiments, the ozone generator 30 is part of the control system. Other aspects and capabilities of the control system are described below following the description a computing device in FIG. 16.

In the embodiment described in FIG. 1 and further illustrated in FIG. 13, which schematically depicts a gas (e.g., oxygen/ozone) flow system 80, oxygen is released from oxygen tank 16 and flows through oxygen regulator 18. The oxygen then flows past a pressure relief valve 96 and through flow meter 24. The oxygen then flows until it approaches oxygen line pinch valves 26, including a normally closed solenoid and a normally open solenoid. The oxygen flows through the normally open solenoid of oxygen line pinch valves 26 and into ozone generator 20 where the oxygen is converted to ozone. As one of ordinary skill in the art would understand from the present disclosure, the conversion of oxygen to ozone may not produce pure ozone. That is, the ozone generator may release an oxygen/ozone admixture. Ozone or an oxygen/ozone admixture then flows from ozone generator 20 to input analyzer 32 and then to contact device 12. Output gas including ozone next flows from contact device 12 to output analyzer 34 before finally flowing to ozone destroyer 22. As one of ordinary skill in the art would appreciate from the present disclosure, a similar flow system could be employed for a different gaseous activating agent. In a flow system for a different gaseous activating agent, components such as oxygen tank 16, oxygen regulator 18, ozone generator 20 and ozone destroyer could be replaced with corresponding components for the different gaseous activating agent or omitted if not needed. Further, as described above, in some embodiments, the apparatus or system may not include a gas source, but gas including an activating agent may be supplied to the apparatus or system, in which case some elements of the gas flow system could be omitted.

In the embodiment described in FIG. 1, an external power source (not shown) provides power to power supply 28. Power supply 28 powers motor controller 14 and oxygen line pinch valves 26. In some embodiments, oxygen line pinch valves 26 are two solenoids, the first solenoid being a normally open solenoid and the second solenoid being a normally closed solenoid. Power supply 28 powers motor controller 14, motor 46 (as shown in FIG. 2), and ozone generator 20. Power supply 28 may power other structures in the gaseous active agent delivery apparatus and system 10 depending on the embodiment as one of ordinary skill in the art would understand in view of the present disclosure.

As generally used herein, the term apparatus includes components that are not single-use, not disposable, or not consumable. For example in FIG. 1, if the contact member (e.g., container 36) is single-use, disposable or consumable, the apparatus may not include the contact member. In some embodiments, where the oxygen tank and regulator are not built into the apparatus, but instead are replaceable, the apparatus may not include the oxygen tank 16 and regulator 18. As generally used herein, the term system refers to the apparatus and the associated single-use, disposable or consumable components. For example, in some embodiments, the system 10 includes the apparatus, and the contact member (e.g., container 36). In some embodiments, the system 10 includes the apparatus, the contact member (e.g., container 36) and a non-permanent rotating joint (e.g., rotating joint 60 of FIGS. 4A and 4B or rotating joint 61 of FIGS. 5A-5F), which may be a disposable or single-use rotating joint. In some embodiments, the system 10 includes the apparatus, the contact member (e.g., container 36), the rotating joint 60, and a tank of supply gas or precursor gas (e.g., oxygen tank 16) with a regulator 18.

FIG. 2 illustrates a contact device 12 in accordance with an embodiment of the present disclosure. The contact device 12 includes a mechanism to controllably rotate or oscillate the contact member (e.g., specifically container 36). In the embodiment depicted, the contact device 12 includes rollers 44 to rotate or oscillate container 36. In some embodiments, rollers 44 are coupled to an incline plane 54 via bearings 42 as depicted. In some embodiments, the contact device employs a motor 46 to drive rotation or oscillation of the contact member (e.g., container 36). For example, in the embodiment depicted, the contact device includes motor 46 attached to roller 44 via a bearings 42. In an embodiment, motor 46 is a variable speed motor. A contact member in the form of a container 36 is positioned on top of rollers 44 and is supported by rollers 44.

In the depicted embodiment, container 36 is rotated or oscillated by motor 46 through frictional contact between an outer surface of the container 36 and roller 44 driven by motor 46. However, in other embodiments, a contact member (e.g., a container) may be directly rotated or oscillated by a motor. For example, a motor may rotate or oscillate an element that engages the contact member (e.g., the container) instead of relying on frictional contact with elements like rollers to rotate or oscillate the contact member.

For embodiments employing rollers, those of ordinary skill will understand from the present disclosure that a contact member (e.g., a container) can have any configuration capable of being rotated or oscillated by rollers 44. Such a configuration may include but is not limited to a cylinder, a bottle, a tube, and a conical configuration. In some embodiments, a cross-section of an outer surface of the contact member is substantially circular. A material for the contact member may include, but is not limited to, glass, plastic, metal, and the like. In some embodiments, surfaces of the container that are exposed to the gas during use are formed of a material that is inert or nonreactive to the gaseous activating agent. In an embodiment, container 36 is a glass bottle. In some embodiments, surfaces of the container that are exposed to the gaseous activating agent during use are formed of a material that is inert or nonreactive to the gaseous activating agent. For example, in an embodiment, container 36 is made of borosilicate glass, which is inert to ozone. Other materials that can be employed that are nonreactive or inert to ozone include, but are not limited to, stainless steel, titanium, borosilicate, quartz, ceramic composites, PFA (copolymer of tetrafluoroethylene and perfluorinated vinyl ether from the perfluoroalkoxy group), and PTFE (polytetrafluoroethylene).

In view of the present disclosure, the skilled artisan will understand that the rollers 44 may comprise any material and have any configuration capable of supporting and controlling container 36 (e.g., providing sufficient frictional contact with the container and sufficient support) during oscillation or rotation. Such materials include, but are not limited to plastic, metal, mesh, fiber, rubber, combinations thereof, and the like.

In some embodiments, closure 40 is detachably attached to a permanent rotating joint 48. As used herein, the term "permanent rotating joint" refers to a rotating joint that is part of or incorporated into the contact device and is not replaced or removed from the contact device between treatments during ordinary use. However, the term "permanent rotating joint" does not mean or imply that the rotating joint could not be replaced or would not need to replaced due to damage, wear or reaching its expected lifetime. In such embodiments, the permanent rotating joint 48 would be considered part of the apparatus. In an embodiment, permanent rotating joint 48 is comprised of stainless steel, which is inert to ozone. In an embodiment, container 36 is screwed onto closure 40. In an embodiment, closure 40 comprises a container cap including a seal. In an embodiment, closure 40 comprises a bottle cap with a seal. In an embodiment, closure 40 is made of PTFE (polytetrafluoroethylene), which is inert to ozone.

In an embodiment, a gas inlet line 50 extends from input analyzer 32. In an embodiment, gas inlet line 50 is coupled to permanent rotating joint 48. In an embodiment, gas inlet tube 38 extends from gas inlet line 50 via permanent rotating joint 48 into container 36. In an embodiment, gas inlet tube 38 is comprised of stainless steel, which is inert to ozone. In an embodiment, a gas outlet line 52 extends outward from permanent rotating joint 48 towards output analyzer 34.

FIG. 3 illustrates a contact device 12 that engages with a container 36 via a rotating joint 60 having a different configuration in accordance with an embodiment of the present disclosure. In this configuration, rotating joint 60 is not permanent (e.g., is not built into or incorporated into the contact device) but is a separate component. In some embodiments, rotating joint 60 may be a disposable or single-use rotating joint. Some components of contact device 12 illustrated FIG. 2 may be used with the embodiment illustrated in FIG. 3. In an embodiment, a reservoir 58 containing fluid is suspended above the contact device 12. Reservoir 58 containing fluid is detachably attached to a fluid inlet port 56. In an embodiment, fluid inlet port 56 is coupled to a fluid inlet tube 70 and/or a fluid outlet tube 74 (as shown in FIG. 4) which is coupled to rotating joint 60 (as shown more clearly in FIGS. 4 and 5). In the embodiment illustrated in FIG. 3, rotating joint 60 is used instead of permanent rotating joint 48.

Fluid treated by the gaseous activating agent includes a biological liquid, including without limitation blood, blood-like or blood derived fraction, in a liquid or liquid-like flowable form (e.g. whole blood, buffy coat, filtered blood, blood isolate concentrations or any other fraction of blood containing cell bodies or formed particles including leukocytes, platelets, erythrocytes/RBCs and extracellular vesicles, or other human or animal derived blood-like cell containing fluid secretions) and/or a liquid including cells. In some embodiments, the biological liquid is a viscoelastic liquid. In some embodiments, the fluid including cells is a viscoelastic liquid.

In the embodiments illustrated in FIGS. 1-2, contact device 12 is configured to controllably rotate or oscillate the contact member (e.g., container 36) and infuse the fluid with ozone. In use, a measured quantity of fluid is delivered to container 36 where the fluid is in contact with an interior surface of container 26.

In some embodiments (e.g., see the embodiment shown in FIG. 2), the fluid is delivered to the container 36 before the container is positioned on or engaged with the contact device 12. Closure 40 is sealed to prevent the gaseous activating agent (e.g. ozone) from escaping container 36 and to prevent external air from entering container 36. Container 36 is placed on contact device 12, particularly on rollers 44. Permanent rotating joint 48 is used to allow gas inlet line 50 to inject gas into container 36 and gas outlet line 52 to expel the gas from container 36.

In some embodiments, the fluid is delivered to container 36 after the container is already positioned on or engaged with the contact device 12 (e.g., after the container 36 is positioned on the rollers) (e.g., see the embodiment shown in FIG. 3). In the embodiment depicted in FIG. 3, rotating joint 60 enables gas inlet line 50 to inject ozone into container 36 and gas outlet line 52 to expel gas from container 36. In some embodiments, the rotating joint 60 would not be considered part of the gaseous activating agent delivery apparatus, but would be considered part of the gaseous activating agent delivery system 10.

One feature of contact device 12 is that gas including or consisting of the gaseous activating agent is introduced to the fluid in container 36 as container 36 is rotated and/or oscillated by rollers 44 via motor 46. In an embodiment, the process of infusing the gaseous activating agent is performed in batch mode. In such an embodiment, an example would be placing 100 milliliters (mL) of fluid in a 1000 mL container and then infusing the fluid with the gaseous activating agent (e.g., ozone) for a determined amount of time or until a desired amount of the gaseous activating agent is absorbed by the fluid. After the desired measured amount of infusion is achieved, the gas including the activating agent is purged from the container and the fluid is removed from the container.

Figure 12:
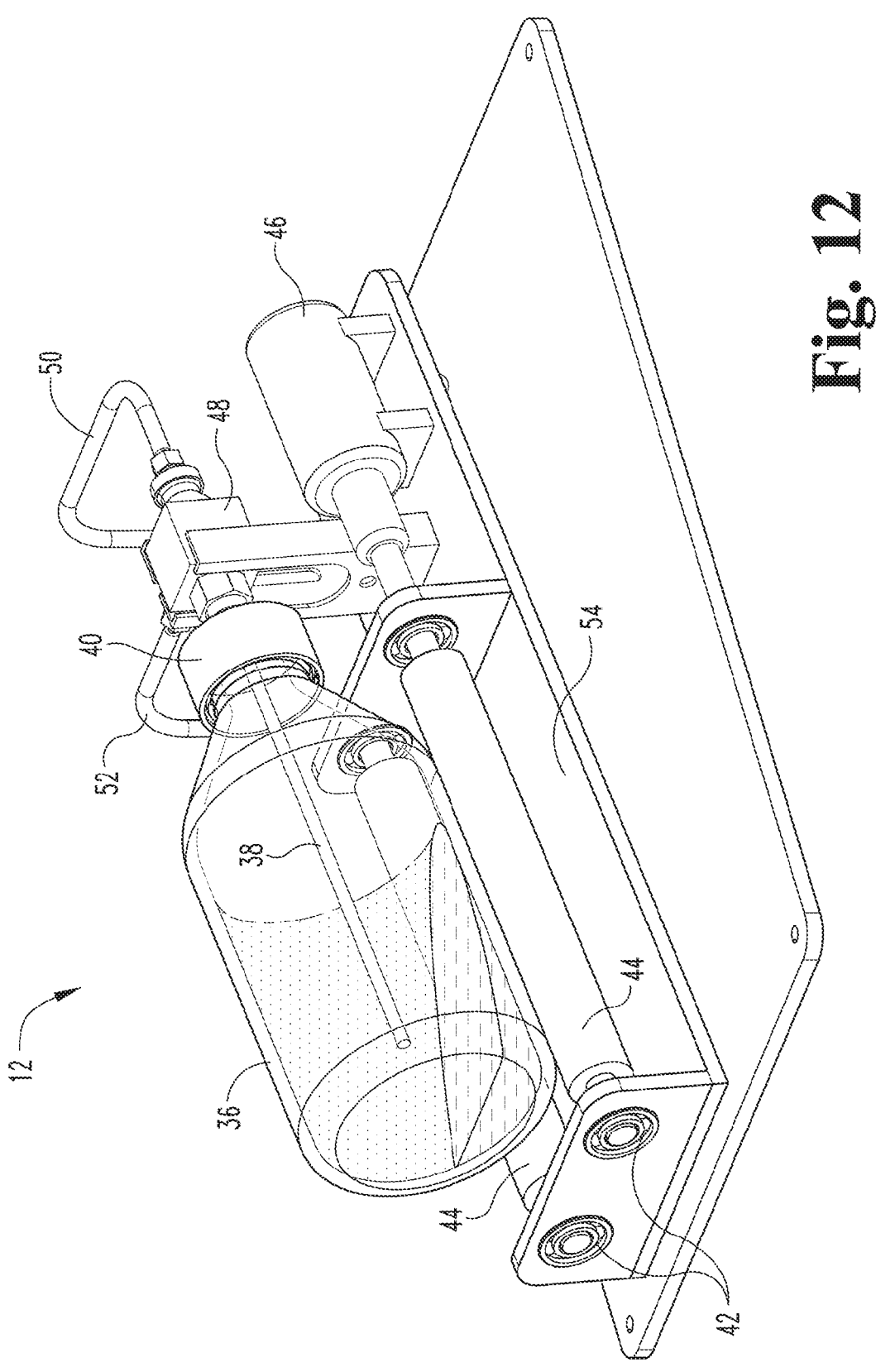
FIG. 12 depicts a perspective view of a contact device coupled to a contact member (e.g., a container) during rotation of the container and a thin layer of fluid formed on the surface of the container during rotation according to an embodiment of the present disclosure.

In some embodiments, motor 46 rotates and/or oscillates a roller 44, which causes container 36 to rotate and/or oscillate. As container 36 rotates and/or oscillates, a thin layer of fluid is formed on an interior surface of the container (e.g., on the inside wall of container 36) (see FIG. 12). Because the infusion of an gaseous activating agent (e.g., ozone) into the fluid occurs at the gas-fluid interface, infusion is more efficient for a given volume of fluid when the surface area of the fluid exposed to gas is larger. The creation of the thin layer of fluid increases the surface area of the fluid exposed to the gas, thereby increasing the efficiency of the infusion. As container 36 rotates and/or oscillates, a new thin layer of fluid is constantly being formed on the interior surface container 36. This constant formation of a thin layer of fluid on the inside wall of container 36 is one of the advantages of the present disclosure that makes contact device 12 very efficient at infusing ozone into fluid. Specifically, it mixes the portion of the fluid that has been infused at the surface with fluid away from the surface of the fluid and refreshes the surface of the thin layer to enhance infusion efficiency and provide greater uniformity of infusion throughout the fluid. The formation of the thin layer of fluid on the interior surface of container 36 is illustrated in FIG. 12.

Figure 6A:
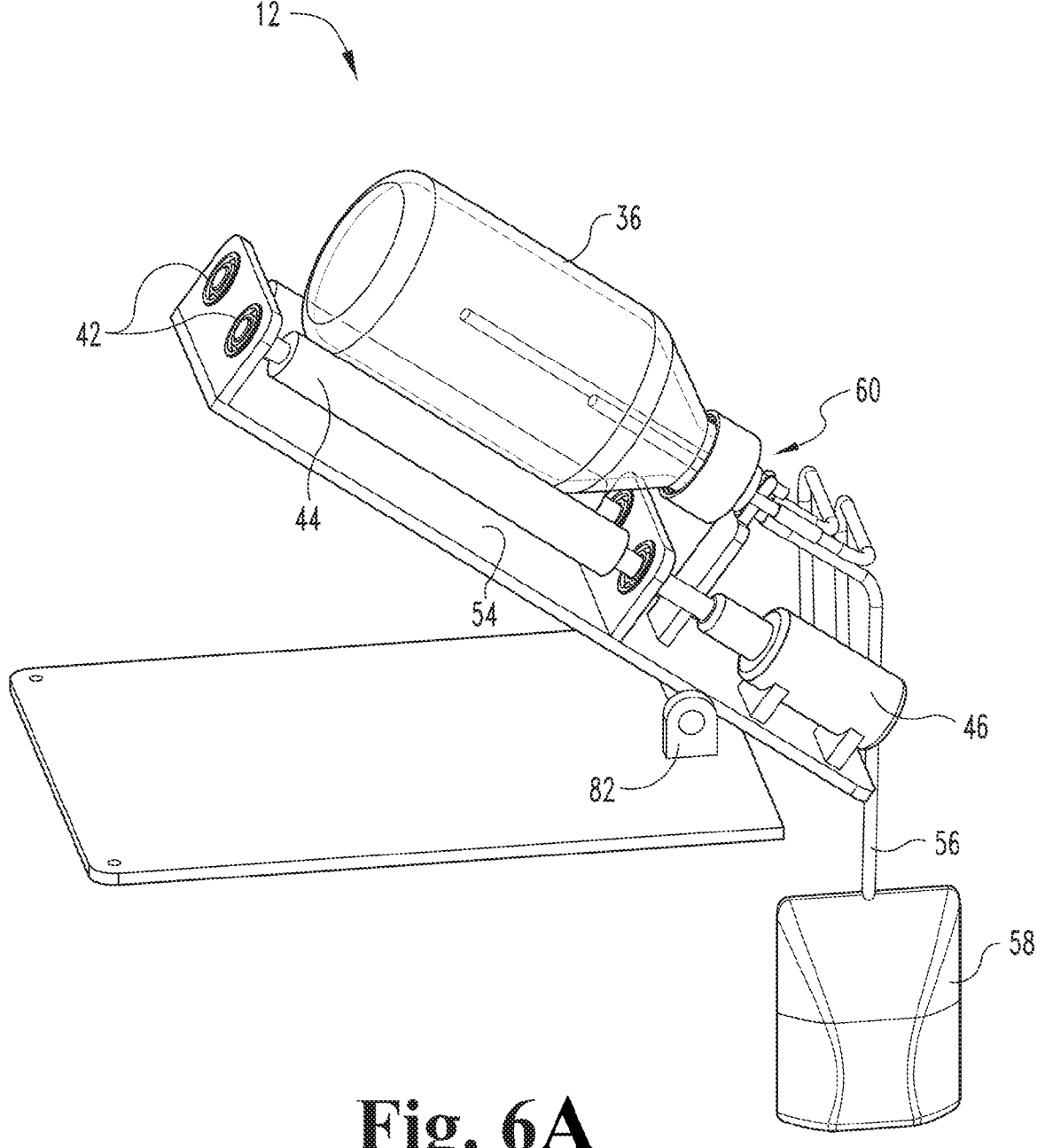
FIG. 6A depicts a perspective view of a contact device of a gaseous activating agent delivery apparatus pivoted upward about a pivot and a contact member (e.g., a container) pivoted upward to facilitate exit of the fluid from the contact member into a reservoir, where a fluid inlet port also functions as a fluid outlet port according to an embodiment of the present disclosure.

FIG. 3 depicts fluid in reservoir 58 being gravity fed into container 36 to be treated with the gaseous activating agent (e.g., ozone). After the fluid is infused with activating agent, the fluid can then be gravity fed back to the reservoir of fluid 58 as shown in FIG. 6A. In the embodiment depicted in FIG. 3, permanent rotating joint 48 is replaced with rotating joint 60, which is built into cap 64 (as shown in FIG. 4). Rotating joint 60 includes a fluid inlet tube 70, a fluid outlet tube 74, a gas inlet tube 38, and a gas outlet tube 76. In some embodiments, either fluid inlet tube 70 or fluid outlet tube 74 could be used for both inlet and outlet of the fluid from the container leaving the other to be used as a vent. In some embodiments where the fluid inlet tube 70 or fluid outlet tube 74 is used for both inlet and outlet of the fluid from the container, the other tube may be omitted. In some embodiments, a first reservoir 58 is connected to fluid inlet tube 70 and used to load fluid into the container 36, and a second reservoir (not shown) is connected to the fluid outlet tube 74 to receive treated fluid from the container 36. In such embodiments, the first reservoir 58 may be positioned higher than the container 36 and the second reservoir (not shown) may be positioned lower than the container 36. As shown in FIG. 4, silicone tubes or caps 72 may be used to cover ends of gas inlet tube 38, gas outlet tube 76, fluid inlet tube 70, and fluid outlet tube 74 of rotating joint 60 to prevent contamination prior to use.

In use, after removal of any protective tubes or caps 72, reservoir 58 containing fluid is attached to a fluid inlet port 56 via the rotating joint 60 (see FIG. 3). The fluid is gravity fed into the container 36. The container 36 is rotated and/or oscillated and a gas that is or includes gaseous activating agent (e.g., ozone) enters the container 36 until the desired level of infusion of the activating agent (e.g., ozone) into the fluid is achieved. In an embodiment, a pump (not shown) could be used to pump the activating agent-infused fluid back into the reservoir 58; however, in other embodiments, a second reservoir could be used to collect the treated fluid as described above. In other embodiments, the reservoir 58 is lowered to allow gravity to move the fluid back into the reservoir 58, as shown and described in greater detail below with respect to FIGS. 6A-6C.

Figure 4A:
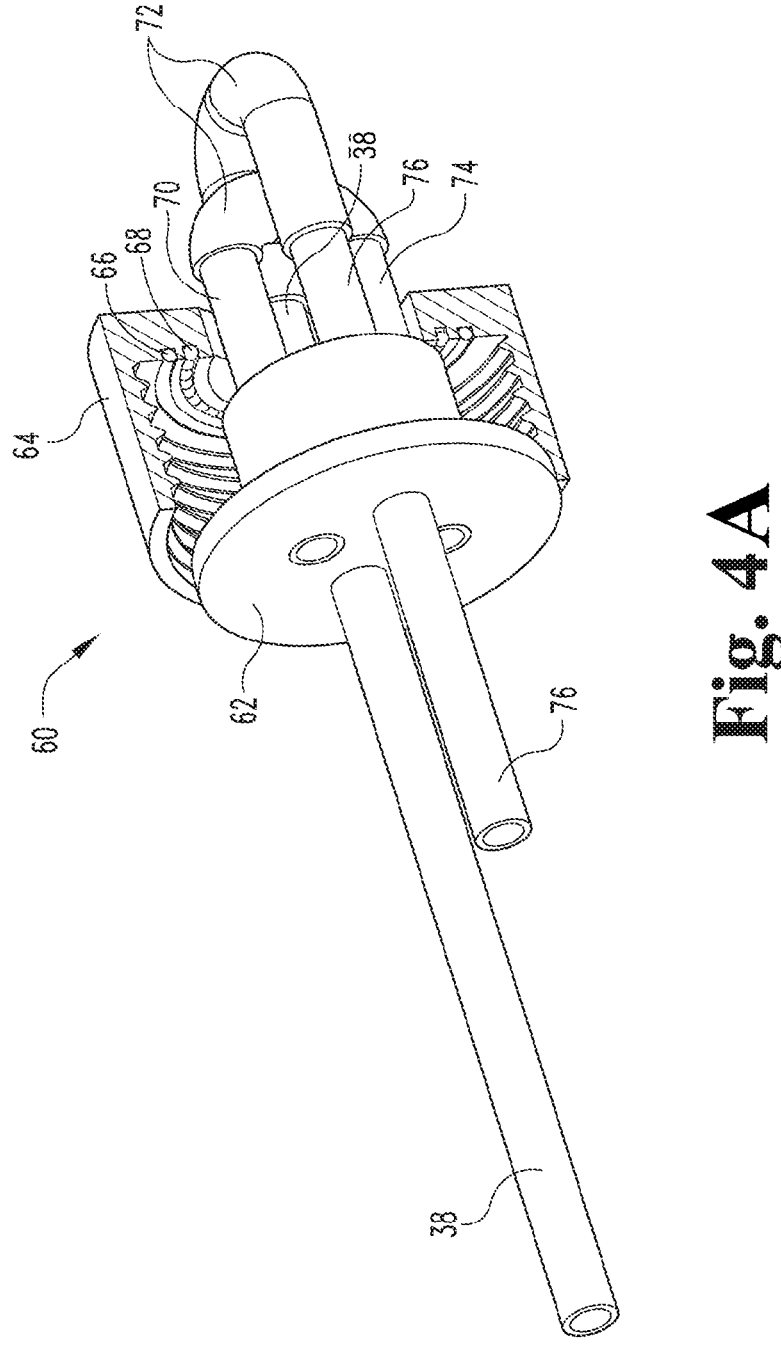
FIG. 4A depicts a perspective view of a rotating joint according to an embodiment of the present disclosure.
Figure 4B:
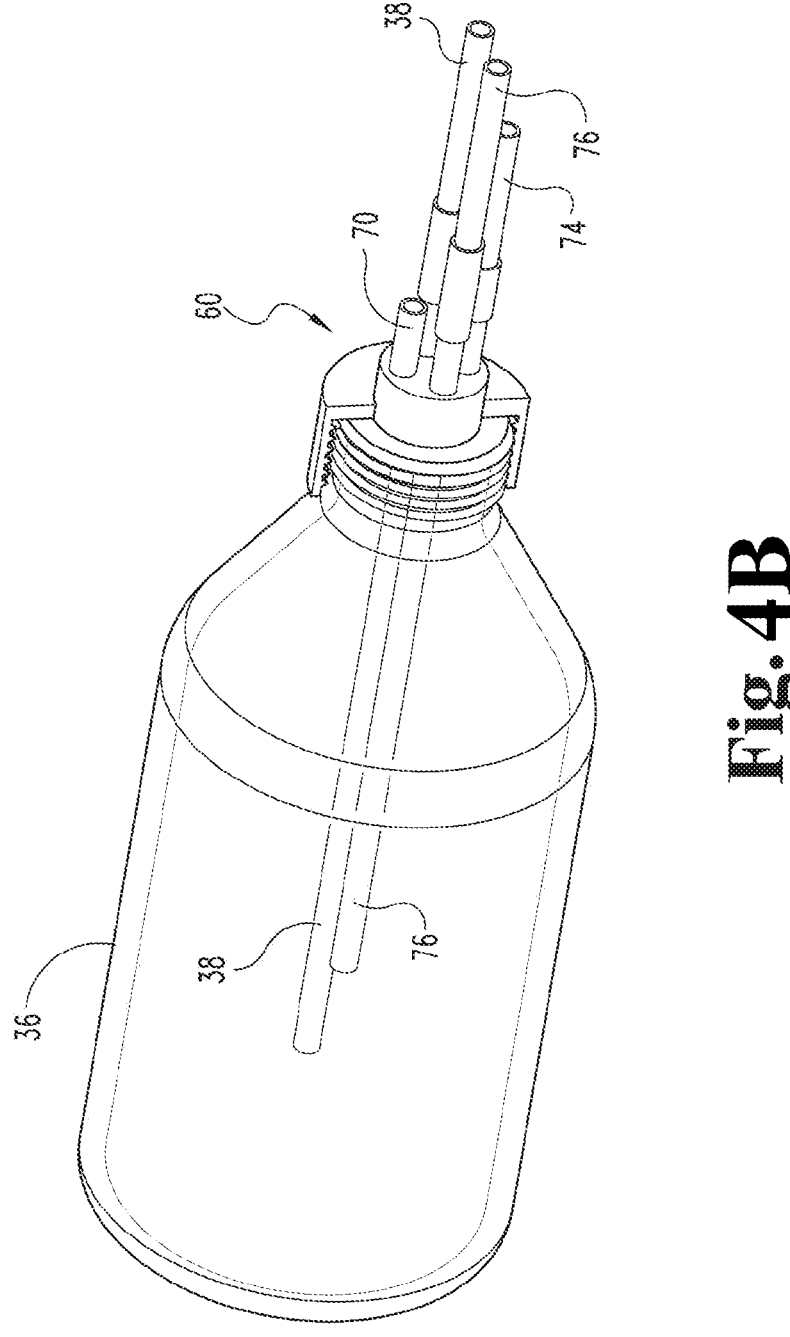
FIG. 4B depicts a perspective view of a contact member (e.g., a container) connected to the rotating joint of FIG. 4A.
Figure 5A:
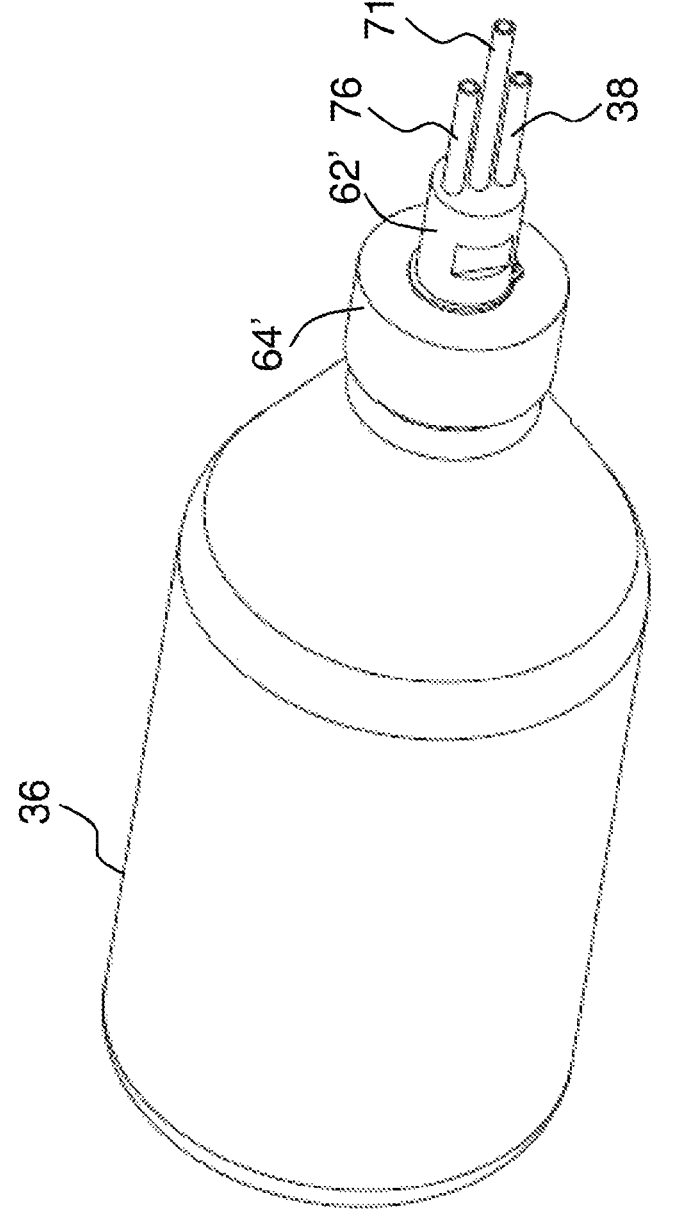
FIG. 5A depicts a perspective view of a rotating joint connected to a container according to another embodiment of the present disclosure.
Figure 5B:
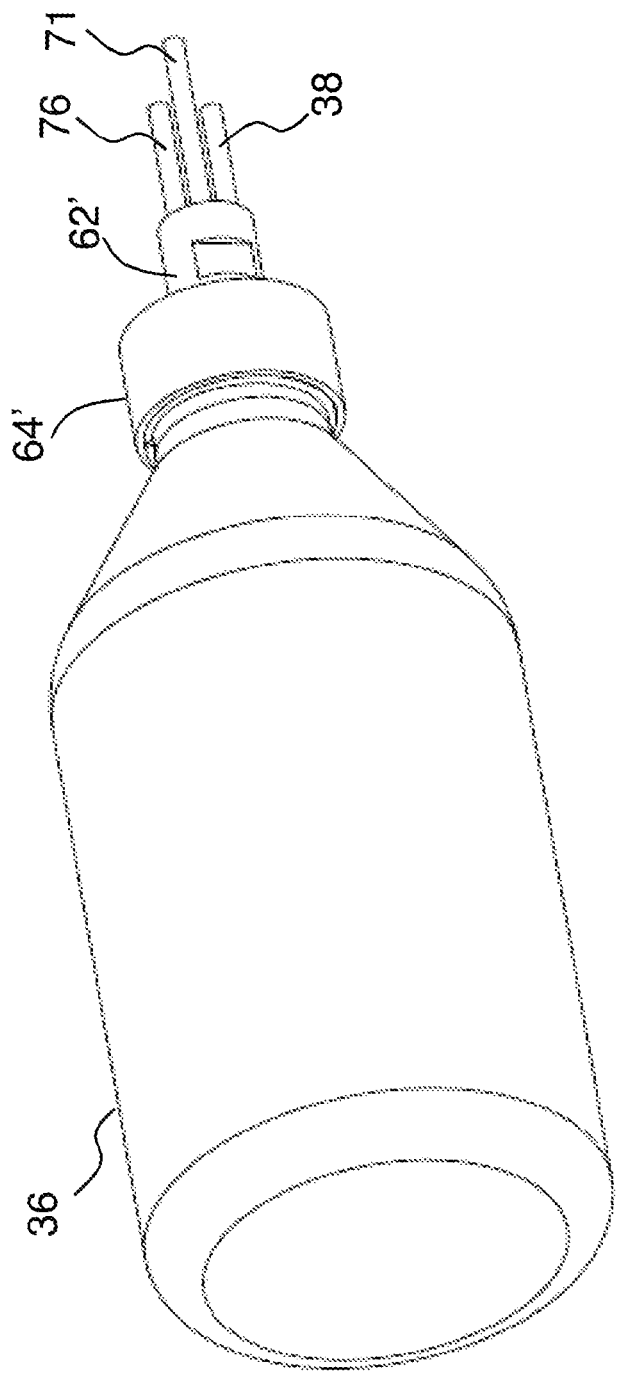
FIG. 5B depicts a different perspective view of the rotating joint and container of FIG. 5A.
Figures 5C, 5D:
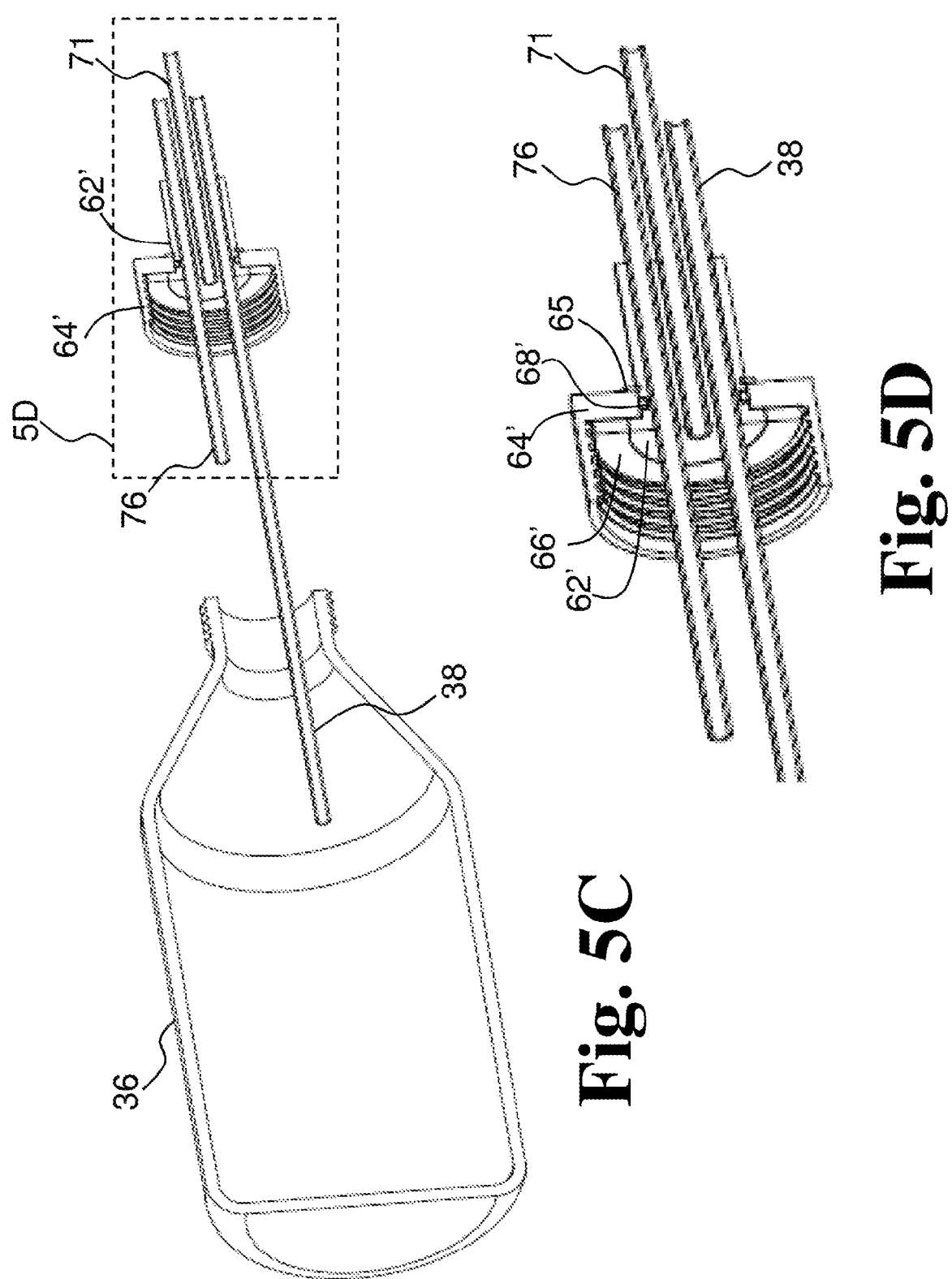
FIG. 5C depicts a perspective section view of the rotating joint and container of FIG. 5A.
FIG. 5D is a detail of the perspective section view of FIG. 5A.
Figure 5E:
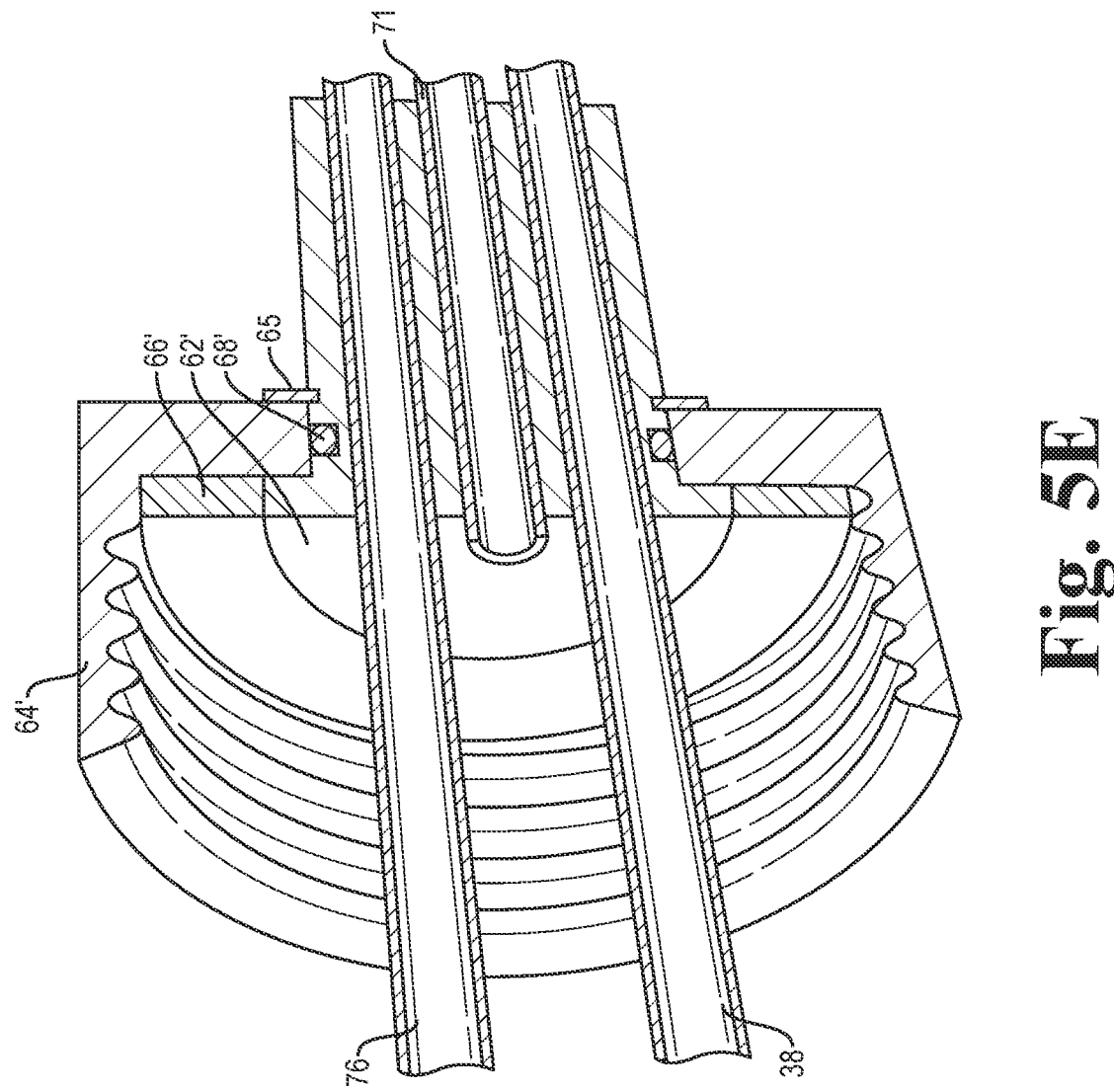
FIG. 5E is another detail of the perspective section view of FIG. 5A.
Figure 5F:
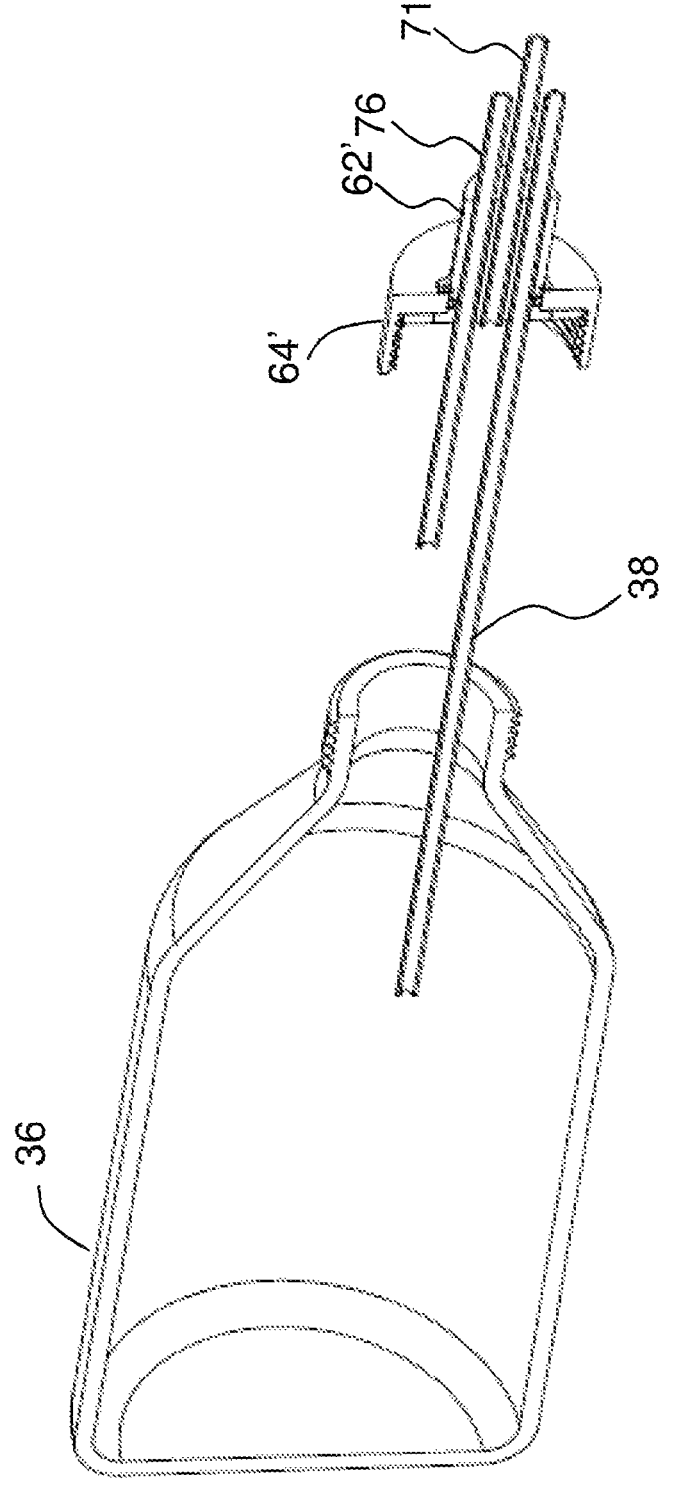
FIG. 5F depicts a different perspective section view of the disposable rotating joint and container of FIG. 5A.

FIGS. 4A and 4B illustrate a rotating joint 60 in accordance with the embodiment shown in FIG. 3 of the present disclosure. Rotating joint 60 includes a cap 64 and an insert 62 rotatably coupled to the cap 64. Insert 62 includes a side that faces toward an interior of the container during use and a side that faces away from the container during use. In some embodiments, rotating joint 60 also includes an O-ring 66 disposed in a recess of cap 64. In some embodiments, rotating joint 60 does not include O-ring 66, but includes a recess configured to receive an O-ring that is provided separately. In some embodiments, rotating joint 60 also includes ball bearings 68 disposed in a circular recess of cap 64.

In some embodiments, rotating joint 64 includes a gas inlet tube 38 that is built into insert 62, coupled with insert 62, part of insert 62, or integral with insert 62. Gas inlet tube 38 extends through insert 62 and away from the insert 62 toward a space that is interior to the container during use and also extends through the cap 64 and away from the insert 62 in an opposite direction.

In some embodiments, the rotating joint 64 includes a gas outlet tube 76 that is built into insert 62, coupled with insert 62, part of insert 62, or integral with insert 62. Gas outlet tube 76 extends through insert 62 and away from the insert 62 toward a space that is interior to the container during use, and also extends through the cap 64 and away from the insert 62 in an opposite direction.

In some embodiments, rotating joint 60 includes a fluid inlet tube 70 that is built into insert 62, coupled with insert 62, part of insert 62, or integral with insert 62. Fluid inlet tube 70 extends through insert 62 and away from the insert 62 toward a space that is interior to the container during use, and also extends through the cap 64 and away from the insert 62 in an opposite direction.

In some embodiments, rotating joint 60 includes a fluid outlet tube 74 that is built into insert 62, coupled with insert 62, part of insert 62, or integral with insert 62. Fluid outlet tube 74 extends through insert 62 and away from the insert 62 toward a space that is interior to the container during use, and also extends through the cap 64 and away from the insert 62 in an opposite direction.

In some embodiments, fluid inlet tube 70 or fluid outlet tube 74 is used as both an inlet for fluid into the contact member (e.g., container 36) and an outlet for output of treated fluid from the contact member (e.g., container 36), in which case the other tube may be used as a vent, sealed, or omitted.

In some embodiments, rotating joint 60 includes a vent (not shown) that is built into insert 62, coupled with insert 62, part of insert 62, or integral with insert 62.

In some embodiments, one or more of the gas inlet tube 38, gas outlet tube 76, fluid inlet tube 70, and fluid outlet tube 74 are parallel to each other.

As noted above, in some embodiments, silicone tubes 72 are employed to cap fluid inlet tube 70, fluid outlet tube 74, ozone outlet tube 76, and ozone inlet tube 38 to prevent contamination when the rotating joint 60 is not being used. In view of the present disclosure, those of ordinary skill in the art will understand that, in some embodiments, insert 62, cap 64, ball bearings 68, fluid inlet tube 70, fluid outlet tube 74, gas outlet tube 76, and gas inlet tube 38 may include any material that inert to one or more gaseous activating agents (e.g., ozone) and has suitable mechanical properties. Such materials include, but are not limited to, stainless steel, PTFE, and the like.

FIGS. 5A-5F depict another embodiment of a rotating joint 61, which may be a disposable rotating joint. Rotating joint 61 includes a rotating cap component 64' and a fixed cap component 62' that is rotatably coupled to rotating cap component 64'. In some embodiments, rotating cap component 64' has a base end that engages the container and an inlet/outlet end opposite the base end. In some embodiments, the inlet/outlet end of the rotating cap component 64' has an aperture and a portion of the fixed cap component 62' extends through the aperture and beyond the inlet/outlet end of the rotating cap component 64'. In some embodiments, rotating joint 61 includes ball bearings 68' disposed between rotating cap component 64' and fixed cap component 62' (see FIGS. 5E and 5F). In some embodiments, ball bearings 68' are disposed in a recess formed in fixed cap component 62'. In some embodiments, ball bearings 68' are disposed in the aperture of rotating cap component 64' between fixed cap component 62' and rotating cap component 64. Rotating joint 61 includes a gasket 66' (e.g., a silicone O-ring) that seals the rotating cap component 64' against the container 35 (see FIGS. 5E and 5F). In some embodiments, rotating joint 61 does not include gasket 66', but is configured to receive a gasket that is provided separately. In some embodiments, rotating joint 61 also includes a retaining member 65 (see FIGS. 5E and 5F). Rotating joint 61 includes a gas inlet tube 38 and a gas outlet tube 76. Where rotating joint 60 included a fluid inlet tube 70 and a separate fluid outlet tube 74, rotating joint 61 includes a fluid inlet and outlet tube 71, which is used to both deliver fluid to container 36 and to drain treated fluid from container 36. In some embodiments, a reservoir can be connected to fluid inlet and outlet tube 71 and fluid in the reservoir can be fed by gravity into container 36 when the reservoir is above container 36 and after treatment the same reservoir is positioned lower than the container 36 to gravity feed the treated fluid out of container 36 and into the reservoir as described with respect to FIGS. 6B and 6C below. In some embodiments, fluid inlet and outlet tube 71 extends along an axis of rotation rotating cap component 64'. In some embodiments, any or all of fluid inlet and outlet tube 71, gas inlet tube 38 and gas outlet tube 76 are coupled with, attached to, or integral with fixed cap component 62'.

FIG. 6A depicts a contact device 12 having a portion pivoted about pivot 82 in a decline position to facilitate draining of the fluid from the container 12 into the reservoir 58 in accordance with an embodiment. Reservoir 58 is suspended below the contact device 12 for draining of the container 36 via gravity. In some embodiments, reservoir 58 is detachably attached to a fluid inlet port 56. In some embodiments, fluid inlet port 58 is detachably attached to and/or coupled to rotating joint 60'. In some embodiments, fluid inlet port 56 is coupled to rotating joint 60' via the fluid inlet and outlet tube 71 (see FIGS. 5A to 5F).

In the embodiment illustrated in FIG. 6A, at least a portion of contact device 12 is pivoted about pivot 82 and fluid is gravity fed from container 36 into reservoir 58. In this embodiment, fluid is not exposed to the open air, which is an advantage over some other embodiments. For example, after fluid is infused with an activating agent (e.g., ozone) in the embodiments illustrated in FIGS. 2 and 3, the container is opened and the fluid is poured out of container 36 to transfer the infused fluid. A disadvantage of such an apparatus and method is that the fluid is exposed to the open air. By exposing fluid to the open air, there is a possibility of fluid contamination. The embodiments illustrated in FIGS. 6A to 6C alleviate this disadvantage.

Figure 6B:
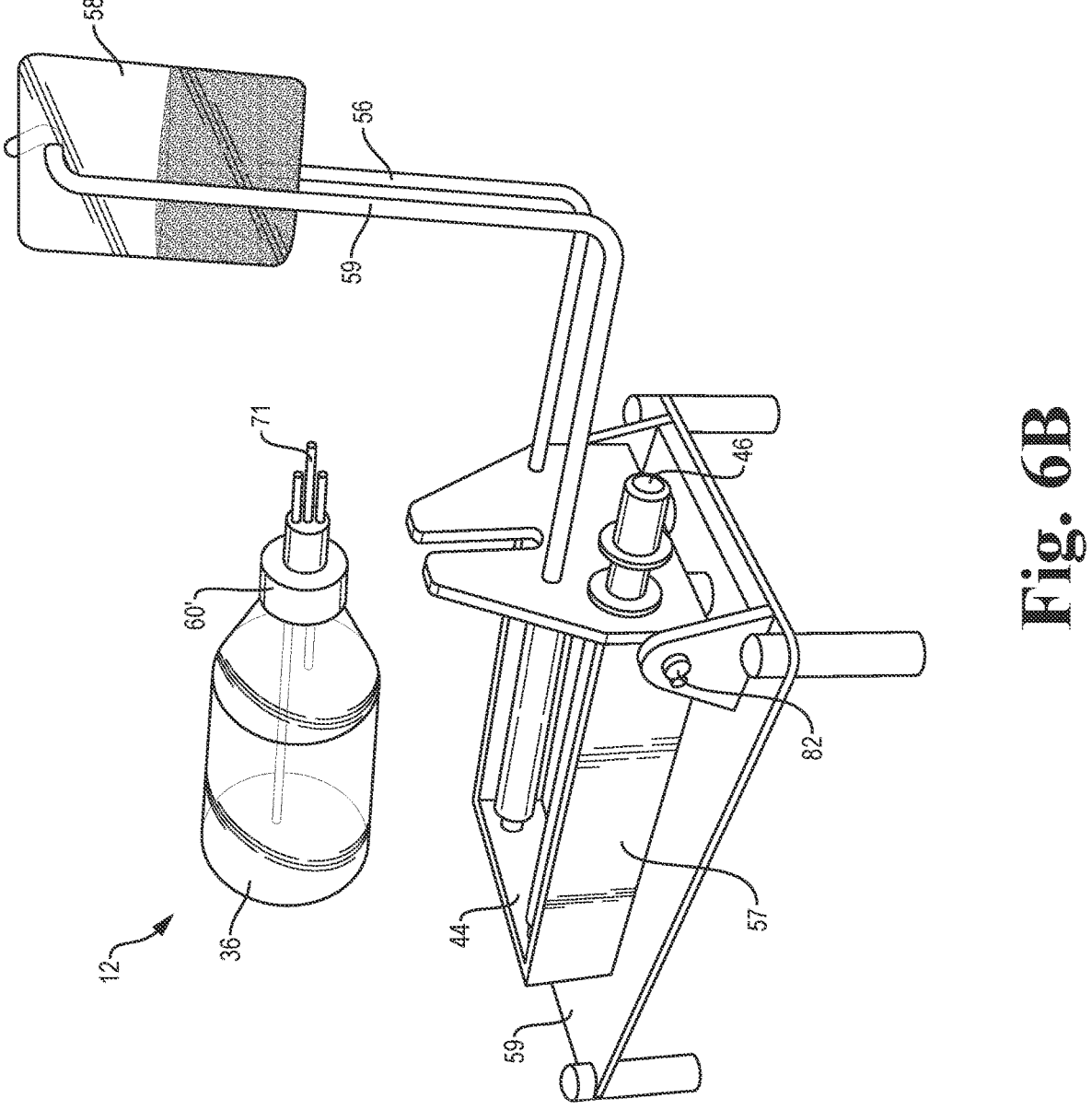
FIG. 6B schematically depicts a perspective view of a contact device of a gaseous activating agent delivery apparatus and a contact member (e.g., container) and rotating joint separated from a pivoting support structure of the contact device for illustrative purposes with the pivoting support structure in a position for loading a fluid from a reservoir into the contact member according to an embodiment of the present disclosure.
Figure 6C:
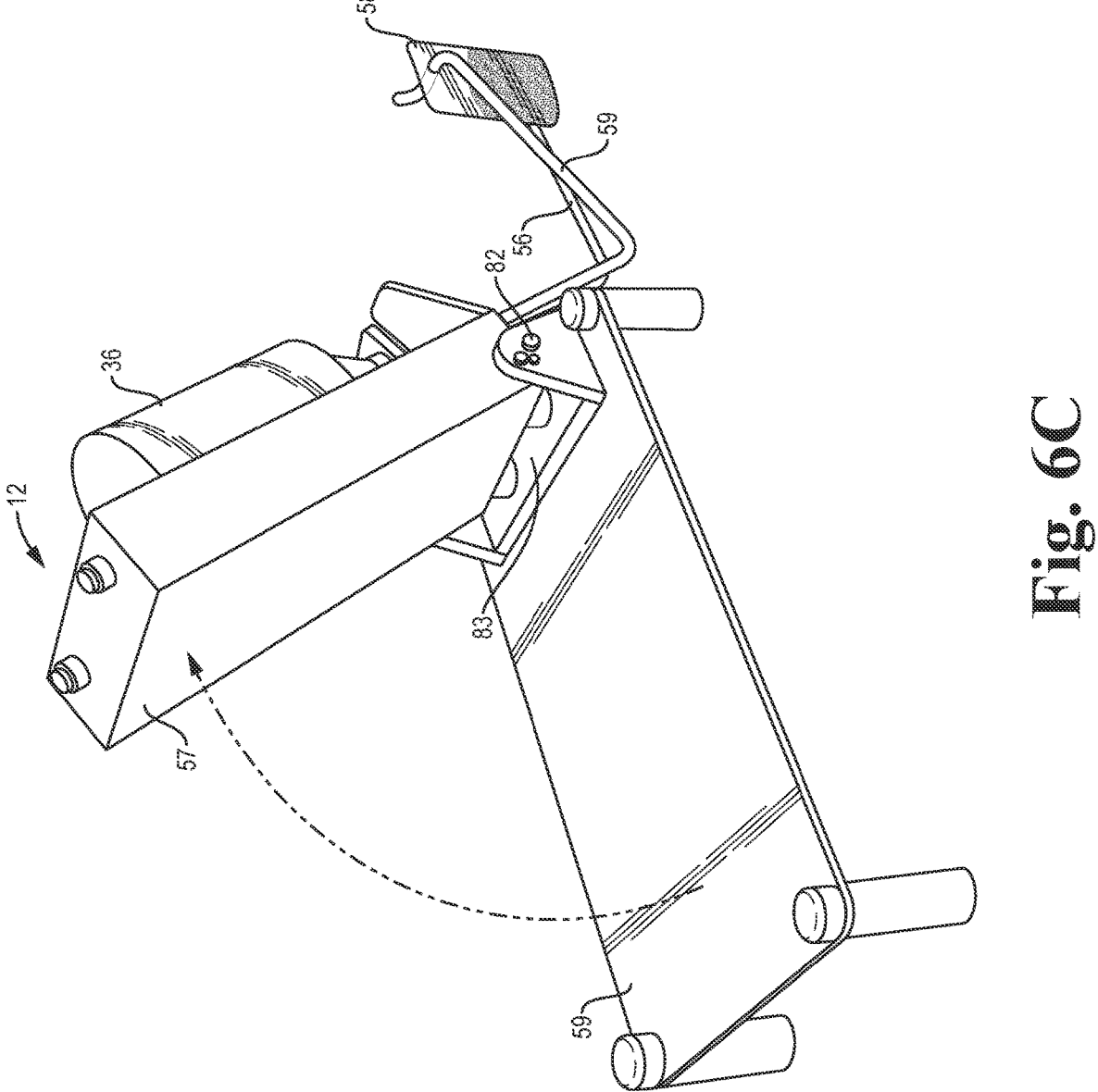
FIG. 6C schematically depicts the contact device, contact member, rotating joint, and reservoir of FIG. 6B with the pivoting support structure in a position for draining the fluid from the contact member into the reservoir after treatment according to an embodiment of the present disclosure.

FIGS. 6B and 6C depict another embodiment of a contact device 12 that employs pivoting of at least portions of the contact device 12 to facilitate draining of fluid from container 36 to reservoir 58. FIG. 6B shows container 36 before it is positioned on the rollers 44 and before the fluid inlet port 56 is connected to the fluid inlet and outlet tube 71. In FIGS. 6A and 6B, the tubing for the gas is omitted for clarity. As shown in FIGS. 6B and 6C, in some embodiments, rollers 44 are rotatably mounted to a pivoting support 57 that is configured to pivot relative to a stationary support 59. In FIG. 6B pivoting support 57 is in an incline position for loading the fluid into container 36 and infusion. In FIG. 6C pivoting support 57 is in a decline position for draining the fluid from container 36 after infusion.

In some embodiments, the contact device 12 includes a reservoir support arm 59 that is attached to pivoting support 57 and configured to support reservoir 58. In some embodiments reservoir support arm 59 is configured and dimensioned such that when pivoting support 57 is in the incline position for fluid loading and infusion (see FIG. 6B) reservoir 58 is higher than container 36, and when pivoting support 57 is in the decline position for draining the fluid, reservoir 58 is lower than container 36.

Figure 7:
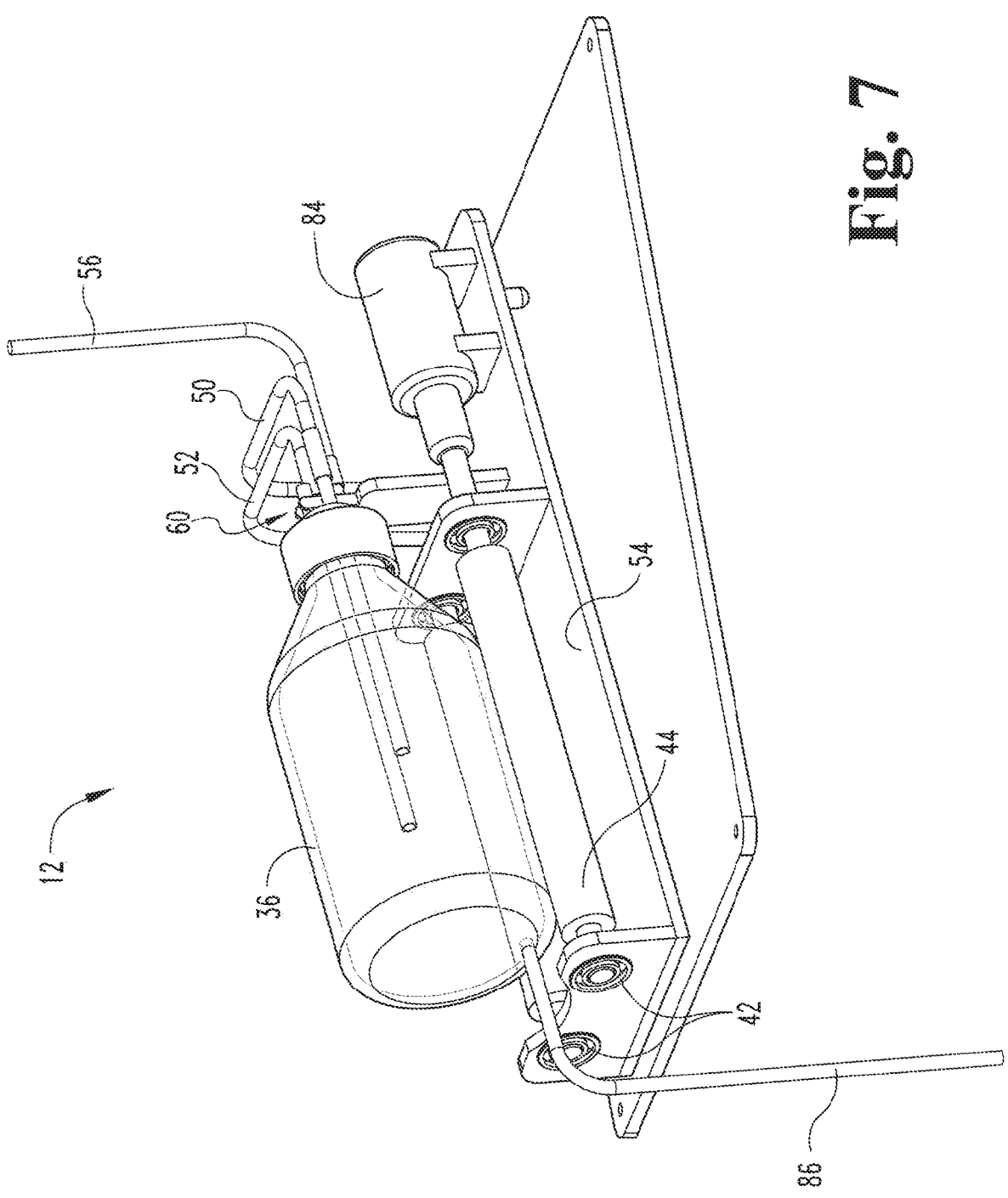
FIG. 7 depicts a perspective view of a contact device of a gaseous activating agent delivery apparatus, a contact member (e.g., container) and a rotating joint where a fluid inlet and a separate fluid outlet are employed according to an embodiment of the present disclosure.

FIG. 7 illustrates a contact device 12, container 36, and rotating joint 60 where separate fluid inlet and fluid outlet ports are employed in accordance with an embodiment of the present disclosure. The contact device 12 includes rollers 44. Rollers 44 are coupled to incline plane 54 via bearings 42. In some embodiments incline plane 54 may be part of or attached to a pivoting support as described above with respect to FIGS. 6B and 6C. A motor 84 is attached to a roller 44 via a bearings 42. In an embodiment, motor 84 is a stepper motor.

In use, a container 36 is placed on top of rollers 44. Rotating joint 60 is detachably attached to container 36. A gas inlet line 50 that extends from input analyzer 32 is coupled to rotating joint 60 via a gas inlet tube 38. In turn, gas inlet tube 38 extends from gas inlet line 50 through rotating joint 60 into container 36. A gas outlet line 52 that extends from output analyzer 34 is coupled to rotating joint 60 via a gas outlet tube 76. Gas outlet tube 76 extends from gas outlet line 52 through rotating joint 60 into container 36.

Fluid inlet port 56 extends from above contact device 12 and is coupled to rotating joint 60 via a fluid inlet tube 70. Fluid inlet tube 74 extends from fluid inlet port 56 through rotating joint 60 into container 36. At a base of the end of container 36 opposite the end of container 36 detachably attached to rotating joint 60, fluid outlet port 86 extends outward from container 36 and extends below to contact device 12. In an embodiment, fluid inlet port 56 and fluid outlet port 86 are comprised of a flexible material. In the embodiment depicted in FIG. 7, fluid exits the fluid outlet port 86 after it has been infused. In an embodiment, a valve (not shown) prevents the fluid from exiting the container 36 during infusion. After the desired measured amount of infusion is achieved, the fluid is removed from the container 36 via fluid outlet port 86 by opening the valve.

In some embodiments, after treatment of the fluid, the contact member 36 is removed from the contact device 12 and elevated to facilitate draining of the fluid from the contact member 36 into a reservoir, or into a patient.

Figure 8:
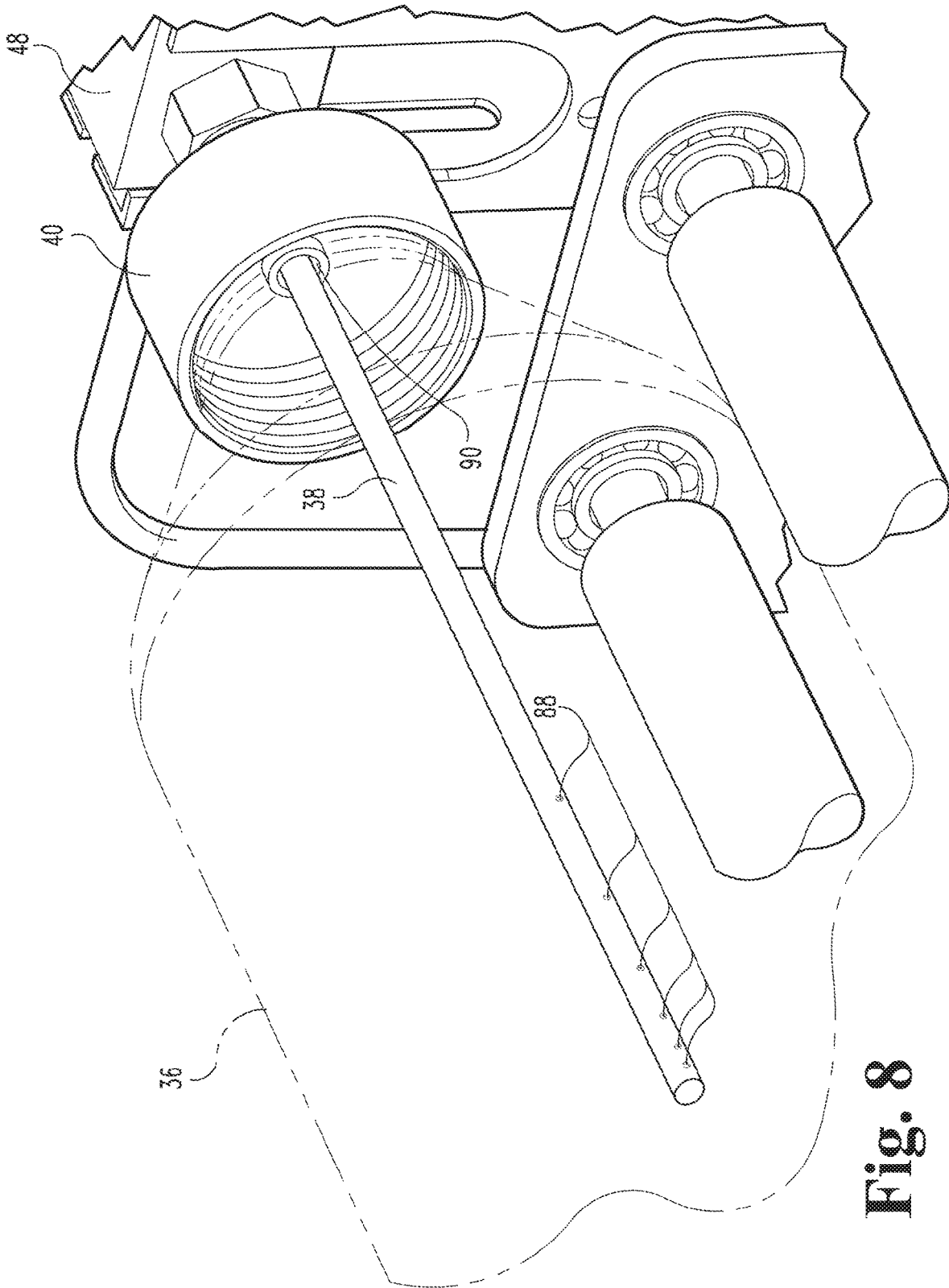
FIG. 8 depicts a perspective view of a portion of a gas contact device, a contact member (e.g., a container), and a gas inlet tube including holes distributed along a portion of a length of the gas inlet tube according to an embodiment of the present disclosure.

FIG. 8 illustrates a gas inlet tube 38 extending through a closure 40 into a container 36. Container 36 is detachably attached to closure 40, which is connected to a permanent rotating joint 48. Gas inlet tube 38 also extends through closure 40 and through permanent rotating joint 48 away from container 36. In another embodiment (not shown) gas inlet tube 38 of FIG. 8 is used in rotating joint 60 or rotating joint 60'. Gas inlet tube 38 includes a series of holes 88 disposed along at least a portion of the length gas inlet tube 38 that extends into container 36. Those of ordinary skill in the art will understand from the present disclosure that holes 88 may be of differing size and shape as the skilled artisan desires. In some embodiments, at the end of container 36 detachably attached to closure 40, an opening 90 or gap is located between gas inlet tube 38 and closure 40 where gas inlet tube 38 extends through closure 40. This opening 90 or gap functions as the gas outlet that enables gas to leave container 36 through permanent rotating joint 48.

As one of ordinary skill in the art would understand from the present disclosure, the entry and exit ports for the gas could be reversed. It is hypothesized that employing holes 88 distributed along at least a portion of a length of the ozone inlet tube 38 within the container will promote a more uniform flow of gas interacting with the thin layer on the interior sidewall surface of the container and thereby promote more uniform and efficient absorption of the gaseous activating agent by the fluid. In some embodiments, dispersion of the gas through holes 88 in gas inlet tube 38 is made more uniform by capping the end of the ozone inlet tube 38 on the side of container 36 opposite of the closure 40.

In some embodiments, the container 36 is a single receiving and processing unit into which withdrawn biological liquid (e.g., blood) is both collected from a patient or subject and processed with a gaseous activating agent for reinfusion into the patient or infusion into a different patient. In some embodiments, the container 36 is a separate unit that receives a previously withdrawn biological liquid (e.g., blood) from a patient or subject held in a collecting bag or other reservoir. In some embodiments, the treated biological liquid is returned to the same collecting bag or reservoir or a new collecting bag or reservoir for reinfusion into the patient or infusion into a different patient. In some embodiments, the treated biological liquid is directly reinfused into the patient or directly infused into a different patient. If the container 36 is a single receiving and processing unit it will need to be manufactured with an appropriate ozone inert material as noted above.

Figure 9:
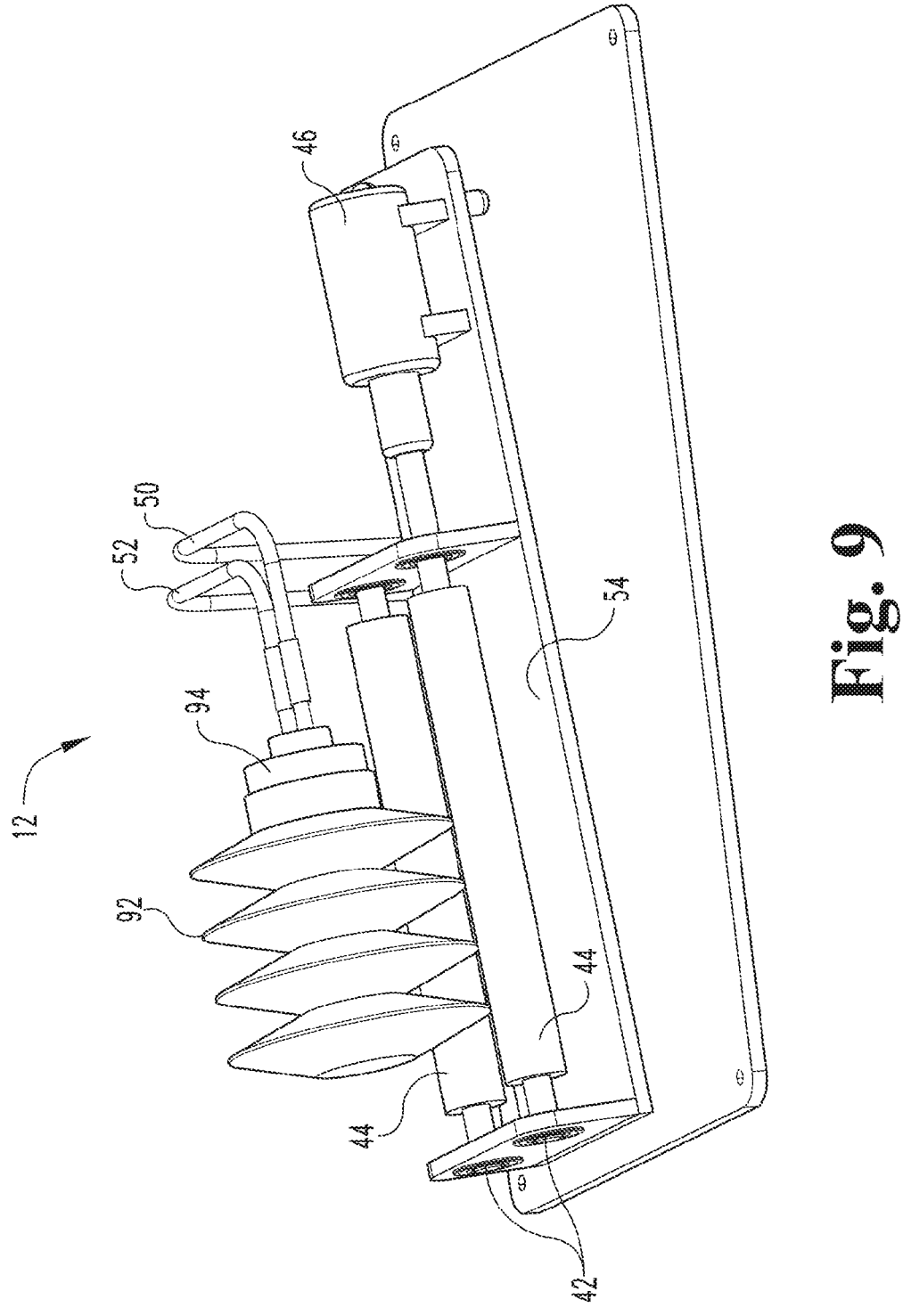
FIG. 9 depicts a perspective view of a contact device of a gaseous activating agent delivery apparatus and a collapsible container connected to the contact device via a rotating joint according to an embodiment of the present disclosure.
Figure 10:
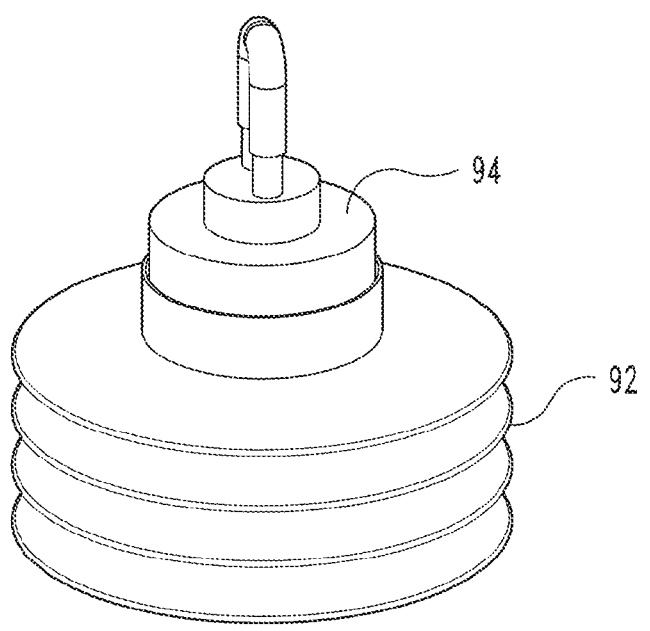
FIG. 10 depicts a perspective view of the collapsible container of FIG. 9 in a collapsed or deflated state connected to a rotating joint according to an embodiment of the present disclosure.
Figure 11:
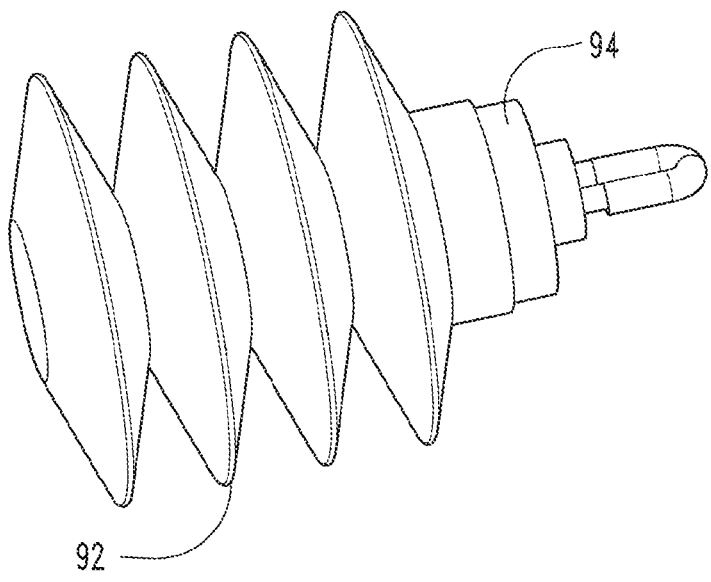
FIG. 11 depicts a perspective view of the collapsible container and rotating joint of FIG. 9 with the collapsible container in an expanded or inflated state according to an embodiment of the present disclosure.

FIG. 9 illustrates a contact device 12 that engages a container 92 having a different configuration in accordance with an embodiment of the present disclosure. The contact device 12 has many elements the same as or similar to those described with respect to FIG. 3, including, for example, gas inlet line 50, gas outlet line 52, motor 46, incline plane 54, rollers 44, and bearings 42, among others. However, the embodiment illustrated in FIG. 9 includes a collapsible container 92 in place of container 36. A container rotating joint 94 is detachably connected to collapsible container 92 and is used to connect a gas inlet line 52 and a gas outlet line 50 to the. The collapsible container 92 has a configuration that enables collapsible container 92 to be inflated when gas enters collapsible container 92 and deflated when gas is expelled from collapsible container 92. FIG. 10 depicts collapsible container 92 in a collapsed or deflated state. FIG. 11 depicts collapsible container 92 in an expanded or inflated state. In some embodiments, collapsible container 92 will not completely deflate when gas is expelled from collapsible container 92 because fluid will be left in collapsible container 92.

Those of ordinary skill will understand from the present disclosure that a collapsible container may have any configuration capable of being rotated and/or oscillated by rollers 44 and may comprise any material having the necessary mechanical properties and that is inert or relatively nonreactive with respect to the gaseous activating agent being employed. Other collapsible configurations that may be employed include, but are not limited to a cylinder, bag, and flexible tube, to name a few. Materials having suitable mechanical properties for the collapsible container include but are not limited to plastic, fiber, rubber, and the like.

In the embodiment illustrated in FIGS. 9-11, container 92 is substantially a cylinder having a plurality of layers. Each of the plurality of layers is substantially the same size and has substantially the same configuration. Each of the plurality of layers has the form of a disk, with each layer being connected the next layer at a center region of the disk. In an embodiment, the collapsible container 92 has a configuration that resembles the bellows of an accordion musical instrument. In an embodiment, the collapsible container 92 is disposable.

In use, fluid is deposited into collapsible container 92. Then collapsible container 92 is placed on contact device 12. Gas inlet line 50 and gas outlet line 52 are both connected to collapsible container 92, and collapsible container 92 is inflated with a gas that is or includes a gaseous activating agent (e.g., ozone). Collapsible container 92 is rotated and/or oscillated using rollers 44 driven by motor 46. After the fluid has been infused with the desired amount of the activating agent, the collapsible container 92 is manually collapsed, releasing any remaining gaseous activating agent, and the collapsible container 92 is removed from contact device 12. In some embodiments, a non-reactive purge gas is used to purge the collapsible container of the gaseous activating agent prior to manually collapsing the collapsible container 92. The treated fluid can be stored in a collapsible container 92 until it is ready to be injected back into a patient or can be transferred to another container for storage.

Figure 14:
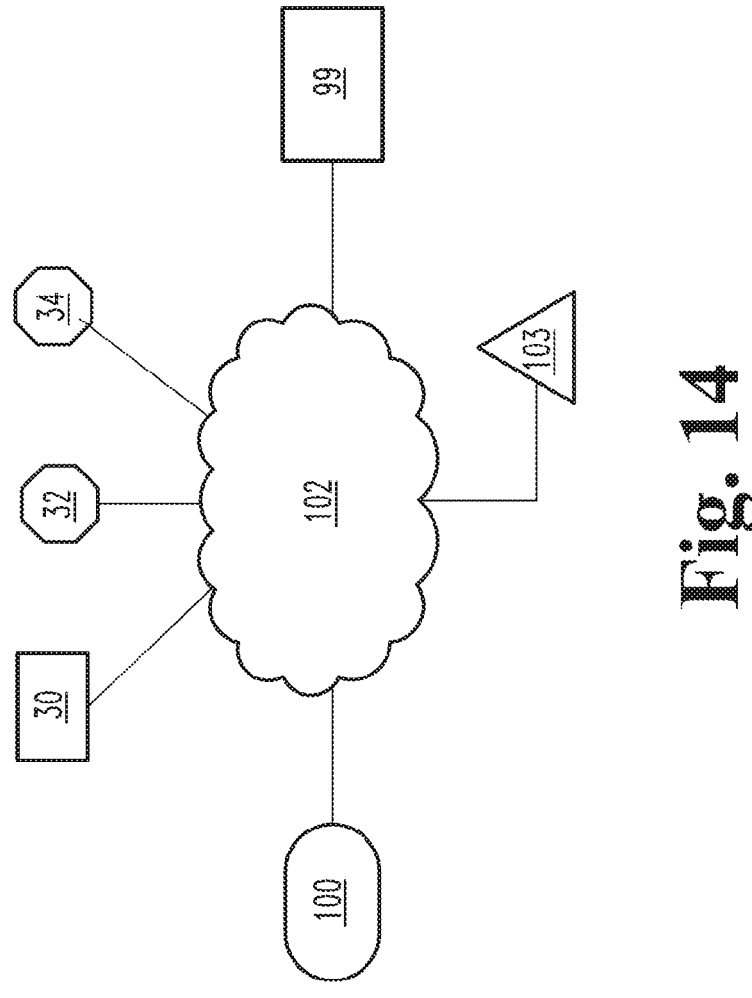
FIG. 14 is a network diagram for implementing some systems and apparatuses described herein according to an embodiment of the present disclosure.

FIG. 14, schematically depicts schematically depicts a network, a system, and components for implementing some embodiments of a gaseous activating agent delivery apparatus and system, and associated methods. This description is presented in terms of programs, data structures or procedures, and code executed or executable on a computing device or a network of computers The network and system may include any or all of software, hardware and firmware. The software programs or code implemented by a computing device in the system may be written in any programming language—interpreted, compiled, or otherwise. These languages may include, but are not limited to, PHP, ASP.net, HTML, HTML5, Ruby, Perl, Java, Python, C++, C#, JavaScript, and/or the Go programming language. It should be appreciated, of course, that one of ordinary skill in the art will appreciate that other languages may be used instead, or in combination with the foregoing and that web and/or mobile application frameworks may also be used. It should further be appreciated that the systems and methods disclosed herein may be embodied in software-as-a-service available over a computer network, such as, for example, the Internet. Further, the present disclosure may enable web services, application programming interfaces and/or service-oriented architectures through one or more application programming interfaces or otherwise.

Server 99 is shown and referred to herein as a single server. However, server 99 may comprise a plurality of servers, virtual infrastructure, or other computing devices or systems interconnected by hardware and software systems know in the art which collectively are operable to perform the functions allocated to server 99 in accordance with the present disclosure.

In some embodiments, the database 100 is configured to store data, content, and other information, including, for example, data regarding elapsed time of gas absorption, fluid volume (mL), gas flow rate (liters/minute), fluid flow rate (liters/minute), average inlet activating agent concentration (ppmv), average exit activating concentration (ppmv), average differential activating agent concentration (ppmv), total delivered-activating agent (μg), total residual-activating agent (μg), activating agent absorbed per interval (μg), total absorbed-dose of activating agent (μg), to name a few non-limiting examples of data.

Database 100 is "associated with" server 99. According to the present disclosure, database 100 can be "associated with" server 99 where database 100 resides on server 99. Database 100 can also be "associated with" server 99 where database 100 resides on a server or computing device remote from server 99, provided that the remote server or computing device is capable of bi-directional data transfer with server 99, such as, for example, in Amazon AWS®, Rackspace®, or other virtual infrastructure, or any business network. In at least one embodiment, the remote server or computing device upon which database 100 resides is electronically connected to server 99 such that the remote server or computing device is capable of continuous bi-directional data transfer with server 99.

For purposes of clarity, database 100 is shown in FIG. 14, and referred to herein as a single database. It will be appreciated by those of ordinary skill in the art that database 100 may comprise a plurality of databases connected by software systems of a type well known in the art, which collectively are operable to perform the functions delegated to database 100 according to the present disclosure. Database 100 may comprise a relational database architecture or other database architecture of a type known in the database art. Database 100 may comprise one of many well-known database management systems, such as, for example, MICROSOFT's SQL Server, MICROSOFT's ACCESS, or IBM's DB2 database management systems, or the database management systems available from ORACLE or SYBASE. Database 100 retrievably stores information that is communicated to database 100 from user device 103 and server 99.

Data acquisition modules 30, input analyzer 32, output analyzer 34, user device 103, and server 99 communicate via computer network 102. If database 100 is in disparate infrastructure from server 99, database 100 may communicate with server 99 via computer network 102. Computer network 102 may comprise the Internet, but this is not required. In some embodiments, the functionality of the server 99 is instead incorporated into a user device 103 that is associated with or incorporated into the apparatus or system.

Figure 15:
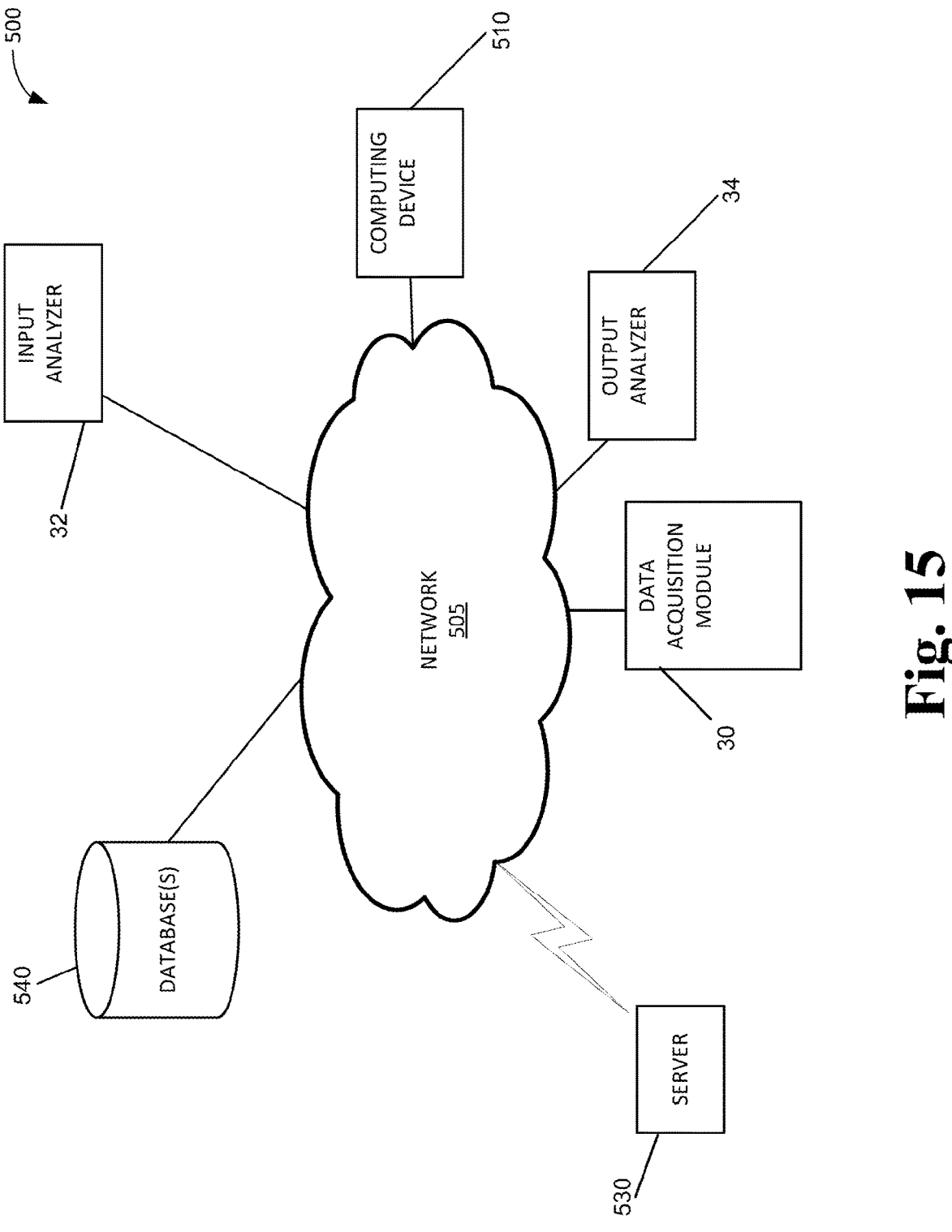
FIG. 15 is a block diagram of an exemplary system for implementing some embodiments described herein.

FIG. 15 illustrates a network diagram depicting a system 500 for implementing some embodiments described herein. The system 500 can include a network 505, multiple devices (e.g., an input analyzer 32, an output analyzer 14, a data acquisition module 30, a computing device 510, a server 530, and database(s) 540. Each of input analyzer 32, output analyzer 14, data acquisition module 30, and computing device 510 may be in communication with the network 505.

In an example embodiment, one or more portions of network 505 may be an ad hoc network, an intranet, an extranet, a virtual private network (VPN), a local area network (LAN), a wireless LAN (WLAN), a wide area network (WAN), a wireless wide area network (WWAN), a metropolitan area network (MAN), a portion of the Internet, a portion of the Public Switched Telephone Network (PSTN), a cellular telephone network, a wireless network, a WiFi network, a WiMax network, another type of network, or a combination of two or more such networks.

The computing device 510 may include, but is not limited to, work stations, computers, general purpose computers, a data center (a large group of networked computer servers), Internet appliances, hand-held devices, wireless devices, portable devices, wearable computers, cellular or mobile phones, portable digital assistants (PDAs), smart phones, tablets, ultrabooks, netbooks, laptops, desktops, multi-processor systems, microprocessor-based or programmable consumer electronics, network PCs, mini-computers, and the like. The computing device 510 can include one or more components described in relation to computing device 600 shown in FIG. 16. The computing device 510 may be used to control one or more aspects of operation of the system. In some embodiments, the computing device 510 also include a graphical user interface that receives user input for control of one or more aspects of the system. In some embodiments a different computing device may be used to receive user input for control of one or more aspects of the system. In other embodiments, one or more components of the system shown connected to the computing device 510 by the network 505 may instead by incorporated into the computing device.

In some embodiments, the computing device 510 is connected to the network 505 via a wired or wireless connection. In some embodiments, the computing device 510 is in wired or wireless communication with the data acquisition module 30. In some embodiments, the computing device 510 is in wired or wireless communication with the data acquisition module 30. In some embodiments, the computing device 510 is in wired or wireless communication with the input analyzer 32 and the output analyzer 34. In some embodiments, the input analyzer 32 and the output analyzer 34 communicate with the data acquisition module 30, which communicates with the computing device 510. In some embodiments, the computing device 510 is in wired or wireless communication with the database 540. In other embodiments, the database is omitted an required storage is incorporated into the computing device 510.

The database 540 and server 530 are connected to the network 505 via a wired or wireless connection. The server 530 may include one or more computers or processors configured to communicate with the computing device 510 via network 505. In some embodiments, the server 530 hosts one or more applications accessed by the computing device 510 and/or facilitates access to the content of database(s) 540. Database(s) 540 may include one or more storage devices for storing data and/or instructions (or code) for use by the server 530, and/or computing device 510. Database(s) 540 may also store data generated by the system during use (e.g. composition data from input analyzer and output analyzer and flow data from flowmeter, results of calculations or determinations like activating agent absorption rates over time and total absorbed mass of the activating agent as a function of time, rotation or oscillation rates as a function of time, etc.). Database(s) 540 and server 530 may be located at one or more geographically distributed locations from each other or from devices 510, 520. Alternatively, database(s) 540 may be included within server 530.

Figure 16:
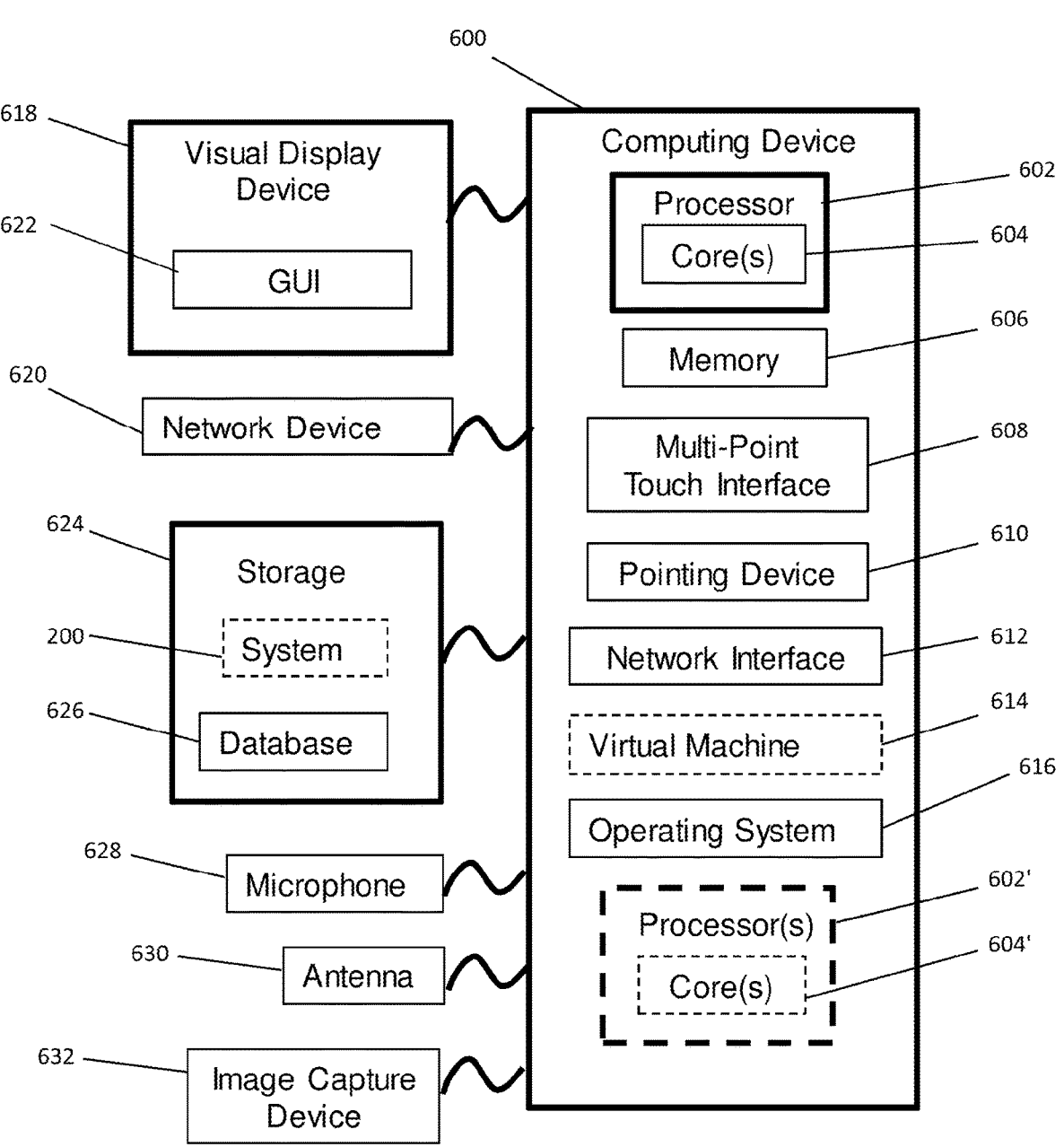
FIG. 16 is a block diagram of an exemplary computing device that may be used to implement some exemplary embodiments described herein.

FIG. 16 is a block diagram of an exemplary computing device 600 that can be used to perform the methods provided by some exemplary embodiments. The computing device 600 includes one or more non-transitory computer-readable media for storing one or more computer-executable instructions or software for implementing exemplary embodiments. The non-transitory computer-readable media can include, but are not limited to, one or more types of hardware memory, non-transitory tangible media (for example, one or more magnetic storage disks, one or more optical disks, one or more USB flashdrives), and the like. For example, memory 606 included in the computing device 600 can store computer-readable and computer-executable instructions or software for implementing exemplary embodiments. The computing device 600 also includes processor 602 and associated core 604, and optionally, one or more additional processor(s) 602' and associated core(s) 604' (for example, in the case of computer systems having multiple processors/cores), for executing computer-readable and computer-executable instructions or software stored in the memory 606 and other programs for controlling system hardware. Processor 602 and processor(s) 602' can each be a single core processor or multiple core (604 and 604') processor.

Virtualization can be employed in the computing device 600 so that infrastructure and resources in the computing device can be shared dynamically. A virtual machine 614 can be provided to handle a process running on multiple processors so that the process appears to be using only one computing resource rather than multiple computing resources. Multiple virtual machines can also be used with one processor.

Memory 606 can include a computer system memory or random access memory, such as DRAM, SRAM, EDO RAM, and the like. Memory 606 can include other types of memory as well, or combinations thereof.

In some embodiments, a user can interact with the computing device 600 through a visual display device 618, such as a touch screen display or computer monitor, which can display one or more user interfaces 619 that can be provided in accordance with exemplary embodiments. The visual display device 618 can also display other aspects, elements and/or information or data associated with exemplary embodiments. The computing device 600 can include other I/O devices for receiving input from a user, for example, a keyboard or other suitable multi-point touch interface 608, a pointing device 610 (e.g., a pen, stylus, mouse, or trackpad). The keyboard 608 and the pointing device 610 can be coupled to the visual display device 618. The computing device 600 can include other suitable conventional I/O peripherals.

In some embodiments, one or more of the input analyzer 32, the output analyzer 34, and the data acquisition module 30 may be connected directly to the computing device 600. In some embodiments, the data acquisition module 30 may be incorporated into the computing device 30.

The computing device 600 can also include one or more storage devices 624, such as a hard-drive, CD-ROM, or other computer readable media, for storing data and computer-readable instructions and/or software, such as the system 200 that implements exemplary embodiments of described herein, or portions thereof, which can be executed to obtain data from various components of the system, to control one or more aspects of operation of the system, such as initiating or stopping a flow of gas to the container, controlling a rate of flow of gas to the container, controlling a flow of a purge gas to the container, controlling a composition of gas delivered to the system, and/or controlling a rotation or oscillation of the container, and to generate user interface 619 on display 618. Exemplary storage device 624 can also store one or more databases for storing suitable information required to implement exemplary embodiments. Exemplary storage device 624 can also store data generated by the system during use (e.g. composition data from input analyzer and output analyzer and flow data from flowmeter, results of calculations or determinations like activating agent absorption rates over time and total absorbed mass of the activating agent as a function of time, rotation or oscillation rates as a function of time, etc.) Exemplary storage device 624 can store one or more databases 626 for storing data used to implement exemplary embodiments of the systems and methods described herein.

The computing device 600 can include a network interface 612 configured to interface via one or more network devices 622 with one or more networks, for example, Local Area Network (LAN), Wide Area Network (WAN) or the Internet through a variety of connections including, but not limited to, standard telephone lines, LAN or WAN links (for example, 802.11, T1, T3, 56kb, X.25), broadband connections (for example, ISDN, Frame Relay, ATM), wireless connections, controller area network (CAN), or some combination of the above. The network interface 612 can include a built-in network adapter, network interface card, PCMCIA network card, card bus network adapter, wireless network adapter, USB network adapter, modem or another device suitable for interfacing the computing device 600 to a type of network capable of communication and performing the operations described herein. Moreover, the computing device 600 can be a computer system, such as a workstation, desktop computer, server, laptop, handheld computer, tablet computer (e.g., the iPad® tablet computer), mobile computing or communication device (e.g., the iPhone® communication device), or other form of computing or telecommunications device that is capable of communication and that has sufficient processor power and memory capacity to perform the operations described herein. The computing device 600 can run operating systems 616, such as versions of the Microsoft® Windows® operating systems, different releases of the Unix and Linux operating systems, versions of the MacOS® for Macintosh computers, embedded operating systems, real-time operating systems, open source operating systems, proprietary operating systems, operating systems for mobile computing devices, or another operating system capable of running on the computing device and performing the operations described herein. In exemplary embodiments, the operating system 616 can be run in native mode or emulated mode. In an exemplary embodiment, the operating system 616 can be run on one or more cloud machine instances.

The present disclosure also provides improved and simplified liquid phase flow mechanics of generating, modulating, and controlling the reactive gas phase/liquid phase interaction and absorption of a gaseous activating agent (e.g., oxidizing ozone) in a fluid. The present disclosure further provides an expanded method of operational robustness for increased processing speed by employing a more efficient method of creating and controlling exposure between the gaseous activating agent (e.g., ozone) and fluid, degree, and rate of absorption and the modulative generation of apoptotic cells (AC) and specifically dynamic control generation of apoptotic cells ("dcAC") while limiting production of necroptotic cells.

The present disclosure discusses apoptosis, which refers to an engineered cell turnover process reflecting normal physiology employed by the body for elimination of unwanted or no longer useful cells referred to as programmed cell death. Apoptosis is a non-inflammatory (non-phlogistic) mechanism the body also uses to resolve an immunogenic state and reestablish a quiescent balanced state of immune homeostasis subsequent to its response to injury or infection. It is effected by phagocytes, both professional such as leukocytes or non-professional such as endothelial cells. This process is evidenced by rounding-up of the cell, retraction of pseudopodes, changes in membrane distribution lipids or proteins, membrane blebbing, condensation of cytoplasm and crescent condensation of the nuclear chromatin beneath the nuclear membrane chromatin, internucleosomal DNA degrading fragmentation with cellular constituents sequestered in membrane-enclosed apoptotic bodies, together with loss of cellular and nuclear volume, and/or signaled formation of a mitochondrial membrane permeabilization pore that produces inner mitochondrial membrane permeabilization and disruption of mitochondrial membrane potential ($\Delta\Psi m$). This disruption in turn triggers release of pro-apoptotic factors such as cytochrome c from mitochondria into the cytosol and an apoptosome related cascade of events producing the induction of apoptotic programmed cell death sequence.[12][13] Apoptosis, as used in the present disclosure, shall extended to include "eryptosis" and related mechanics, meaning the programmed cell death of erythrocytes.[14][15]

Necroptic cells are cells in nature evincing increased cell volume (oncosis) culminating in disruption of the plasma membrane in programmed necrotic death. The necroptotic cellular process is preceded by a nuclear translocation and sequential activation of pseudokinase mixed lineage kinase domain-like protein (MLKL) and the protein kinases RIPK1 and RIPK3.[1][2][3] RIPK3-mediated phosphorylation of MLKL triggers its oligomerization, which is necessary and sufficient for the induction of cell death.[4][5] Other non-apoptotic forms of triggered cell stress or signaled activated, generated or programmed cell death having differing inductive causes are pyroptosis, ferroptosis, parthanatos, and (N)Etosisor), none of which evidence the functional characteristics or signaling viability as AC and are included herein under the definition of Necroptosis.[6]

In some embodiments, a ratio of generated necroptic cells to generated AC is less than 0.50. In some embodiments, a ratio of generated necroptic cells to generated AC is less than 0.2. In some embodiments, a ratio of generated necroptic cells to generated AC is less than 0.1. In some embodiments, generated AC have a percentage to generated necroptic cells of no less than 50%. In some embodiments, generated AC have a percentage to generated necroptic cells of no less than 90%.

In some embodiments of the present disclosure, the thickness and nature including flow characteristics of a thin-film formed from a fluid including a biological fluid (e.g., blood) evolve over time based, at least in part, on rotational speed (or oscillating speed as the case may be) and derived viscosity. The relative thin-film thickness and surface area is exponentially related to the velocity of the rotating or oscillating container. In embodiments in which the activating agent has a high reactivity with the biological liquid, the penetrating capacity of the activating agent into the depth of the fluid may be severely limited. For example, because of the high reactivity of ozone ($O_3$) with blood, thin-film surface low-reactive metabolite byproducts are immediately formed consuming the $O_3$ and severely limiting the $O_3$ reactive penetrating capacity in the blood, thereby restricting its reactivity to the blood surface. Controlling the thickness of the thin-film, therefore, is a reaction rate and through-put controlling parameter.

The following description uses ozone ($O_3$) as an example activating agent and uses a fluid containing blood as the example fluid; however, one of skill in the art will appreciate that the description also applies to other gaseous activating agents and fluids including other biological liquids or cells. Upon exposure of the blood to $O_3$, the $O_3$ reacts with and activates components of the blood. The mass of $O_3$ that has been reactively absorbed by the blood is the difference between the total mass of $O_3$ that enters the container verses the total mass of $O_3$ that exits the container (the "Net Mass"). The total mass of $O_3$ that has flowed into the container at a point in time is calculated by integrating as a function of time the formula: (Flow Rate(t)*Volume Fraction$_{in}$(t)*Density of Ozone). Similarly, the total mass of $O_3$ that has flowed out of the container at a point in time is calculated by integrating as a function of time the formula: (Flow Rate(t)*Volume Fraction$_{out}$(t)*Density of Ozone). The difference between these two values yields the Net Mass absorbed at the point in time. The flow rate is the flow rate of gas into the contact member (e.g., container). In some embodiments, the flow rate is provided by flow meter 24. The volume fraction$_{in}$ is the portion of the gas flowing into the contact member (e.g., container) that is $O_3$, which may be constant or may be varied over time. The volume fraction$_{out}$ is the portion of the gas flowing out of the container that is $O_3$, which will vary as a function of time based on absorption of $O_3$ by the blood. In some embodiments, information regarding the volume fraction$_{out}$ is provided by the input analyzer 32 and information regarding the volume fraction$_{out}$ is provided by the output analyzer 34. By multiplying the flow rate by the input or output volume fraction of $O_3$, the flow rate of just the $O_3$ into or out of the container as a function of time is obtained. By multiplying the flow rate of just the $O_3$ into or out of the container by the mass density, the mass flow rate of the $O_3$ into or out of the container (the "Mass/Time Ratio" for flow into or out of the container) is determined. By integrating this Mass/Time Ratio for flow into or out of the container over time, the total mass of $O_3$ that flowed into the container or the total mass that flowed out of the container can be obtained. Subtracting the total mass of $O_3$ that flowed out of the container from the total mass of $O_3$ that flowed into the container yields the Net Mass of $O_3$ absorbed by the fluid. In some embodiments, systems and apparatuses perform data collection and integration in real time to provide a current determination of total mass of $O_3$ absorbed during the treatment of the blood.

In some embodiments, the control system includes a computing device having one or more processors configured to execute code that, when executed, causes the apparatus to generate, receive, obtain, or access information regarding a flow rate of gas into the contact device (e.g., into the contact member), information regarding a volume fraction of a gaseous activating agent flowing into the contact device, and information a volume fraction of the gaseous activating agent flowing out of the contact device. In some embodiments, the code, when executed, determines a total amount (e.g., a total mass) of activating agent absorbed by a fluid in the contact member. In some embodiments, the determination is repeated continuously or periodically during treatment of the fluid to yield a real time estimate of current total absorption during treatment. In some embodiments, the code, when executed, determines a rate of gaseous activating agent absorption based, at least in part, on a flow rate of the gas delivered to the gas-fluid contact device, a composition of the gas output from gas-fluid contact device, and a rate of flow of gas through the gas-fluid contact device. In some embodiments, the code, when executed, causes the apparatus or system to alter a composition of the gas delivered to the gas-fluid contact device or a flow rate of the gas delivered to the gas-fluid contact device based, at least in part, on a determined current total amount of the activating agent absorbed by the fluid and/or on the determined rate of gaseous activating agent absorption by the fluid. In some embodiments, the code, when executed, causes the apparatus or system to alter a rotation rate or oscillation rate of the contact member based, at least in part, on a total amount of the activating agent absorbed by the fluid and/or on the determined rate of gaseous activating agent absorption by the fluid. In some embodiments, the code when executed, causes the apparatus or system to cease delivering gas including the gaseous activating agent to the contact member based, at least in part, on the determination of the total amount of gaseous activating agent absorbed by the fluid. In some embodiments, the code when executed, causes the apparatus or system to initiate flow of a nonreactive purge gas into the contact member based, at least in part, on the determination of the total amount of gaseous activating agent absorbed by the fluid. In some embodiments, the code when executed, automatically controls one or more parameters of the apparatus to obtain the pre-specified amount of the gaseous activating agent absorbed by the fluid within a pre-specified total gaseous activating agent exposure time.

One of ordinary skill in the art, in view of the present disclosure, will appreciate that methods described herein are not limited to the particular systems and apparatuses depicted in the figures. A method of treating a fluid including a biological liquid and/or cells with a gaseous activating agent include delivering a measured quantity of the fluid to a contact member such that the fluid is in contact with an interior surface of the contact member. The method also includes rotating or oscillating the contact member to form a thin layer of the fluid on at least a portion of the interior surface of the contact member. The method also includes delivering a gas that includes or is the gaseous activating agent to the contact member enabling the gaseous activating agent to interact with the thin layer of fluid during the rotation or oscillation. The method also includes continuing the rotation or oscillation until a desired total amount of the gaseous activating agent is absorbed by the fluid.

In some embodiments, the method also includes determining a total amount of the gaseous activating agent absorbed by the fluid during the rotation or oscillation. In some embodiments, determinations of the total amount of the gaseous activating agent absorbed by the fluid are made continuously or periodically during the treatment of the fluid.

In some embodiments, a rate of absorption of the activating agent by the fluid is determined. In some embodiments, determinations of the rate of activating agent absorption are made continuously or periodically during the treatment of the fluid.

In some embodiments, a composition of the input gas or a rate of delivery of the input gas is adjusted based, at least in part, on the determined total amount of the gaseous activating agent absorbed by the fluid and/or on the determined rate of activating agent absorption. In some embodiments, this adjustment is made during treatment of the fluid. In some embodiments, an adjustment of the rate of delivery of the gas to the contact member or a composition of gas delivered to the contact member modifies a total exposure time of the fluid to the gaseous phase activating agent required to reach the desired total amount of the gaseous activating agent absorbed by the fluid.

In some embodiments, rate of rotation or oscillation of the contact member is adjusted based, at least in part, on the determined total amount of the gaseous activating agent absorbed by the fluid and/or on the determined rate of activating agent absorption. In some embodiments, this adjustment is made during treatment of the fluid. In some embodiments, the adjustment of rate of rotation or oscillation of the contact member modifies a total exposure time of the fluid to the gaseous phase activating agent required to reach the desired total amount of the gaseous activating agent absorbed by the fluid.

In some embodiments, the method includes determining an estimated total exposure time required to obtain the desired total absorption amount of the gas by the fluid, and based on the estimated total exposure time required, altering the estimated total exposure time required by adjusting one or more of: a rate of oscillation or rotation of the contact member, a rate of flow of gas into the contact member, and a concentration of gas flowing into the contact member. In some embodiments, the contact member is continuously rotated to form the thin layer of the fluid on at least the portion of the interior surface of the contact member.

Blood is a pseudoplastic liquid with sheer thinning thixotropic behavior evidencing a two-phase suspension of formed cellular elements (e.g., RBCs, leukocytes and platelets) suspended in an aqueous solution of organic molecules, proteins (notably albumin, fibrinogen, globulin and plasminogen), as well as plasma, the intravascular fluid fraction of extracellular fluid (all body fluid outside of cells) containing soluble and suspended insoluble extracellular matrix components. All elements of blood (cellular and non-cellular) also demonstrate phenomena that are unique to the mechanisms defining the cellular action sequence of their programmed cell death and are potential activation targets of blood subject to variance of parameters and exposures controlled by the ozone dynamic control delivery system (the "Target(s)").

Blood is subject to mixed boundary conditions of surface tension liquid/gas and liquid/solid interfaces. The apparent viscosity of blood depends on existing shear forces (i.e., blood behaves as non-Newtonian fluid)[7] and is determined by hematocrit, plasma viscosity, RBC aggregation, and the mechanical properties of the Targets. Treatment of the blood (and Targets) can be modulated by adjusting the activating agent delivery apparatus and system variables including size (e.g., volume) of the contact member, total amount of blood processed in given batch, and rate of rotation, which will modify and give effect to the thin film liquid thickness of the flow, and in turn the degree and time of exposure of blood and bodies within the blood to the activating agent (e.g., $O_3$)

In some embodiments, the behavior of the generated thin-film of blood in the rotating container can be approximated by a free flow of a non-Newtonian fluid on a continuously wetted cylindrical substrate using a fourth order diffusion partial differential equation (PDE). The thin-film experiences apparent viscous, non-linear and time dependent stresses arising from curved substrate strain flow rate, together with sheer stress under the modulating effect of reversing gravity and rotational inertia relative to velocity (produced by the rotating container and impacting its thixotropic hysteresis loop). Both blood/sidewall substrate and blood/ozone interfaces evolve over time and are treated as time evolution functions.

In some embodiments, the thixotropic sheer thinning behavior produced by the ozone delivery system can be modified by adding a non-reactive sterile thinning solution to the blood such as normal saline.

For blood as a non-Newtonian fluid, viscosity can be changed by many orders of magnitude in adjusting the rotational rate of the contact device and motor powering the contact device (velocity gradient).[8] Therefore, the parameter of rotational velocity is a prime operating parameter for this method and means of process and output control, but also in relation to various additional physical system effects including system geometry, surface tension, thermodynamic effects, chemical kinetics, materials properties and constitutive equations of state,[9] all of which comprise adjustable variables of this invention.

Collectively, blood rheology impacted by the gaseous activating agent delivery system's design and the novel operational flexibility provided in adjustability of the thin-film nature of the treated blood including flow characteristics determined by rotational speed derived viscosity and the relative thin-film surface area of exposure as a ratio to its thickness, as well as surface area time evolution exposure, all provide unique and novel means of process control translating into greater efficiency in manufacturing AC and in operational flexibility with modifiable biological composition and functionality characteristics as product of the process.

Cell bodies and other components in suspension or solution within the plasma (Targets) are subjected to activation signaling by the ozone while also under subject of stress forces of motion produced by the ozone delivery system. Cell bodies are impacted by mechanobiological non-linear forces including laminar shear stress, frictional forces and flow-induced mechanotransducton. These generated forces can in turn cause activation of stretch-sensitive mechanoreceptors and other motion, cell deformation or rheological strain responses ("Mechanobiological Responses"). Such an effect further lends to the utility of this method, representing variables available for process modification of generated AC including specific cellular expressions and secretions and is integral to this invention. When discussing "activation" in the present disclosure, such a term includes the activating, stressing, reacting, inducing, signaling, promoting, effecting, or similarly creating a modifying or transforming response in blood plasma including cellular bodies and their exposure to a DNA, mitochondrial or endoplasmic reticulum (ER) stressing agent such as oxidizing ozone and to cause the cell body, by surface translocation exposures, activation, expression, secretion, cell-cell, other extracellular released fragment,—matrix modification, or other method of communication, to signal—tolerogenic resolution and/or homeostatic response by immune and immune-like acting cells.

Production of AC in the Treated blood shall be confirmed employing common methods of cell viability analysis, such as measurement of mitochondrial dehydrogenase activity using MTT or CCK-8; DAPI staining (apoptotic cell density); annexin V or TdT-mediated dUTP nick and labeling (TUNEL-positive nucleus) assays; double labeled cells analyzed by fluorescence microscope (apoptotic index); and total cell quantification using a dye exclusion test (Trypan Blue) and classic apoptosis (AnxV+/PI negative) versus immunogenic death (CRT+) markers.

Although ozone is used throughout the many embodiments described and illustrated in the present disclosure, any number of gaseous activating agents may be utilized in accordance with the present disclosure. Such a gaseous activating agent includes an activating airborne compound (an oxidizing, nitrodizing/nitriating, oxynitriding, enzymatic inducing, pharmaceutical or other cellular agent that is gaseous, gaseous-like or a mistable mixture (e.g., a flowable liquid containing micro/nano-particles, micro/nano-spheres or other fine material 1 nm to 100 μm in size) in nature. Gaseous activating agents include but are not limited to: oxidizing agents (e.g., ozone ($O_3$)), reactive oxygen species (ROS) producing agents (e.g., carbon monoxide, nitric oxide, superoxide, singlet oxygen, hydrogen peroxide, hydrogen disulfide, carbon dioxide, xenon or other electron acceptors), and any chemical, pharmaceutical, biologic or biological apoptosis inducing agent together with derivatives and metabolites, that alone or in combination, effect Fas signaling, proapoptotic Bcl-2 family member signaling, cytochrome c leakage, caspase-3 or -8 activation, DNA fragmenting, laddering, or single/double strand breaking (e.g., 2-Amino-N-quinolin-8-yl-benzenesulfonamide, Arylquin 1, Brassinin, Camalexin, Cinnabarinic Acid, Cirsiliol, Cisplatin, Concanavalin A, Hinokitiol, Imiquimod, Monensin Sodium Salt, Nifetepimine, Okadaic Acid, Phenoxodiol, Pterostilbene, L-Sulforaphane, Sulindac Sulfone, Temozolomide, Tocopheryl Succinate, Staurosporine, Triamcinolone, Vacquinol-1 dihydrochloride, Violacein). In some embodiments. gaseous activating agent is $O_3$, which possesses the fourth highest oxidative potential of any chemical species in nature.[10] If $O_3$ is the gaseous activating agent employed, medical grade oxygen is the preferred source or precursor gas to be used, as lesser grades of oxygen may include nitrogenous contaminants resulting in the formation of toxins. The oxidizing stressors can be complemented with or by other methods of stressing including ultraviolet light, ionizing irradiation, heat, chemical, pharmaceutical or other such apoptosis generating agents, or employed with the device alone or in combination, but without oxidizing or ozone stressing.

In embodiments that employ ozone, ozone contacting surfaces are preferably comprised of materials that are non-reactive and inert to ozone. Any ozone resistant material can be used, however, unless such material is $O_3$-inert, it may participate in the reaction with $O_3$, potentially producing deleterious by-products and corrupting the $O_3$ mass consumption measurements and invalidating processing control. Appropriate inert materials include stainless steel, titanium, boro silicate, quartz, ceramic composites, PFA (copolymer of tetrafluoroethylene and perfluorinated vinyl ether from the perfluoroalkoxy group) and PTFE (polytetrafluoroethylene). Such materials may be used in accordance with all embodiments of the present disclosure.

The present disclosure also provides a therapeutic method of treating a cell body in a biological viscoelastic liquid, such a blood, with a gaseous activating agent, such as ozone, for the purpose of transforming the liquid and by which at least some cell bodies and other fractions (i.e. plasma) within the liquid are activated in a manner that when infused in a patient a signal is generated promoting an immune and immune-like inflammation resolving and healing response. The method employs a system having a container rotating on a non-vertical axis into which a measured liquid phase mass is placed and in turn exposed to the gaseous activating agent in a controlled manner providing for exposure to and absorption of a pre-specified mass, all in a dynamically controlled manner and for the purpose of effecting a precise and targeted activation of cell bodies contained within the liquid phase.

Dynamic control refers to the orchestrated use of multiple adjustable operating parameters and with varying combination of the parameters to achieve with precision a desired performance and output in a device that processes the absorption of a gaseous or gaseous-like reactive material by a non-linear viscoelastic non-Newtonian liquid (such as a biological liquid or a fluid including a biological liquid (e.g., blood) or cells. Dynamic control variables available for processing include:

1. Container or vessel geometry
2. Container volume
3. Rate of rotation or oscillation of the container,
4. Duration of gas-liquid reaction period
5. Rate of gas flow into and out of the container
6. Gas composition (e.g., $O_3$ to $O_2$ mixture ratio)
7. Shape of container (round, square, rectangular, parabolic, rhombic, or as a collapsible "accordion" or other such flexible container, etc.)
8. Ratio of container cross section to length
9. Ratio of the volume of liquid to the container volume
10. Container temperature
11. Container pressure
12. Container interior surface adhesion characteristics
13. Container gas initial fill rate, exit/purge rate Additionally a control system may use information regarding a total amount of activating agent absorbed to cease the flow of gaseous activating agent to the contact member and/or to initiate flow of a purge gas into the container to achieve a desired total absorption while prevent the total amount of activating agent absorbed from exceeding a pre-specified limit. In some embodiments, the control system may be configured to cease flow of the gaseous activating agent to the contact member and/or to initiate flow of a purge of gas into the container based, at least in part, on the total amount of activating agent absorbed and the rate of gas absorption prior to reaching the desired total absorption such that after all the activating agent has been purged the total desired absorption has been achieved. For example, forward looking software could be employed to calculate and adjust a time to shutoff of flow of the active agent and purge with a non-reactive purge gas to achieve desired total absorption based on the rate of gas absorption by the liquid with a given set-up of adjustable operating parameters (total absorption being the integrated area under the curve including fill rate, stabilized rate and exit/purge rate).

The value of any one parameter (e.g., rotation or oscillation rate, gaseous activating agent employed, gaseous activating agent concentration, input gas flow rate, addition of a diluting non-reactive fluid, adjustment of pH of the fluid, total treatment time) during treatment will likely affect a suitable value or a suitable range of values for one or other parameters during treatment. Some example ranges for values of parameters are listed below; however, one of ordinary skill in the art will appreciate that a suitable parameter for one value will likely be impacted by values selected for one or more other parameters and that a selection of a parameter for one value will likely impact a range of suitable values for one or more other parameters.

In some embodiments, a total time for exposure of the fluid to a gaseous activating agent falls in a range of 5-5,000 seconds (s), 25-25,000 s, or 50-500 s. In some embodiments, the total time for exposure of the fluid to a gaseous activating agent is less than 5 seconds or more than 25,000 s. In some embodiments, a total time for exposure of the fluid to a gas including $O_3$ falls in a range 5-5,000 s, 25-25,000 s, or 50-500 s.

In some embodiments, a maximum concentration of the gaseous activating agent in gas flowing into the contact member during treatment of the fluid falls in a range of 0.005-50%, 0.25-25%, or 0.5-5%. In some embodiments, a maximum concentration of $O_3$ in gas flowing into the contact member during treatment of the fluid falls in a range of 0.005-50%, 0.25-25%, or 0.5-5%.

In some embodiments, a temperature of the fluid is adjusted or maintained using a heating or cooling apparatus. In some embodiments, the heating or cooling apparatus is used to adjust a temperature of the fluid to be a desired temperature and/or to maintain the fluid at the desired temperature, where the desired temperature falls within a range of 10-60° C., 20-50° C., or 30-40° C.

In some embodiments, a biological fluid is diluted or the pH of the biological fluid is adjusted prior to treatment. In some embodiments, one or more of normal saline, Ringer's solution, Hartmann's solution, sodium lactate solution and Plasma-Lyte A is used to dilute or adjust the pH of the biological fluid.

In some embodiments, a pressure within the contact member is adjusted to be above or below atmospheric pressure during some or all of treatments of the fluid with the gaseous activating member.

In some embodiments, a gas inflow rate falls in a range of 0.1-3.2 liters per minute (LPM), 0.2-1.6 LPM, or 0.4-0.8 LPM. In some embodiments, employing ozone, a maximum flow rate may be limited by the input analyzer employed and/or operational characteristics of the ozone generator. In some embodiments employing ozone, a maximum concentration of ozone in the input gas may be limited by the input analyzer employed and or/operational characteristics of the ozone generator. For example, in some embodiments, the ozone concentration of the input gas may be in a range of about 0.5-20 grams per normal cubic meter ($g/Nm^3$), of about 1.0-10 $g/Nm^3$, about 1.5-9 $g/Nm^3$, about 1.8-6 $g/Nm^3$, or about 2.1-5 $g/Nm^3$ where normal (N) refers to standard temperature (0° C.) and pressure (1 atmosphere).

In some embodiments, the rotation rate of the contact member may fall in a range of 0-190 RPM, 0-120 RPM, 0-90 RPM, 0-80 RPM, 0-70 RPM, 0-60 RPM, 0-50 RPM, 0-40 RPM, 0-30 RPM, 0-20 RPM, 0-10 RPM. In some embodiments, a maximum rotation rate employed during treatment of a fluid may fall in a range of 10-190 RPM, 20-120 RPM, 25-100 RPM, 30-90 RPM. In some embodiments, a maximum rotation rate may depend on a weight or a volume of the container, with the larger or heavier container having a lower maximum rotation rate.

As used herein, tolerogenic shall mean the anti-inflammatory immune suppressing and inflammation resolving "type-2" immune phenotype cells the consequence of an AC signaling immune shift that may produce tissue repair, cell regeneration, healing and/or a tolerogenic microenvironment leading to re-establishment of a homeostatic state.

As used herein, dynamic control AC ("dcAC) shall mean a viable AC or AC-like responding body, such as, megakaryocytes, platelets, red blood cells, white blood cells, and endothelial cells produced by the manufacturing as taught by this method evidencing AC-like surface or secreted signaling, communicating or immunomodulation activity (structurally, these responding bodies may present surface inside-out and sometimes outside-in cell fragments having a bilayered phospholipid structure exposing coagulant-active phosphatidylserine, or other lipid or protein formation, expressing various membrane receptors that serve as cell-to-cell shuttles for bioactive molecules such as lipids, growth factors, microRNAs, and mitochondria). The dcAC signal activated immune and immune-like cells shift from immunogenic to tolerogenic phenotypes producing healing and homeostasis (such an immune shift is associated with a process coined "efferocytosis", although the AC induced tolerogenic shift is not dependent upon actual engulfment) .[16] A novelty of dynamic control is that its inherit controlled process with multiple operating parameter variations provides flexibility to generate multiple variations in its products by process as evidenced by variation in the compositional and functional characteristics of the dcAC.

As used herein, "immunogenesis" and "immunogenic" shall mean the reactive response of immune cells, pro-inflammatory and tissue/cell stressing in nature, in a sever initial activation or non-resolved state, which may create a sustained disease or injurious response with a chronic, hyper-activated and expansive dysregulated "type-1" immune phenotype that amplifies and perpetuates a progressive and degenerative pathologic condition.

Cells made by the methods disclosed herein are useful in treating disease. Accordingly, the cells, e.g., the apoptotic cells, can be used to treat or prevent diseases such as those disclosed below. One of ordinary skill in the art will be able to determine the proper amount of AC to administer and a regime that would be effective for treating or preventing a specific disease.

i. Autoimmune Diseases and Autoimmune-Like Diseases:

Including—acute disseminated encephalomyelitis (ADEM), acute necrotizing hemorrhagic leukoencephalitis, Addison's disease, agammaglobulinemia, alopecia areata, amyloidosis, ankylosing spondylitis, anti-GBM/anti-TBM nephritis, antiphospholipid syndrome, autoimmune angioedema, autoimmune aplastic anemia, autoimmune dysautonomia, autoimmune hemolytic anemia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticarial, axonal & neuronal neuropathies, balo disease, Behcet's disease, bullous pemphigoid, ardiomyopathy, Castleman disease, celiac disease, chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogans syndrome, cold agglutinin disease, congenital heart block, Coxsackie myocarditis, CREST disease, cutaneous T-cell lymphoma (CTCL) demyelinating neuropathies, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, Essential mixed cryoglobulinemia, experimental allergic encephalomyelitis, Evans syndrome, fibromyalgia, fibrosing alveolitis, giant cell arteritis (temporal arteritis), giant cell myocarditis, glomerulonephritis, Goodpasture's syndrome, granulomatosis with polyangiitis (GPA) (formerly called Wegener's Granulomatosis), Graves' disease, Guillain-Barré syndrome, Hashimoto's encephalitis, Hashimoto's thyroiditis, hemolytic anemia, Henoch-Schonlein purpura, herpes gestationis, hypogammaglobulinemia, idiopathic pulmonary fibrosis, idiopathic thrombocytopenic purpura (ITP), IgA nephropathy, IgG4-related sclerosing disease, immunoregulatory lipoproteins, inclusion body myositis, interstitial cystitis, juvenile arthritis, juvenile diabetes (Type 1 diabetes), juvenile idiopathic arthritis, juvenile myositis, Kawasaki syndrome, Lambert-Eaton syndrome, Leukocytoclastic vasculitis, Lewy body disease, lichen planus, lichen sclerosus, ligneous conjunctivitis, linear IgA disease (LAD), lyme disease, chronic, Meniere's disease, microscopic polyangiitis, mixed connective tissue disease (MCTD), Mooren's ulcer, motor neuron diseases, Mucha-Habermann disease, multiple sclerosis, myasthenia gravis, myocarditis, myositis narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, Parkinson's disease (PD) and PD-related disorders, paroxysmal nocturnal hemoglobinuria (PNH), Parry Romberg syndrome, Parsonnage-Turner syndrome, pars planitis, peripheral uveitis, pemphigus/pemphigoid, peripheral neuropathy, pernicious anemia, perivenous encephalomyelitis, POEMS syndrome, polyarteritis nodosa, Type I, II, & III autoimmune polyglandular syndromes, polymyalgia rheumatic, polymyositis, postmyocardial infarction syndrome, postpericardiotomy syndrome, primary biliary cirrhosis, primary immunodeficiency, primary sclerosing cholangitis, progesterone dermatitis, psoriasis, psoriatic arthritis, pyoderma gangrenosum, pure red cell aplasia, Raynauds phenomenon, reactive arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), Susac's syndrome, sympathetic ophthalmia, systemic lupus erythematosus (SEL), Takayasu's arteritis, temporal arteritis/giant cell arteritis, thrombocytopenic purpura (TTP), thyroiditis, Tolosa-Hunt syndrome, transverse myelitis, Type 1 diabetes, ulcerative colitis, undifferentiated connective tissue disease (UCTD), uveitis, vasculitis, vesiculobullous dermatosis, vitiligo, Wegener's granulomatosis (now termed Granulomatosis with Polyangiitis (GPA).

ii. Cardiovascular Diseases:

Including—angina pectoris. atherosclerosis, hypertension, carotid artery disease, claudication, chronic heart failure, congestive heart failure (including acute systolic, chronic systolic and unspecified diastolic), coronary heart disease, coronary artery disease, chronic heart failure, deep vein thrombosis, diabetic cardiomyopathy, hypertensive heart disease, ischemic diseases (including acute kidney injury, chronic kidney disease, critical limb disease, cerebral stroke, and TIA—transient ischemic attack) myocardial infarction, peripheral artery disease, pulmonary arterial hypertension, renal artery stenosis, Rheumatic heart disease, valvular heart disease, and cellular disorders, e.g., vascular smooth muscle cell proliferation and apoptosis.

iii. Inheritable or Genetic Neurodegenerative Diseases:

Including—Down syndrome, Leber's hereditary optic neuropathy (LHON), or Usher syndrome.

iv. Metabolic, ImmunoMetabolism and Metabolic-Like Diseases

Including—diabetes, syndrome X, non-alcoholic fatty liver disease, insulin resistance, adipose tissue inflammation, acid lipase disease, Barth syndrome, central pontine myelinolysis, Farber's disease, gangliosidoses, hepatitis A/B metabolic reprogramming, Hunter syndrome, Hurler syndrome, hyperoxaluria, immuno-insulin resistance, Lesch- Nyhan syndrome, lipid storage diseases, metabolic diseases of muscle, metabolic myopathies, mitochondrial myopathies, mucolipidoses, mucopoly-saccharidoses, Pompe disease, smoking-induced abdominal aortic aneurysm, trimethylaminuria, Type I glycogen storage disease, urea cycle disease.

v. Neural Degenerative Diseases (and Neurodegenerative-Like Diseases or Conditions):

including stroke (both ischemic and hemorrhagic), traumatic brain injuries, chronic traumatic encephalopathy and more broadly, amyotrophic lateral sclerosis, Alpers' Disease, Alzheimer's disease, ataxia telangiectasia, autosomal dominant cerebellar ataxia, Baggio-Yoshinari syndrome, Batten Disease, Cerebro-Oculo-Facio-Skeletal Syndrome (COFS), corticobasal degeneration, Creutzfeldt-Jakob disease, fatal familial insomnia, frontotemporal dementia and Parkinsonism linked to chromosome 17, Friedreich's ataxia, Gerstmann-Straussler-Scheinker Disease, hereditary motor and sensory neuropathy with proximal dominance, Hodgkin's disease, Huntington's disease, Infantile Refsum disease, JUNQ and IPOD, Kuru, Leigh's Disease, locomotor ataxia, Lyme disease, Machado-Joseph disease, mental retardation and microcephaly with pontine and cerebellar hypoplasia, mild cognitive impairment, multiple system atrophy, multiple system atrophy with orthostatic hypotension (Shy-Drager Syndrome), neuroacanthocytosis, Niemann-Pick disease, neurodegenerative aging, neurodegeneration with brain iron, opsoclonus myoclonus, pontocerebellar hypoplasia, posterior cortical atrophy (PCA)—Benson's syndrome, primary progressive aphasia, prion diseases, progressive multifocal leukoencephalopathy, progressive supranuclear palsy, pyruvate dehydrogenase deficiency, Refsum disease, Rubinstein-Taybi syndrome, Sandhoff disease, Shy-Drager syndrome, spinal muscular atrophy, spinocerebellar ataxia, spinal muscular atrophy, subacute combined degeneration of spinal cord, subacute sclerosing panencephalitis, tabes dorsalis, Tay-Sachs disease, toxic encephalopathy, toxic leukoencephalopathy, Transmissible Spongiform Encephalopathies (Prion Diseases), Vascular Dementia, Wobbly hedgehog syndrome.

vi. Neurodevelopmental Disorders:

Including Autism spectrum disorders (autism, Asperger syndrome, pervasive developmental disorder not otherwise specified (PDD-NOS), and childhood disintegrative disorder).

vii. Neuropsychiatric Disorders:

Including—generalized anxiety disorder, attention deficit hyperactivity disorder (ADHD), bipolar, delirium, depression, obsessive-compulsive disorder, post-traumatic stress, social anxiety disorder (SAD), social phobia, panic disorder, agoraphobia viii. Pathological Pain:

Including—allodynia, dysesthesias, "extra-territorial", hyperalgesia, neuropathic (complex regional pain syndromes—peripheral nerve trauma and/or inflammation, autoimmune neuropathies, vasculitic neuropathies), nociceptive, paraesthesias.

ix. Sepsis, Septic Shock and Endotoxin-Like Diseases:

Including—multi organ dysfunction syndrome (MODS), surgical sepsis, postoperative cognitive dysfunction (POCD), post-traumatic sepsis, and systemic inflammatory response syndrome (SIRS).

x. Transplant Immune Rejection:

Including—allograft, bone marrow, corneal, coronary artery bypass grafting (CABG),Graft verse Host Disease (GvHD), solid organ, stem cell and xenograft.

Accordingly, methods of treating the aforementioned diseases by administering AC created by any of the methods disclosed herein are provided. In one embodiment, the AC created by the methods disclosed herein can be administered alone. In another embodiment, the AC created by the methods disclosed herein can be administered, e.g., co-administered, along with an immune modulator such as immunogenic suppressors/resolvers, tolerogenic inducers, or homeostasis generators. For example, the AC cells of the invention can be co-administered along with inflammation inhibitors (e.g., glucocorticoids—beclomethasone, betamethasone, Budesonide, cortisone, dexamethasone, prednisolone), GMARDs (e.g., abatacept, adalimumab, azathioprine, ciclosporin, etanercept, golimumab, gold salts, hydroxychloroquine, infliximab, leflunomide, methotrexate, minocycline, pyrimethamine, rituximab, sulfasalazine); immune tolerance cells (e.g., stem cells, myeloid-derived suppressor cells, bone morrow cells—including any expression, faction, particle, exudation, or emission thereof); vasodilators (e.g., alprostadil, nesiritide, nitroglycerin, or nitroprusside); COX-1,-2 inhibitors (e.g., valdecoxib, rofecoxib, celecoxib, SC-560, FR122047, mofezolac, P6, TFAP, aspirin, indomethacin, ibuprofen, naproxen, piroxicam, or nabumetone); AMPK activators and inducers of adenosine release/metabolism (Metformin, AICAR, berberine/berberine derivatives), electromagnetic stimulation. In another embodiment, the AC cells of the invention can be administered before or after treatment with one or more of the immunogenic suppressors/resolvers, tolerogenic inducers, or homeostasis generators disclosed herein.

EXAMPLES

A system was constructed according to embodiments depicted and described above with respect to FIGS. 1, 3, 4, and 6A-6C. Tests using the system were conducted using a borosilicate glass bottle having a volume of 1,000 mL as a container, which was rotated in a range of 29-35 rotations per minute (RPM) while blood was present in the container.

A. Determination of Approximate Fluid Film Thickness

The following procedure was employed to yield an approximate estimate of the blood film thickness during rotation of a borosilicate glass bottle having a volume of 1,000 mL at 35 RPM.

A small amount of sheep's blood in citrate was placed in the glass bottle and the bottle was rotated at 35 RPM. The interior surface of the bottle was covered with a film of blood and there was also a small pool of blood remaining during rotation. The process was stopped and a small of amount of blood was removed. The process was repeated, which resulted in a smaller pool of blood present while the bottle was rotating.

This process was repeated until there was no pool of blood in the bottle, but the film of blood remained complete during rotation at which point the process was stopped and the volume of blood that had formed the film inside the bottle was measured. The volume of blood was found to be 18.7 mL or 18.7 cm$^3$. Next the interior surface area of the bottle was estimated. The inside diameter of the bottle was approximately 9.22 cm and the length of the film was approximately 15 cm. Therefore the surface contact area of the film was approximately 434.5 cm$^2$. The film thickness was estimated by dividing the volume of blood by the surface area of the film yielding a film thickness of approximately 0.041 cm or 0.41 mm.

B. Infusion of 100 mL of Blood with Automated Dose Control

Figure 17:
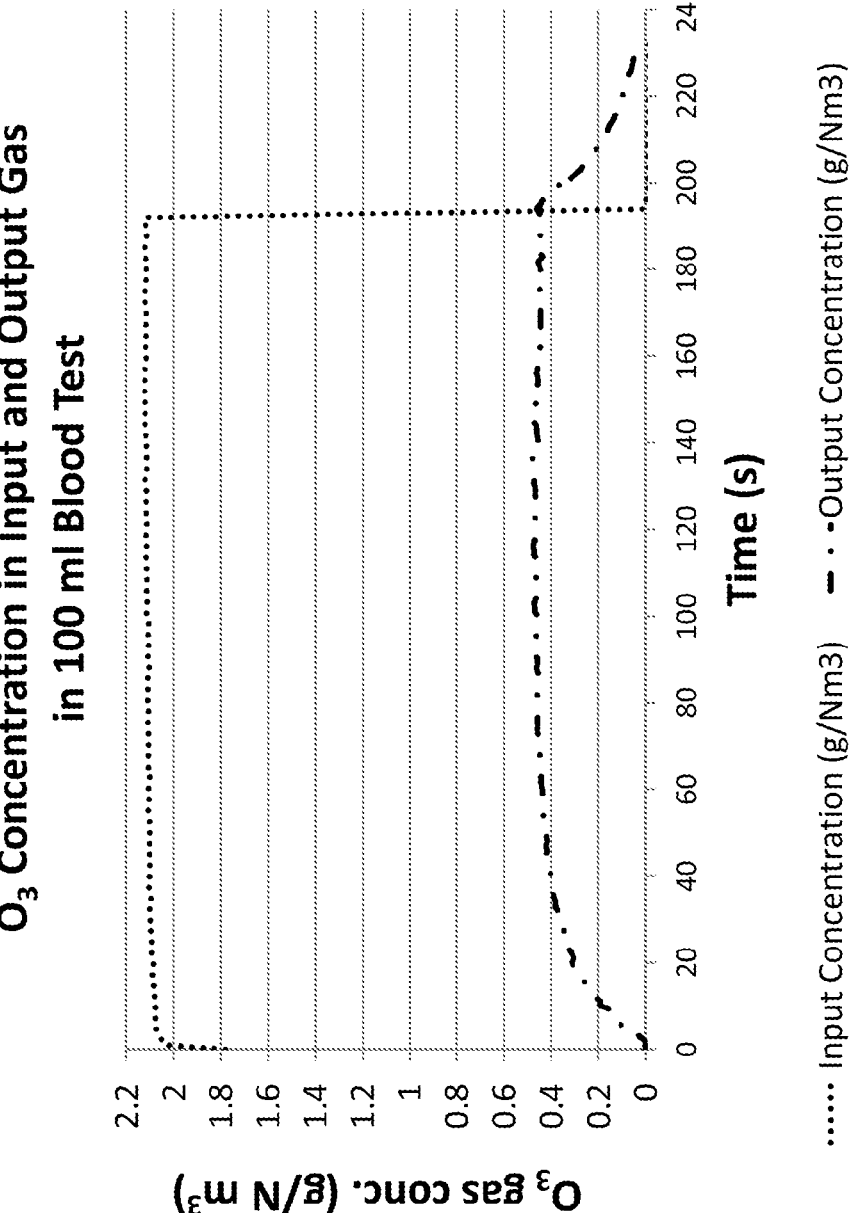
FIG. 17 is a graph of ozone concentration in gas input to a container and ozone concentration of gas output from the container during an experimental run infusing 100 mL of blood with ozone while employing automated control to achieve a pre-selected desired dose.

The system was used to infuse 100 mL of sheep's blood in citrate with ozone. The container employed was again a borosilicate glass bottle having a volume of 1,000 mL. The fluid was added to the container, which was rotated at 28-32 RPM. While the container was rotating, an input gas including ozone flowed into the container where the ozone concentration in the input gas was about 2.1 g/m$^3$. FIG. 17 is a graph of the measured ozone concentration of the gas entering the container (labeled "input") and the measured ozone concentration of the gas leaving the container (labeled "output"). At any point in time, the difference between the input concentration and the output concentration indicates the ozone being absorbed by the fluid in the container. At an elapsed time of about 195 seconds (3 minutes and 15 seconds), the flow of ozone into the container ceased. As shown, the output concentration of ozone gradually trailed off as the rest of the ozone in the container flowed out.

Figure 18:
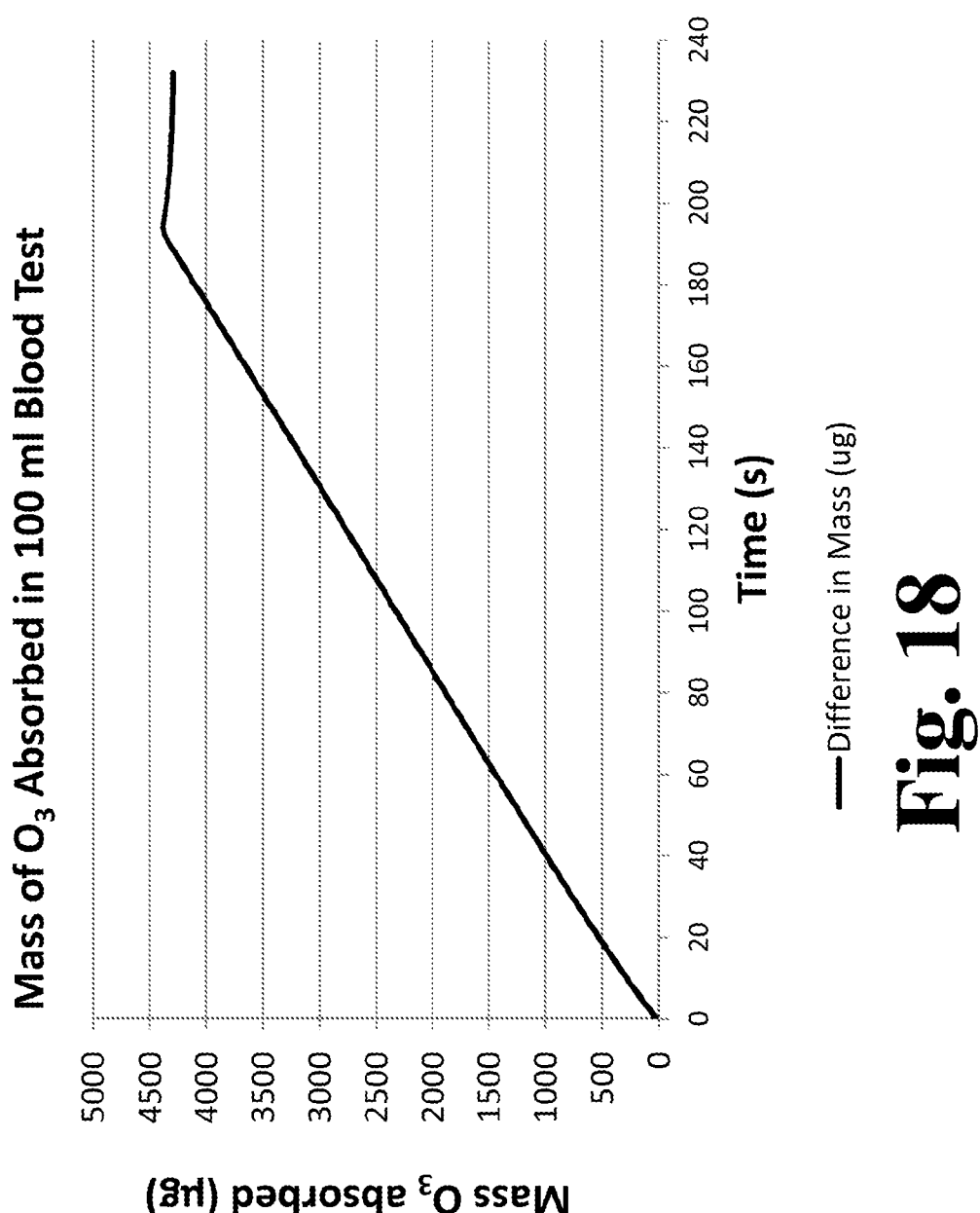
FIG. 18 is a graph of ozone mass absorbed by the fluid during the experimental run infusing 100 mL of blood with ozone.

FIG. 18 is a graph of the total mass of ozone absorbed by the fluid (left axis) as a function of time. As shown, the total mass of ozone absorbed by the fluid increases approximately linearly in time until it reaches a value of about 4,390 m at about 195 seconds (3 minutes, 15 seconds) of treatment. In this test, the control system determined the total mass of ozone absorbed by the fluid in real time automatically shut off the ozone generator to achieve a pre-specified desired total dose.

C. Infusion of 200 mL of Blood

The system was also used to infuse 200 mL of sheep's blood in citrate with ozone. The container employed was again borosilicate glass bottle having a volume of 1,000 mL. The fluid was added to the container, which was rotated at 28-33 RPM. While the container was rotating, an input gas including ozone flowed into the container where the ozone concentration in the input gas was about 2.1 g/m$^3$. In this test, instead of automatically stopping the system to achieve a desired pre-specified dose of ozone, the infusion was carried out for an extended period of time to examine absorption behavior.

Figure 19:
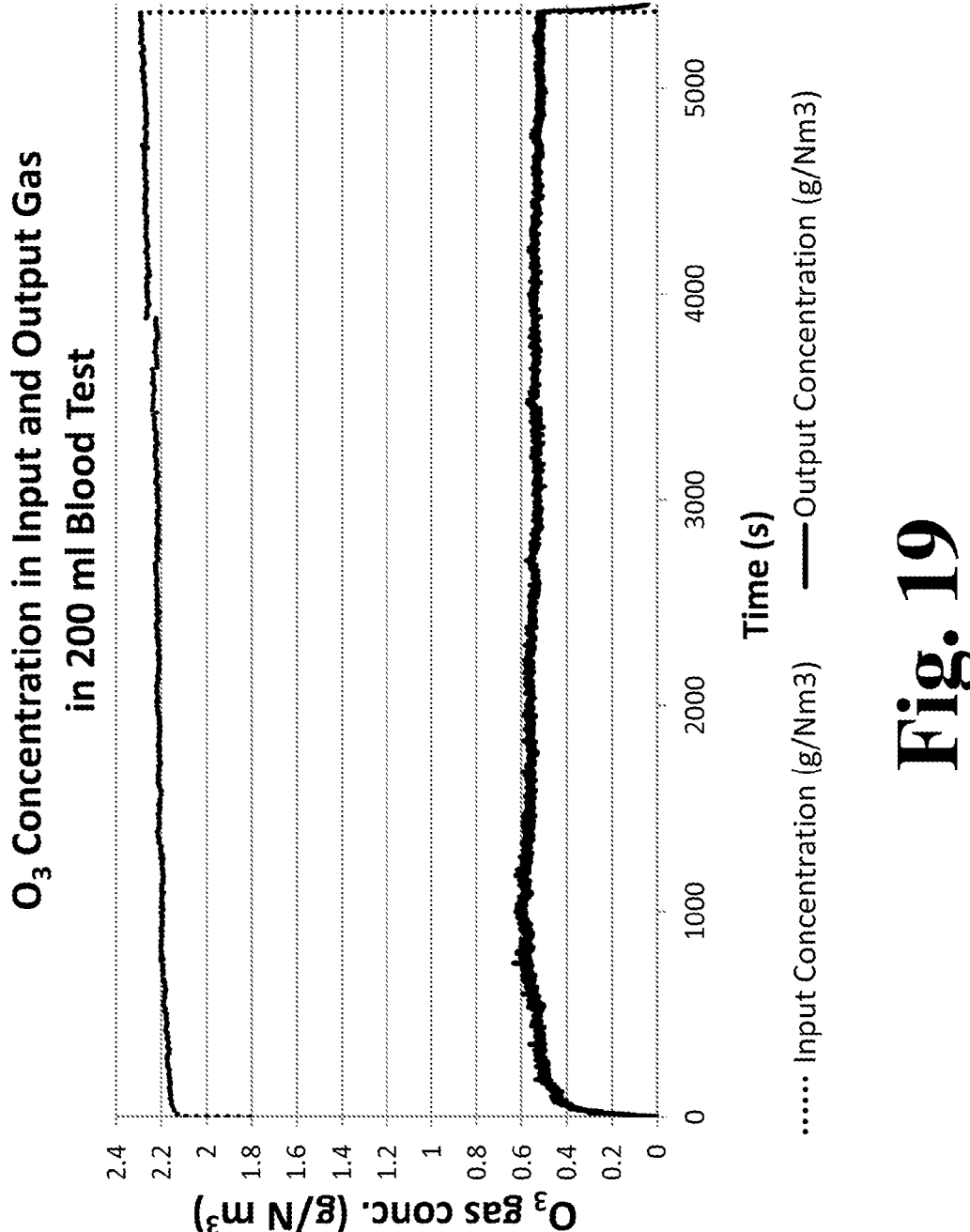
FIG. 19 is a graph of ozone concentration in gas input to a container and ozone concentration of gas output from the container during an extended experimental run infusing 200 mL of blood with ozone.

FIG. 19 is a graph of the measured ozone concentration of the gas entering the container and the measured ozone concentration of the gas leaving the container. At any point in time, the difference between the input concentration and the output concentration indicates the ozone being absorbed by the fluid in the container. The infusion continued for 5,337 seconds (about 1.5 hours), after which the concentration of ozone in the input gas dropped to zero.

Figure 20:
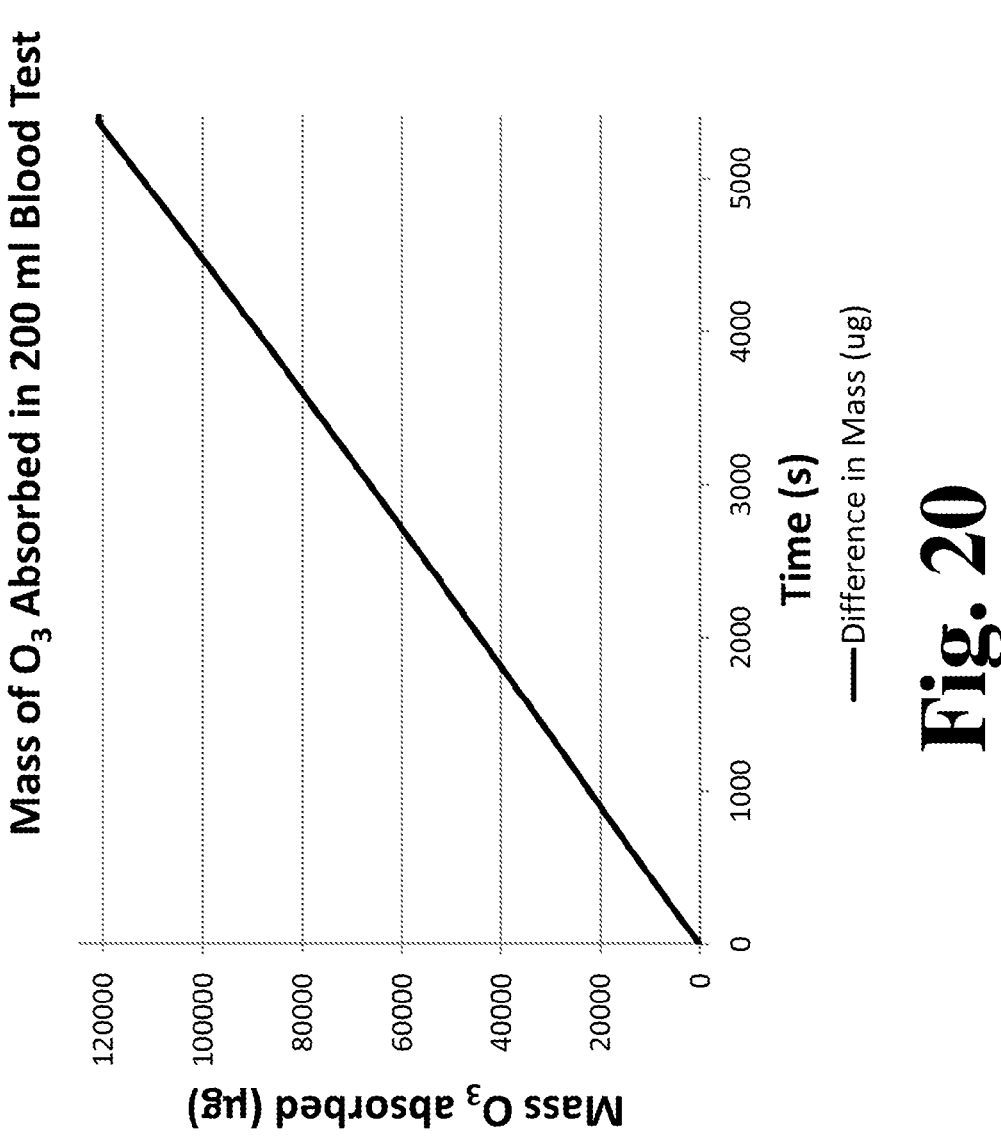
FIG. 20 is a graph of ozone mass absorbed by the fluid during the experimental run infusing 200 mL of blood with ozone.

FIG. 20 is a graph of the total absorbed ozone as a function of time. As shown in FIG. 20, the total mass of ozone absorbed increased approximately linearly throughout the test to a total of about 120,920 µg at the end of the infusion.

Various modifications to the example embodiments will be readily apparent to those skilled in the art, and the generic principles defined herein may be applied to other embodiments and applications without departing from the spirit and scope of the invention. Moreover, in the preceding description, numerous details are set forth for the purpose of explanation. However, one of ordinary skill in the art will realize that the invention may be practiced without the use of these specific details. In other instances, well-known structures and processes are shown in schematic or block diagram form in order not to obscure the description of the invention with unnecessary detail. Thus, the present disclosure is not intended to be limited to the embodiments shown, but is to be accorded the widest scope consistent with the principles, features and any combination of such disclosed herein.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes multiple system elements, device components or method steps, those elements, components or steps can be replaced with a single element, component or step. Likewise, a single element, component or step can be replaced with multiple elements, components or steps that serve the same purpose. Moreover, while exemplary embodiments have been shown and described with references to particular embodiments thereof, those of ordinary skill in the art will understand that various substitutions and alterations in form and detail can be made therein without departing from the scope of the invention. Further still, other aspects, functions and advantages are also within the scope of the invention.

While the embodiments have been illustrated and described in detail in the drawings and foregoing description, the same is to be considered as illustrative and not restrictive in character, it being understood that only certain embodiments have been shown and described and that all changes and modifications that come within the spirit of the embodiments are desired to be protected.

REFERENCES

[1] Zhang D W, Shao J, Lin J, Zhang N, Lu B J, Lin S C et al. (2009), *Science,* 325: 332-336, RIP3, an energy metabolism regulator that switches TNF-induced cell death from apoptosis to necrosis.

[2] Cho Y S, Challa S, Moquin D, Genga R, Ray T D, Guildford M et al. (2009), *Cell,* 137: 1112-1123, Phosphorylation-driven assembly of the RIP1-RIP3 complex regulates programmed necrosis and virus-induced inflammation.

[3] Sun L, Wang H, Wang Z, He S, Chen S, Liao D et al. (2012), *Cell,* 148: 213-227, Mixed lineage kinase domain-like protein mediates necrosis signaling downstream of RIP3 kinase.

[4] Cal Z, Jitkaew S, Zhao J, Chiang H C, Choksi S, Liu J et al. (2014), *Nat Cell Biol,* 16:55-65, Plasma membrane translo cation of trimerized MLKL protein is required for TNF-induced necroptosis.

[5] Wang H, Sun L, Su L, Rizo J, Liu L, Wang L F et al. (2014), *Mol Cell,* 54:133-146, Mixed lineage kinase domain-like protein mlkl causes necrotic membrane disruption upon phosphorylation by RIP3

[6] Vanden Berghe T, Kaiser W J, Bertrand M J, Vandenabeele P (2015), *Mol Cell Oncol,* 2(4):e975093, Molecular crosstalk between apoptosis, necroptosis, and survival signaling.

[7] Merrill E W (1969), *PhysiolRev,* Rheology of blood.

[8] Symphony Chakraborty (2012), *PhD Thesis, Universite Pierre et Marie Curie—Paris VI,* Dynamics and stability of a non-Newtonian thin film, Mechanics [physics.med-ph].

[9] Almgren R, Behringer R P, Bertozzi A L, Pugh M C, Shearer M, Witelski T P (2003), *Banff Institute Workshop,* Nonlinear Dynamics of Thin-films and Fluid Interfaces.

[10] Dorfman L M, Adams G E (1973), *National Bureau of Standards,* Report No. NSRDS-NBS-46, Reactivity of the Hydroxyl Radical.

[11] Fadeel B, Ottosson A, Pervaiz S. Big wheel keeps on turning: apoptosome regulation and its role in chemoresistance. *Cell Death Differ.* 2008; 15(3):443-52.

[12] Gu S, Liu Z, Pan S, Jiang Z, Lu H, Amit O, Bradbury E M, Hu C A, Chen X (2004), *Mol Cell Proteomics,* 3(10):998-1008, Global investigation of p53-induced apoptosis through quantitative proteomic profiling using comparative amino acid-coded tagging.

[13] Wang H, Wu Q, Li S, Zhang B, Chi Z, Hao L (2014), *Mol Med Rep,* 9(6):2411-2416, Unc5D regulates p53-dependent apoptosis in neuroblastoma cells.

[14] Vota D M, Maltaneri R E, Wenker S D, Nesse A B, Vittori D C (2013), Cell Biochem Biophys, 65(2):145-157, Differential erythropoietin action upon cells induced to eryptosis by different agents.

[15] Tesoriere L, Attanzio A, Allegra M, Cilla A, Gentile C, Livrea M A (2014), *Cell Physiol Biochem,* 34(4):1075-1089, Oxysterol mixture in hypercholesterolemia-relevant proportion causes oxidative stress-dependent eryptosis.

[16] Cvetanovic M, Ucker D S (2004), J Immunol, 172(2): 880-889, Innate immune discrimination of apoptotic cells: repression of proinflammatory macrophage transcription is coupled directly to specific recognition.

We claim:

1. An apparatus for treating a fluid comprising a biological liquid and/or cells or particles derived from a biological liquid with an activating agent, the apparatus comprising:

a gas-fluid contact device configured to controllably rotate a contact member, the contact member configured to receive the fluid and having an interior surface configured to be in contact with the received fluid;

a gas inlet line configured to receive a gas comprising the activating agent from a gas source for delivery to the contact member;

one or more first sensors for analyzing a composition of the gas from the gas source to be delivered to the gas-fluid contact device;

a gas outlet line for outputting gas from the contact member;

one or more second sensors for analyzing a composition of the gas output from the gas-fluid contact device; and a control system configured to:

control rotation of the contact member by the gas-fluid contact device, and control one or both of a flow rate of the gas into the contact member and a composition of the gas flowing into the contact member;

continuously or periodically determine a current total amount of activating agent absorbed by or reacted with the fluid based on measurements from the one or more first sensors and the one or more second sensors;

determine a current rate of activating agent absorption by or reaction with the fluid; and cease flow of the gas comprising the activating agent to the contact member and/or initiate flow of a purge gas into the contact member before the current total amount of activating agent absorbed by or reacted with the fluid equals a total pre-specified desired amount based, at least in part, on the current total amount of activating agent absorbed by or reacted with the fluid and the current rate of activating agent absorption by or reaction with the fluid such that after all the activating agent has been purged, the total pre-specified desired amount of activating agent absorbed by or reacted with the fluid has been achieved without exceeding a pre-specified limit.

2. The apparatus of claim 1, wherein the control system is configured to determine the current rate of activating agent absorption by or reaction with the fluid based on the composition of the gas delivered to the gas-fluid contact device and flowing into the contact member, the composition of the gas flowing out of the contact member and output from gas-fluid contact device, and the flow rate of gas through the gas-fluid contact device and into the contact member.

3. The apparatus of claim 1, wherein the control system is configured to alter one or both of the composition of the gas delivered to the gas-fluid contact device and into the contact member and the flow rate of the gas delivered to the gas-fluid contact device and into the contact member based, at least in part, on the determined current rate of activating agent absorption by or reaction with the fluid.

4. The apparatus of claim 1, wherein the control system is further configured to continuously or periodically determine a current estimate of a total activating agent contact time required to achieve the total pre-specified desired amount of the activating agent absorbed by or reacted with the fluid based, at least in part, on the determined current rate of activating agent absorption of or reaction by the fluid.

5. The apparatus of claim 1, wherein the gas-fluid contact device further comprises a first fluid tube configured to be connected with a first fluid line for delivering the fluid to be treated into the contact member.

6. The apparatus of claim 5, wherein the first fluid tube is also configured for removal of the treated fluid from the contact member.

7. The apparatus of claim 1, wherein the gas-fluid contact device further comprises a second fluid tube configured to be connected with a second fluid line for removal of the treated fluid from the contact member.

8. The apparatus of claim 1, wherein the apparatus is configured to enable at least a portion of the gas-fluid contact device that engages the contact member to be rotatably or pivotably tilted to facilitate removal of the fluid from the contact member via gravity.

9. The apparatus of claim 1, further comprising a pivotable joint enabling a portion of the gas-fluid contact device that engages the contact member to be tilted relative to another portion of the apparatus to facilitate removal of the treated fluid from the contact member via gravity.

10. The apparatus of claim 1, wherein the apparatus further comprises a rotating joint configured to:

sealably and rotatably couple the contact member to the gas-fluid contact device;

connect the gas inlet line with the contact member;

connect the gas outlet line with the contact member; and remain connected to the gas inlet line and the gas outlet line during rotation of the contact member.

11. The apparatus of claim 10, wherein the rotating joint is further configured to receive the fluid to be treated from a first fluid line and to remain connected to the first fluid line during rotation of the contact member.

12. The apparatus of claim 11, wherein the rotating joint comprises:

a gas inlet tube configured to connect with the gas inlet line;

a gas outlet tube configured to connect with the gas outlet line; and a first fluid tube configured to connect with the first fluid line.

13. The apparatus of claim 12, wherein the rotating joint further comprises a second fluid tube configured to connect with a second fluid line for draining the treated fluid from the contact member.

14. The apparatus of claim 12, wherein the first fluid tube is a first fluid inlet and outlet tube and the first fluid line is a first inlet and outlet fluid line.

15. The apparatus of claim 1, wherein the apparatus is configured for providing the treated fluid for infusion into a patient without exposing the treated fluid to open air.

16. The apparatus of claim 1, wherein the apparatus is configured for obtaining the fluid from a patient, treating the fluid, and providing the treated fluid for reinfusion into the patient without exposing the treated fluid to open air.

17. An apparatus for treating a fluid comprising a biological liquid and/or cells or particles derived from a biological liquid with an activating agent, the apparatus comprising:

a gas-fluid contact device configured to controllably rotate a contact member, the gas-fluid contact device comprising one or more rollers configured to contact an outer surface of the contact member to drive rotation of the contact member, at least one of the one or more rollers driven by a motor, the contact member configured to receive the fluid and having an interior surface configured to be in contact with the received fluid;

a gas inlet line configured to receive a gas comprising the activating agent from a gas source for delivery to the contact member;

one or more first sensors for analyzing a composition of the gas from the gas source to be delivered to the gas-fluid contact device;

a gas outlet line for outputting gas from the contact member;

one or more second sensors for analyzing a composition of the gas output from the gas-fluid contact device; and a control system configured to:

control rotation of the contact member by the gas-fluid contact device, and control one or both of a flow rate of the gas into the contact member and a composition of the gas flowing into the contact member;

continuously or periodically determine a current total amount of activating agent absorbed by or reacted with the fluid based on measurements from the one or more first sensors and the one or more second sensors;

determine a current rate of activating agent absorption by or reaction with the fluid; and cease flow of the gas comprising the activating agent to the contact member and/or initiate flow of a purge gas into the contact member before the current total amount of activating agent absorbed by or reacted with the fluid equals a total pre-specified desired amount based, at least in part, on the current total amount of activating agent absorbed by or reacted with the fluid and the current rate of activating agent absorption by or reaction with the fluid such that after all the activating agent has been purged, the total pre-specified desired amount of activating agent absorbed by or reacted with the fluid has been achieved without exceeding a pre-specified limit.

18. An apparatus for treating a fluid comprising a biological liquid and/or cells or particles derived from a biological liquid with an activating agent, the apparatus comprising:

a gas-fluid contact device configured to controllably rotate a contact member, the contact member configured to receive the fluid and having an interior surface configured to be in contact with the received fluid;

a gas inlet line configured to receive a gas comprising the activating agent from a gas source for delivery to the contact member;

one or more first sensors for analyzing a composition of the gas from the gas source to be delivered to the gas-fluid contact device;

a gas outlet line for outputting gas from the contact member;

one or more second sensors for analyzing a composition of the gas output from the gas-fluid contact device; and a control system configured to:

control rotation of the contact member by the gas-fluid contact device, and control one or both of a flow rate of the gas into the contact member and a composition of the gas flowing into the contact member;

continuously or periodically determine a current total amount of activating agent absorbed by or reacted with the fluid based on measurements from the one or more first sensors and the one or more second sensors;

determine a current rate of activating agent absorption by or reaction with the fluid; and cease flow of the gas comprising the activating agent to the contact member and/or initiate flow of a purge gas into the contact member before the current total amount of activating agent absorbed by or reacted with the fluid equals a total pre-specified desired amount based, at least in part, on the current total amount of activating agent absorbed by or reacted with the fluid and the current rate of activating agent absorption by or reaction with the fluid such that after all the activating agent has been purged, the total pre-specified desired amount of activating agent absorbed by or reacted with the fluid has been achieved without exceeding a pre-specified limit, wherein the apparatus is configured for between 8% and 35% of a volume of the contact member be filled with the fluid during rotation of the contact member.

* * * * *